United States Patent
Kumar et al.

(10) Patent No.: US 6,517,778 B1
(45) Date of Patent: Feb. 11, 2003

(54) IMMUNOASSAYS IN CAPILLARY TUBES

(75) Inventors: Amit Kumar, Milpitas, CA (US); Larry Sheldon Jang, San Jose, CA (US); Danton Kai-Yu Leung, Los Altos, CA (US); Richard Michele Rocco, Sunnyvale, CA (US); Mark Charles Platshon, Menlo Park, CA (US)

(73) Assignee: IDEXX Laboratories, Westbrook, ME (US)

( * ) Notice: Subject to any disclaimer, the term of this patent is extended or adjusted under 35 U.S.C. 154(b) by 0 days.

(21) Appl. No.: 09/361,391

(22) Filed: Jul. 26, 1999

Related U.S. Application Data

(60) Division of application No. 08/688,043, filed on Jul. 29, 1996, now Pat. No. 5,976,896, which is a continuation-in-part of application No. 08/254,032, filed on Jun. 6, 1994, now Pat. No. 5,624,850.

(51) Int. Cl.[7] .............................................. G01N 21/47
(52) U.S. Cl. ................... 422/82.05; 436/527; 422/68.1; 422/101; 422/104; 422/100; 422/64; 422/82.08
(58) Field of Search ............................. 422/82.05, 68.1, 422/101, 104, 100, 64, 57, 82.07, 82.08; 436/527, 20, 23, 172, 538; 250/288

(56) References Cited

U.S. PATENT DOCUMENTS

| | | | |
|---|---|---|---|
| 4,116,638 A | | 9/1978 | Kenoff ........................ 422/99 |
| 4,590,157 A | | 5/1986 | Chandler et al. .............. 435/7 |
| 4,716,121 A | | 12/1987 | Block et al. ................. 436/514 |
| 4,746,490 A | * | 5/1988 | Saneii .......................... 422/62 |
| 5,288,464 A | * | 2/1994 | Nokihara .................... 422/101 |
| 5,320,808 A | * | 6/1994 | Holen et al. .................. 422/64 |
| 5,324,483 A | * | 6/1994 | Cody et al. ................. 422/131 |
| 5,624,850 A | * | 4/1997 | Kumar et al. ............... 436/527 |
| 5,632,957 A | * | 5/1997 | Heller et al. .............. 422/68.1 |
| 5,959,297 A | * | 9/1999 | Weinberg et al. ........... 250/288 |
| 6,121,054 A | * | 9/2000 | Lebl ........................... 436/177 |
| 6,132,685 A | * | 10/2000 | Kereso et al. .............. 422/104 |

* cited by examiner

Primary Examiner—Jill Warden
Assistant Examiner—Brian Sines
(74) Attorney, Agent, or Firm—McDonnell, Boehnen Hulbert & Berghoff

(57) ABSTRACT

A fluorescent immunoassay employing the interior surface of a capillary tube is provided. Devices to permit immunoassays using one or more capillary tubes, an apparatus for use with the devices, and a process for screening for analyte in a sample using the devices and apparatus are also provided. Samples suspected of containing analyte are added to a disposable self-contained sample tray containing one or more sample wells, mixed with a reagent, drawn into one or more spaced-apart capillary tubes held within a disposable cartridge connected to an analytical apparatus, reacted with a binding member on the surface of the capillary tube, washed to stop the reaction, and dried by the apparatus. The capillary tube is then exposed to a signal generation device to create a fluorescence signal that is detected using a signal detector. The apparatus determines the presence of the analyte and optionally determines the amount of analyte present in the sample, and presents the results to the operator.

42 Claims, 25 Drawing Sheets

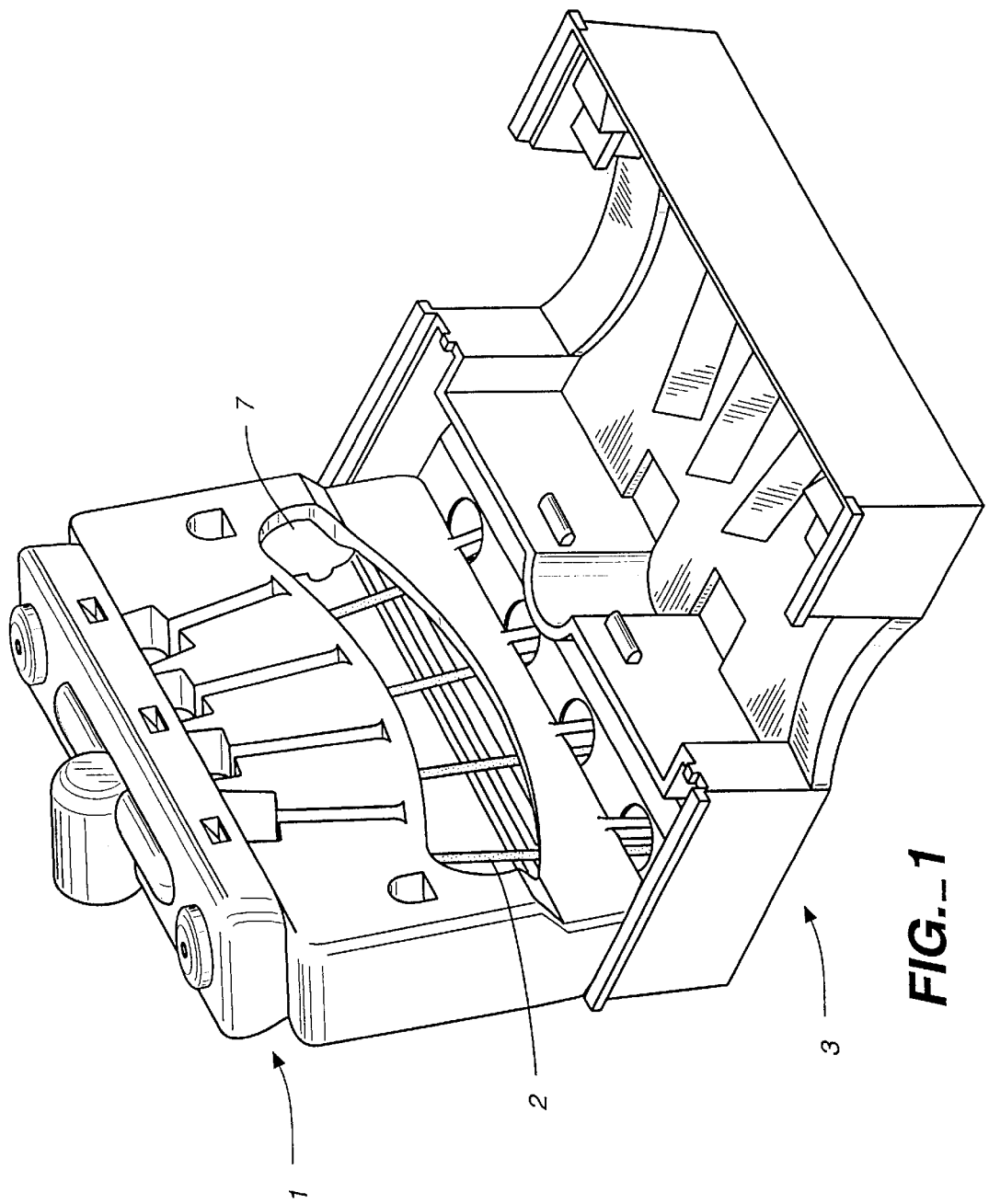
FIG._1

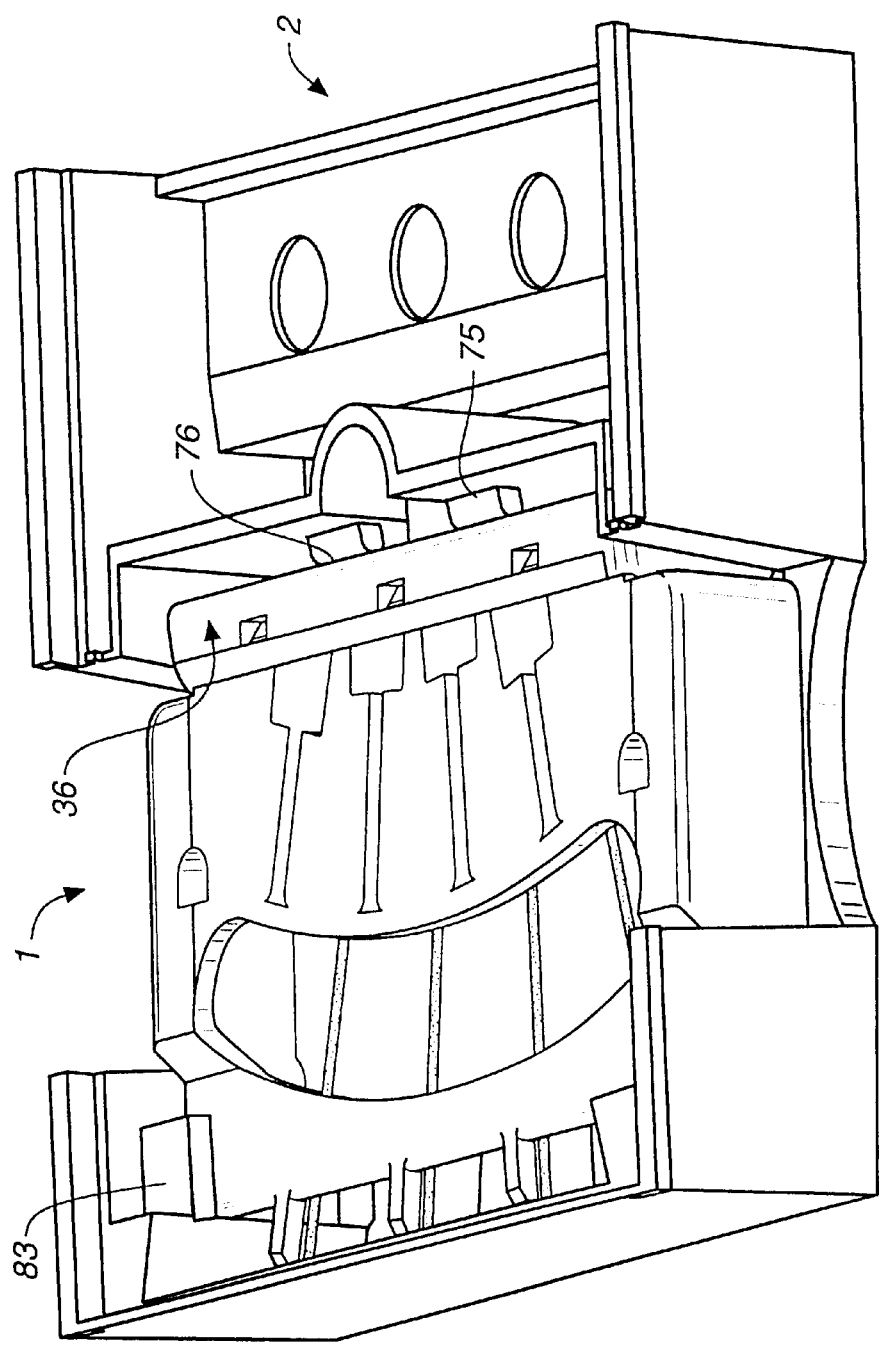
FIG._2

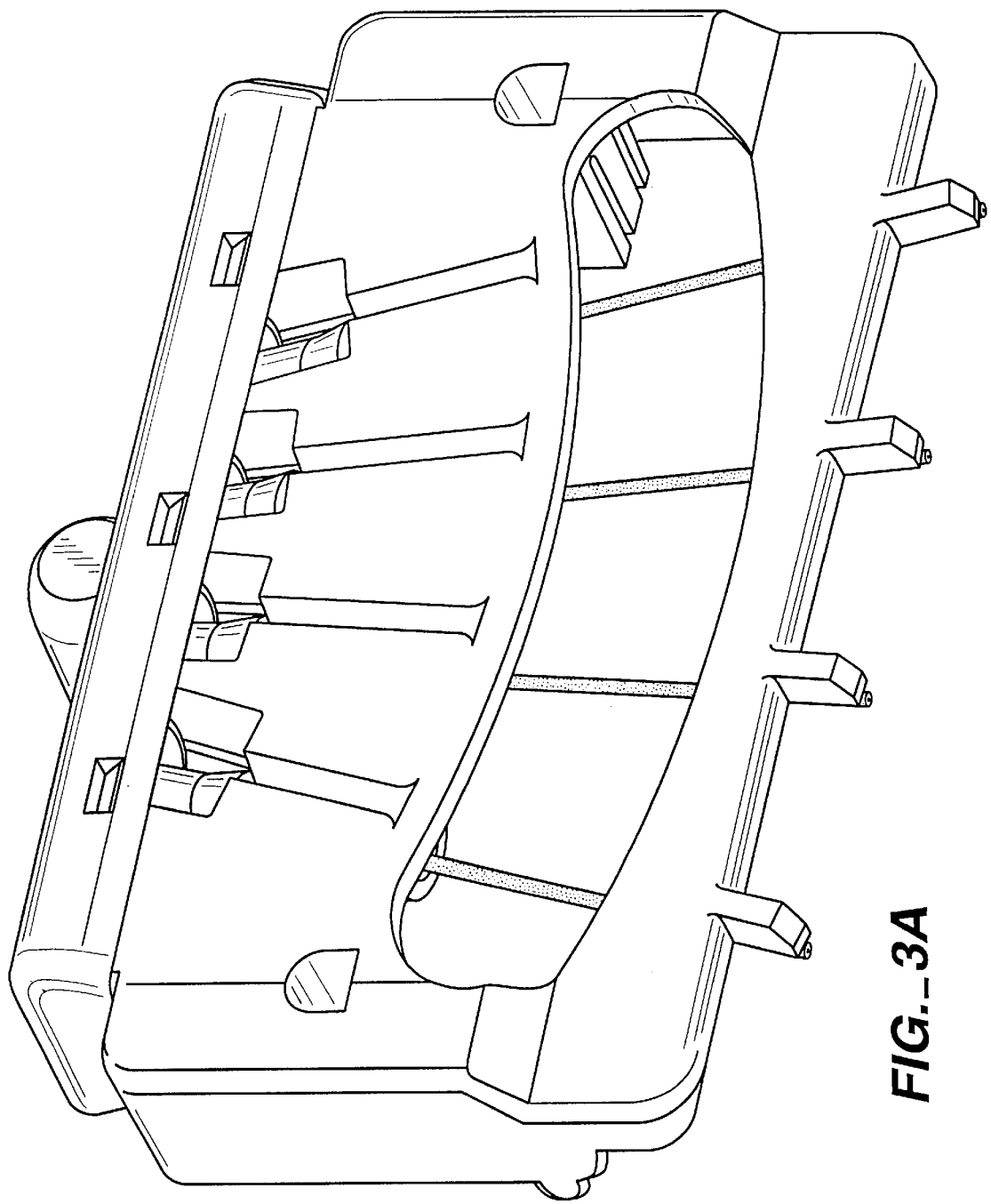
FIG._3A

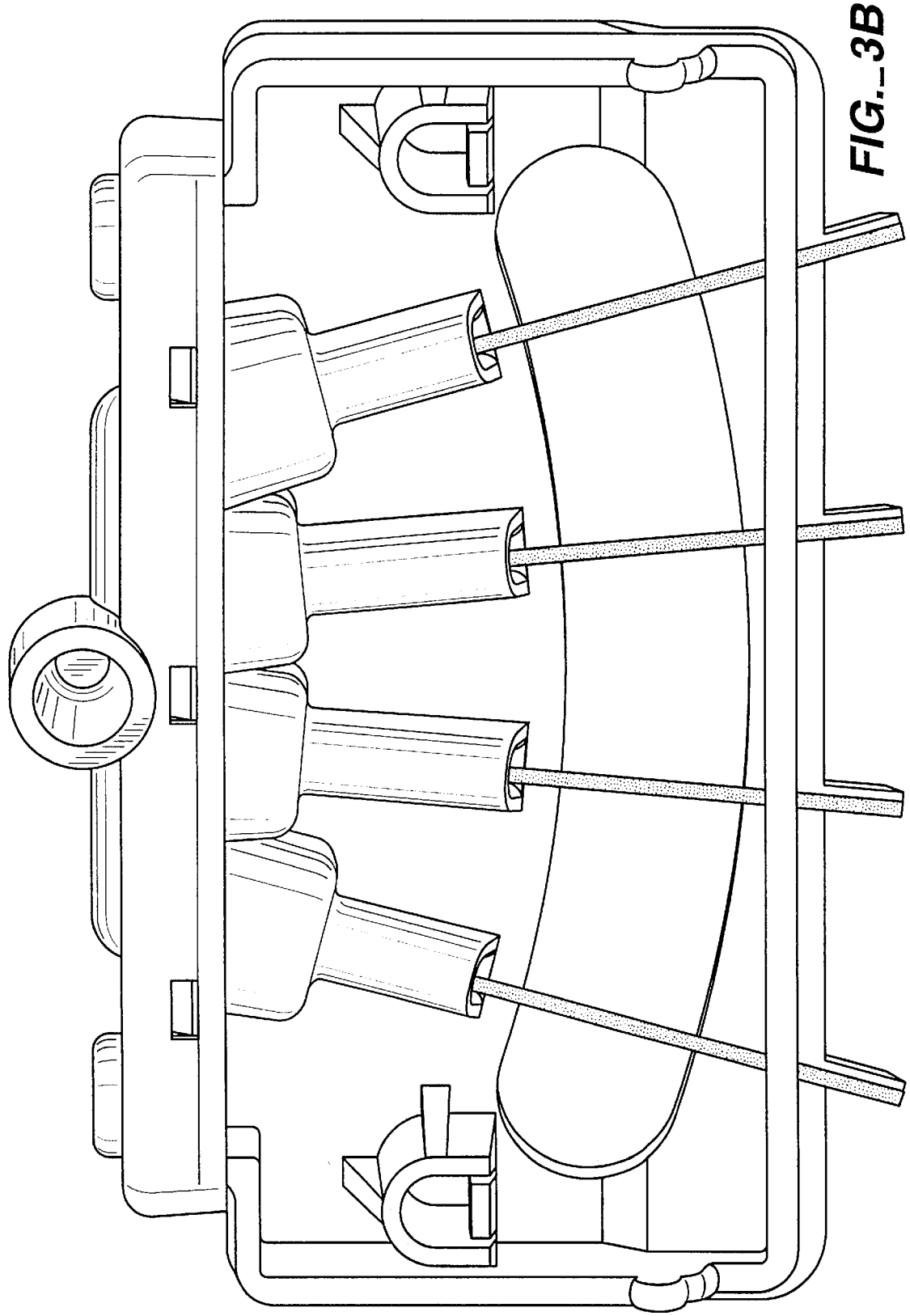

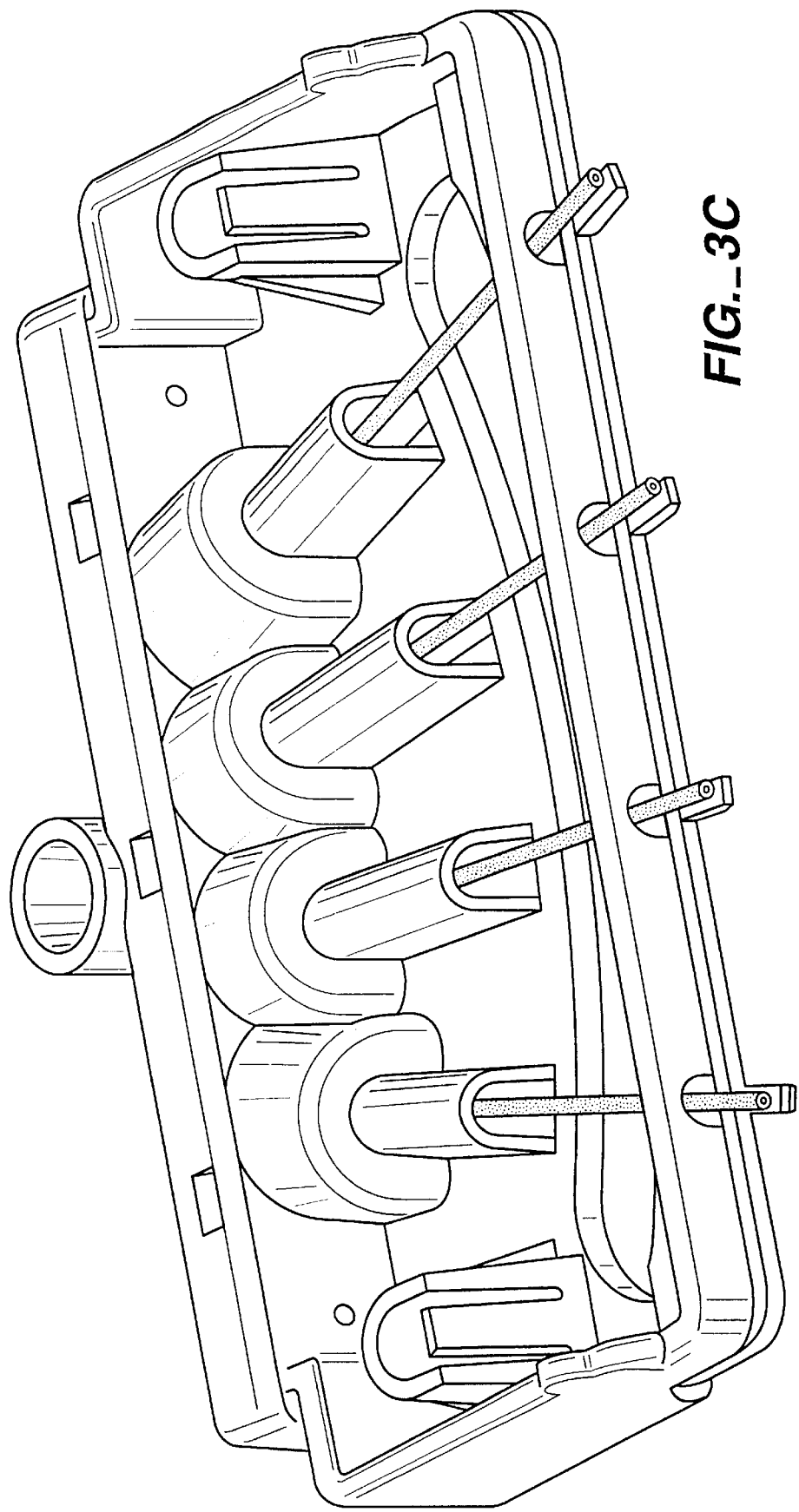
FIG._3C

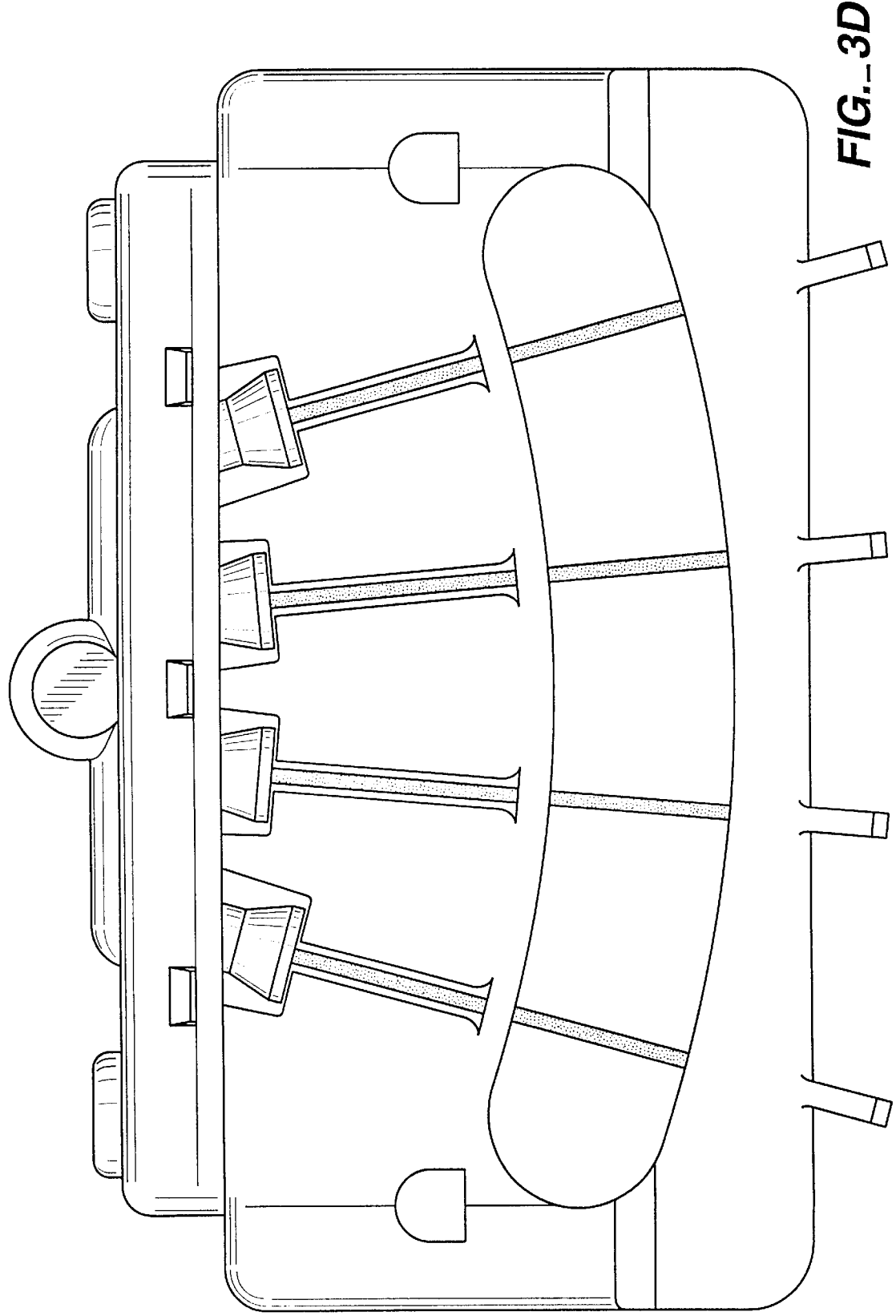
FIG._3D

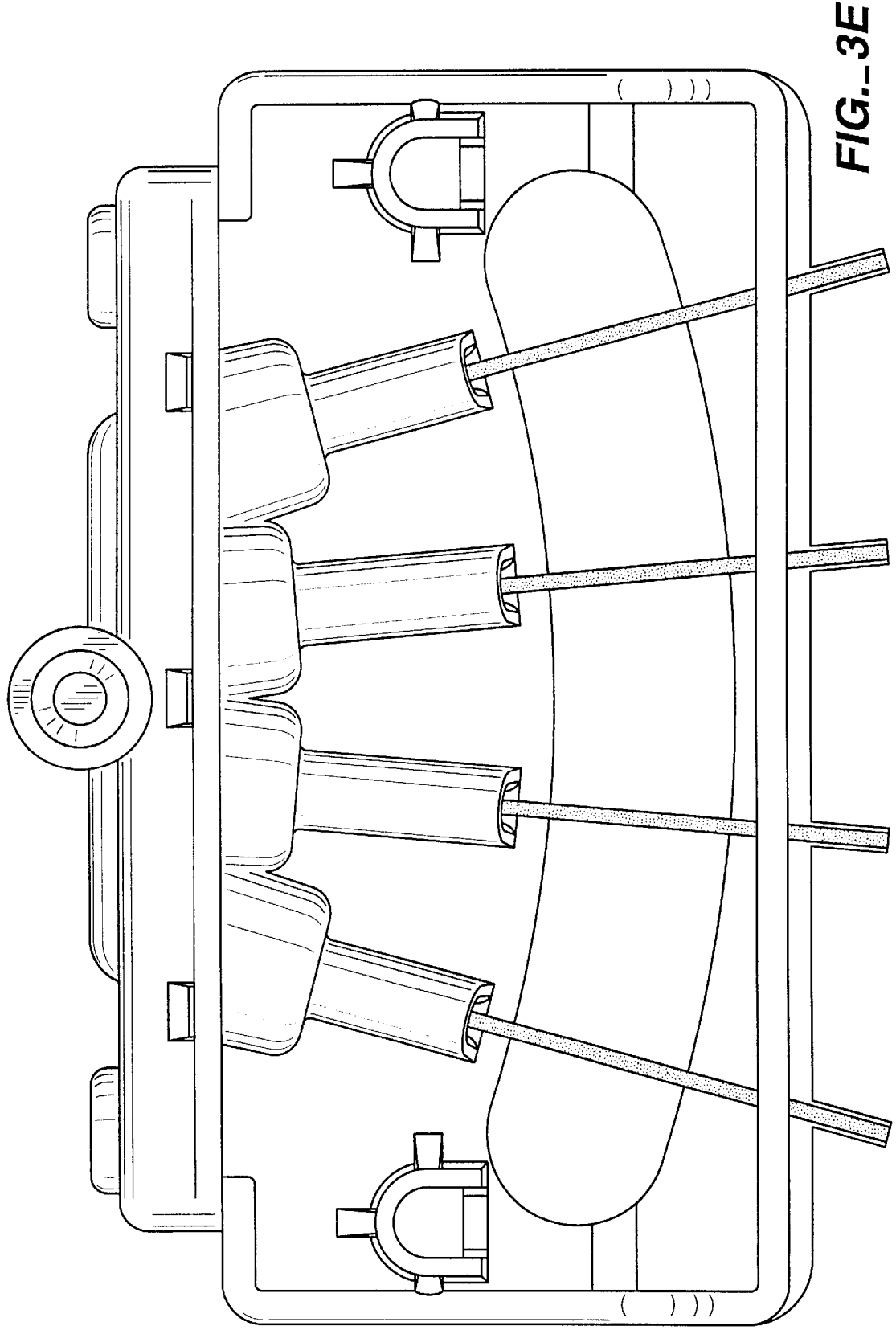
FIG._3E

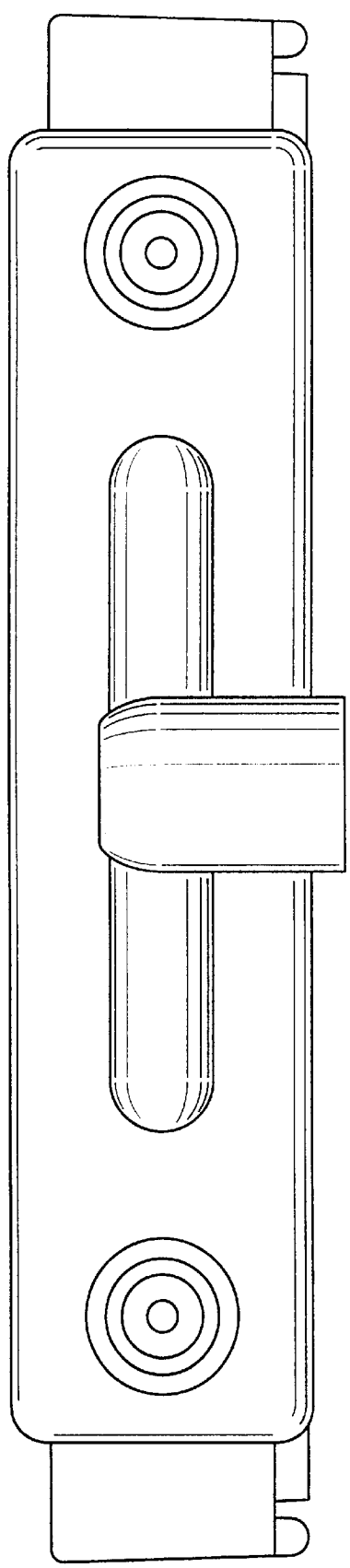
FIG._3F
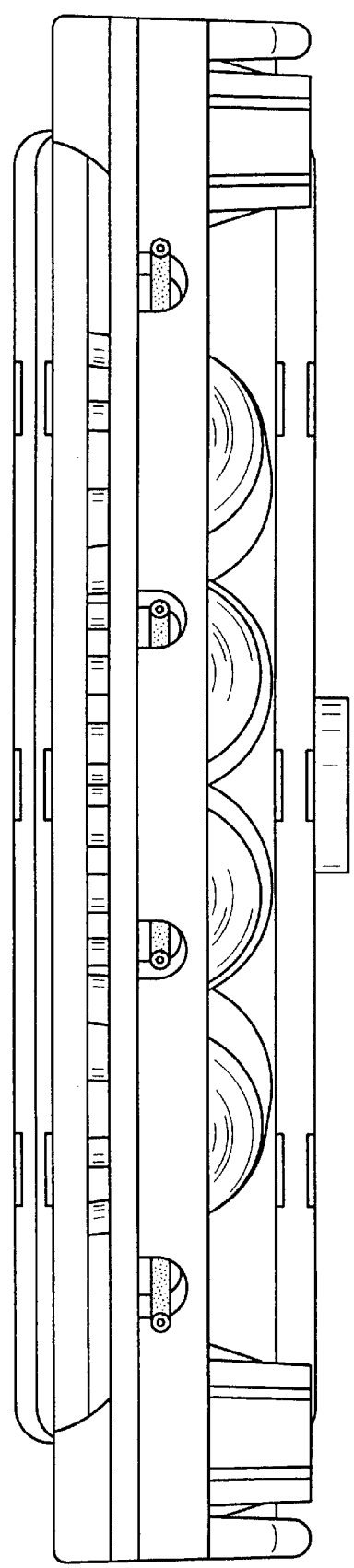
FIG._3G

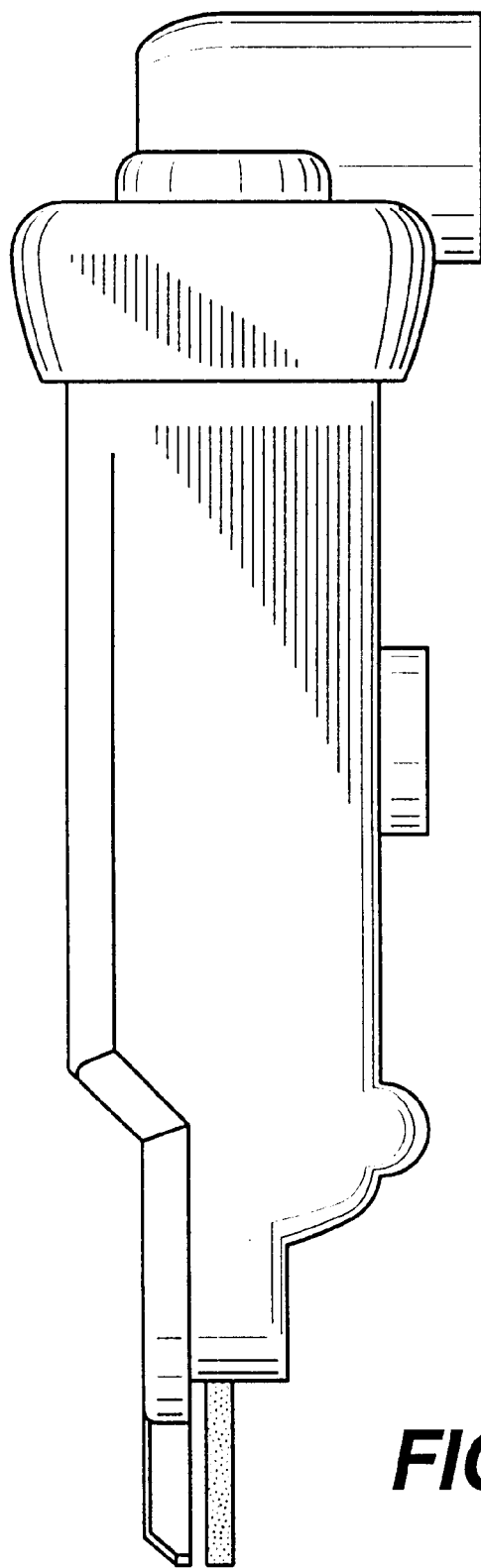
FIG._3H

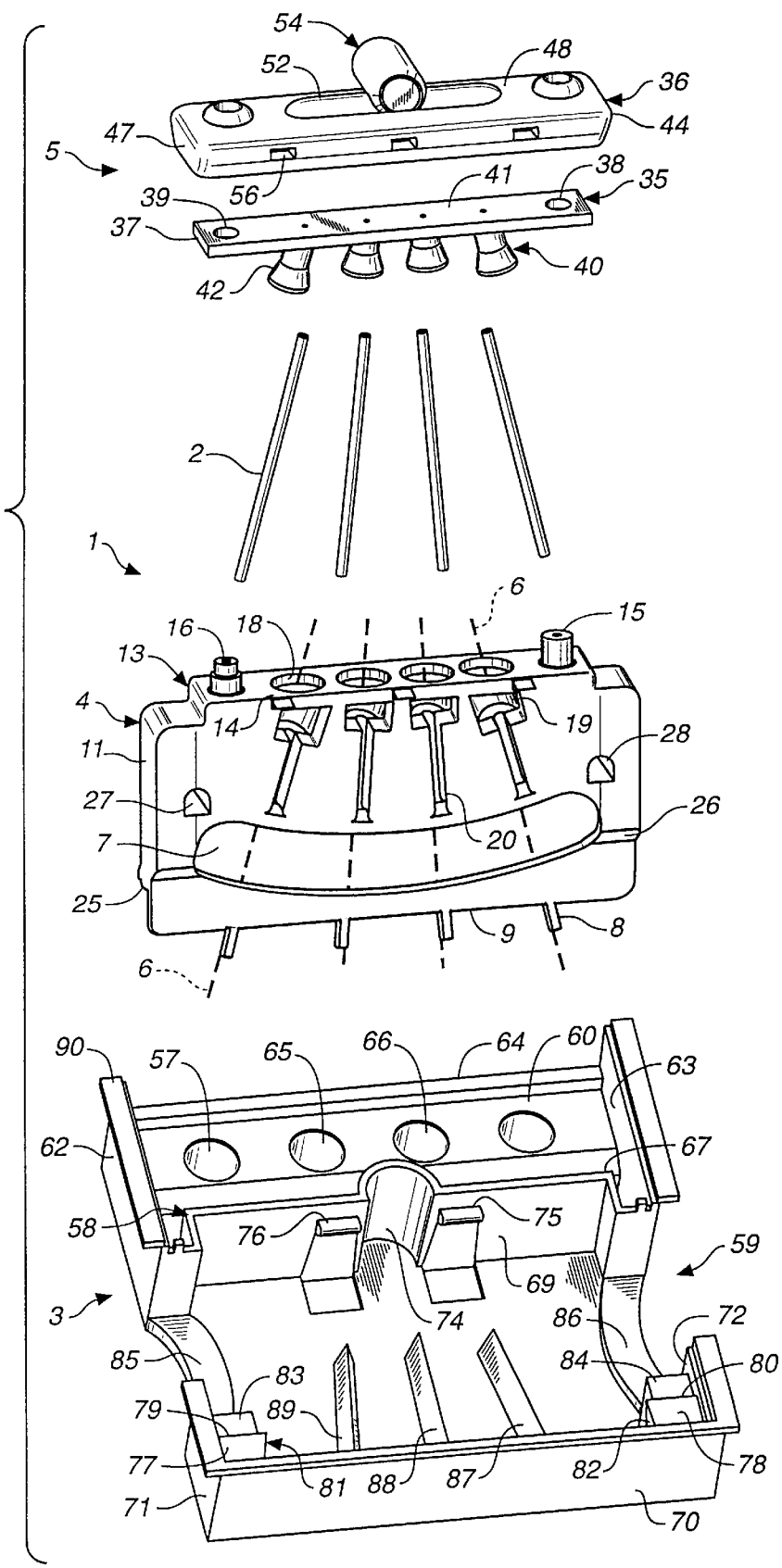

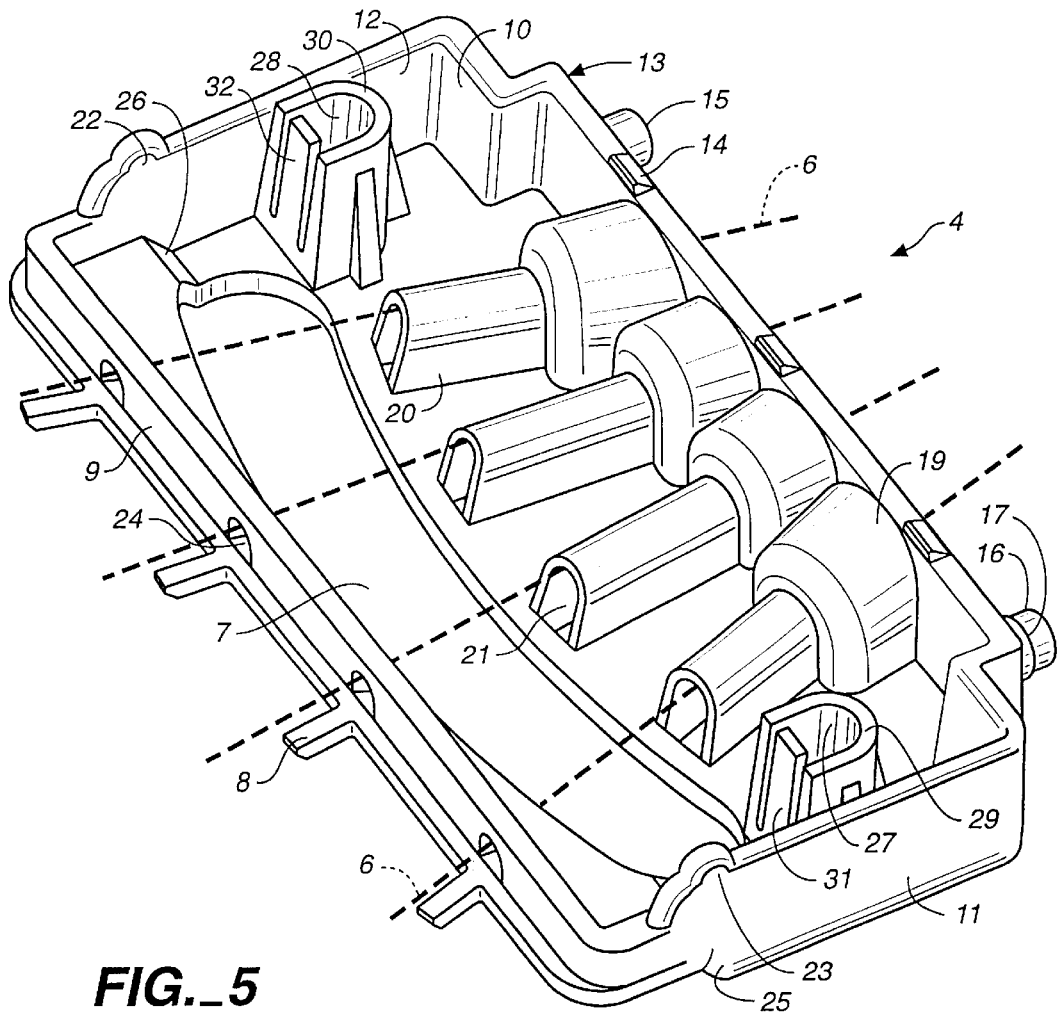
FIG._5

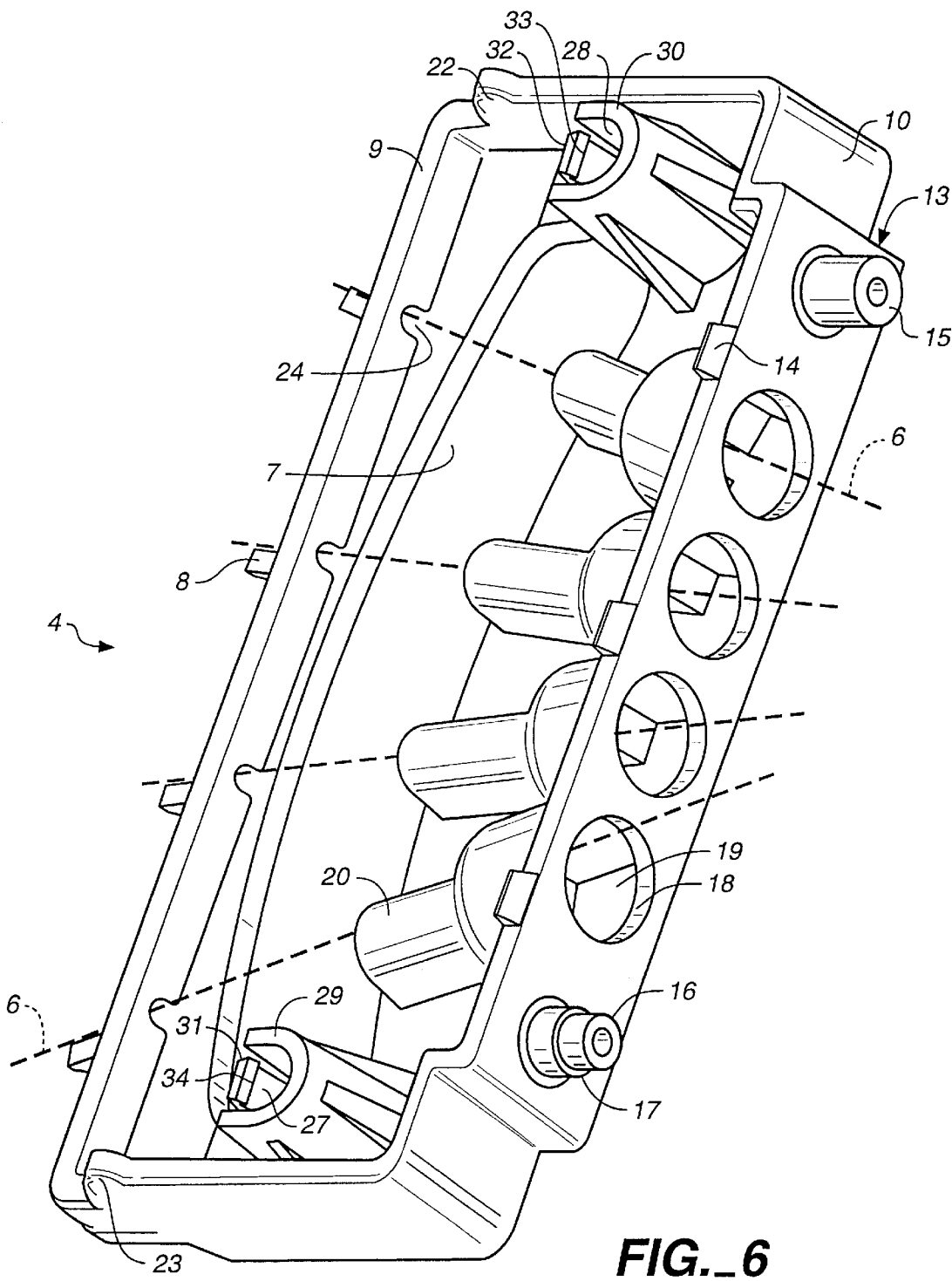
FIG._6

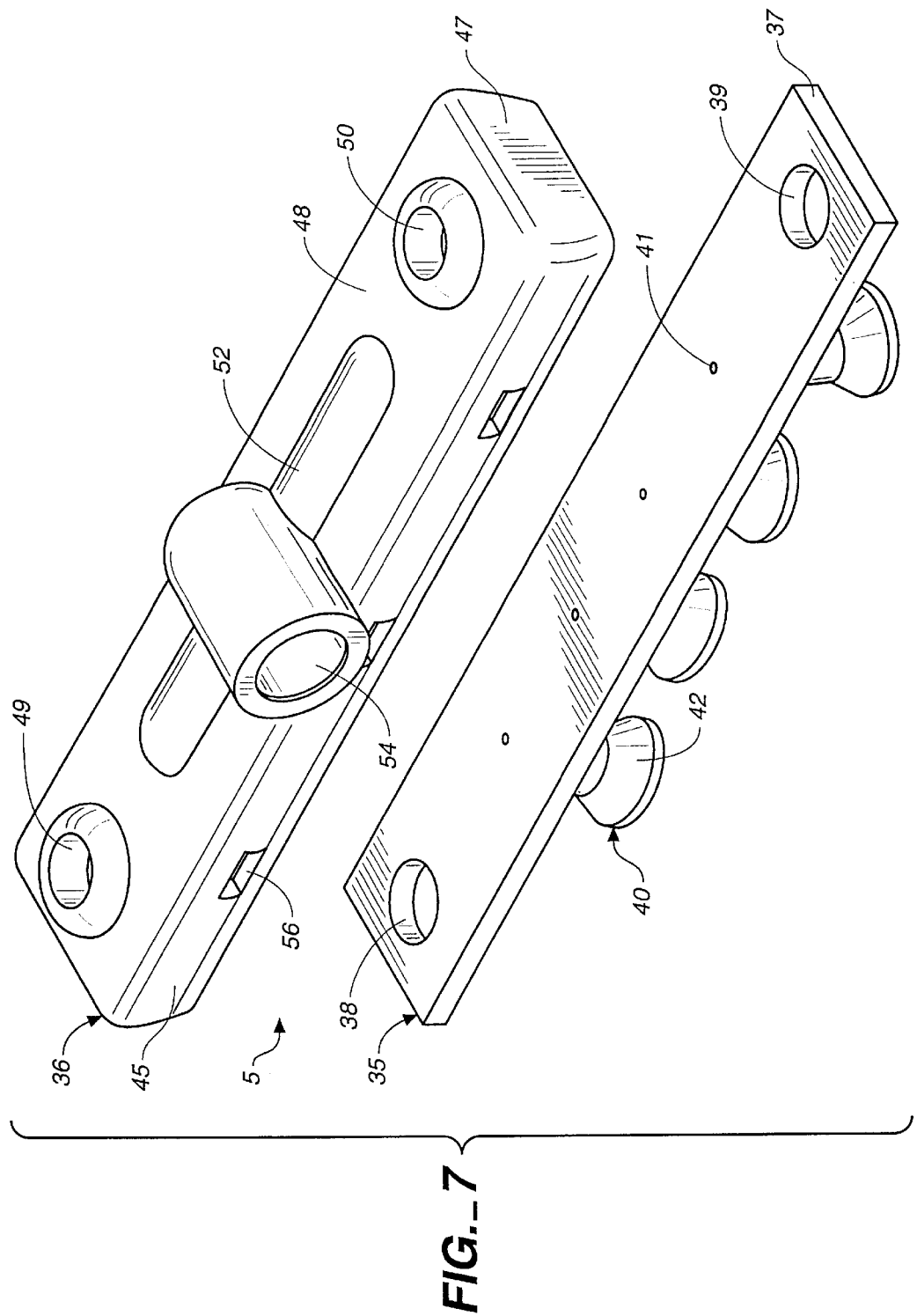
FIG._7

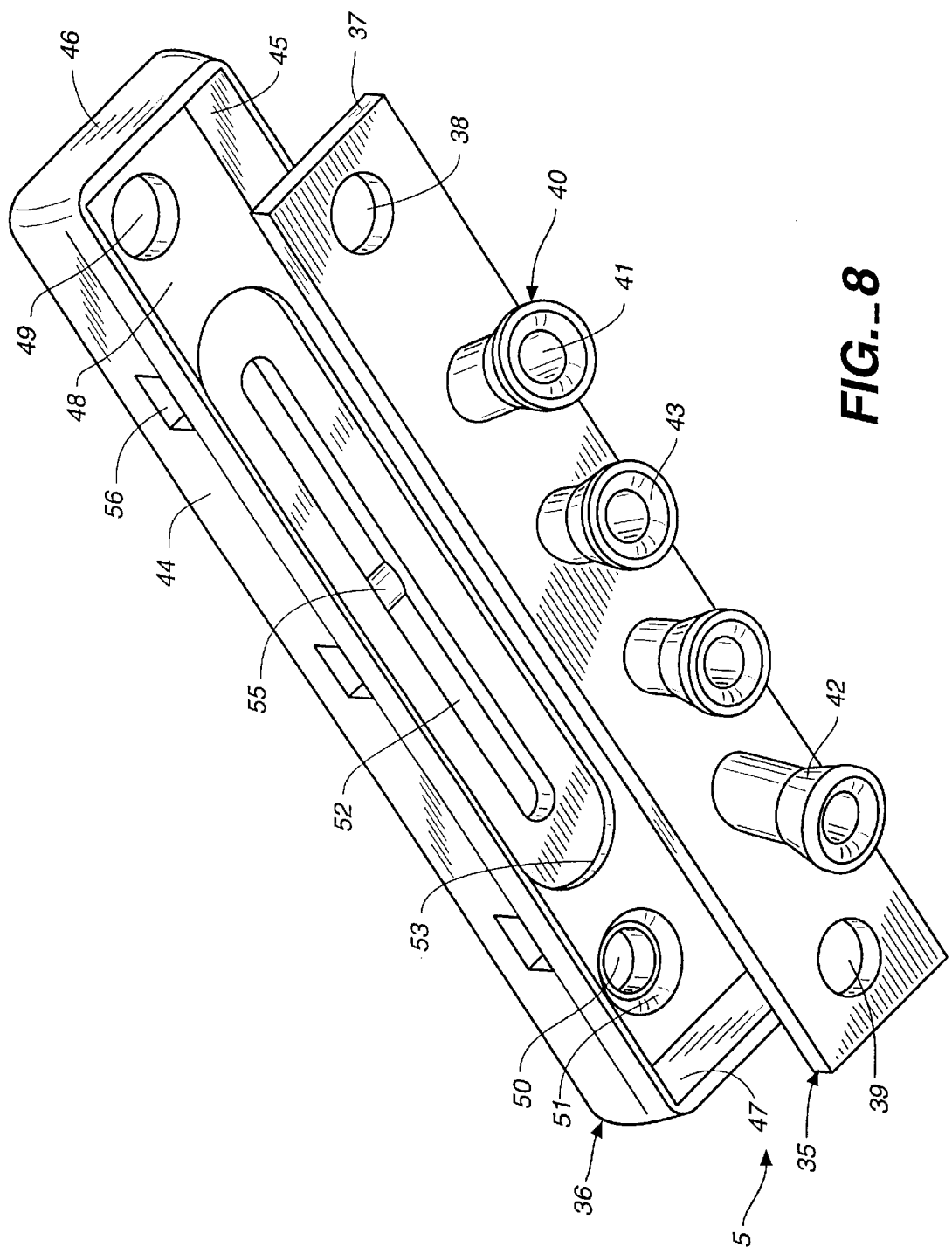
FIG._8

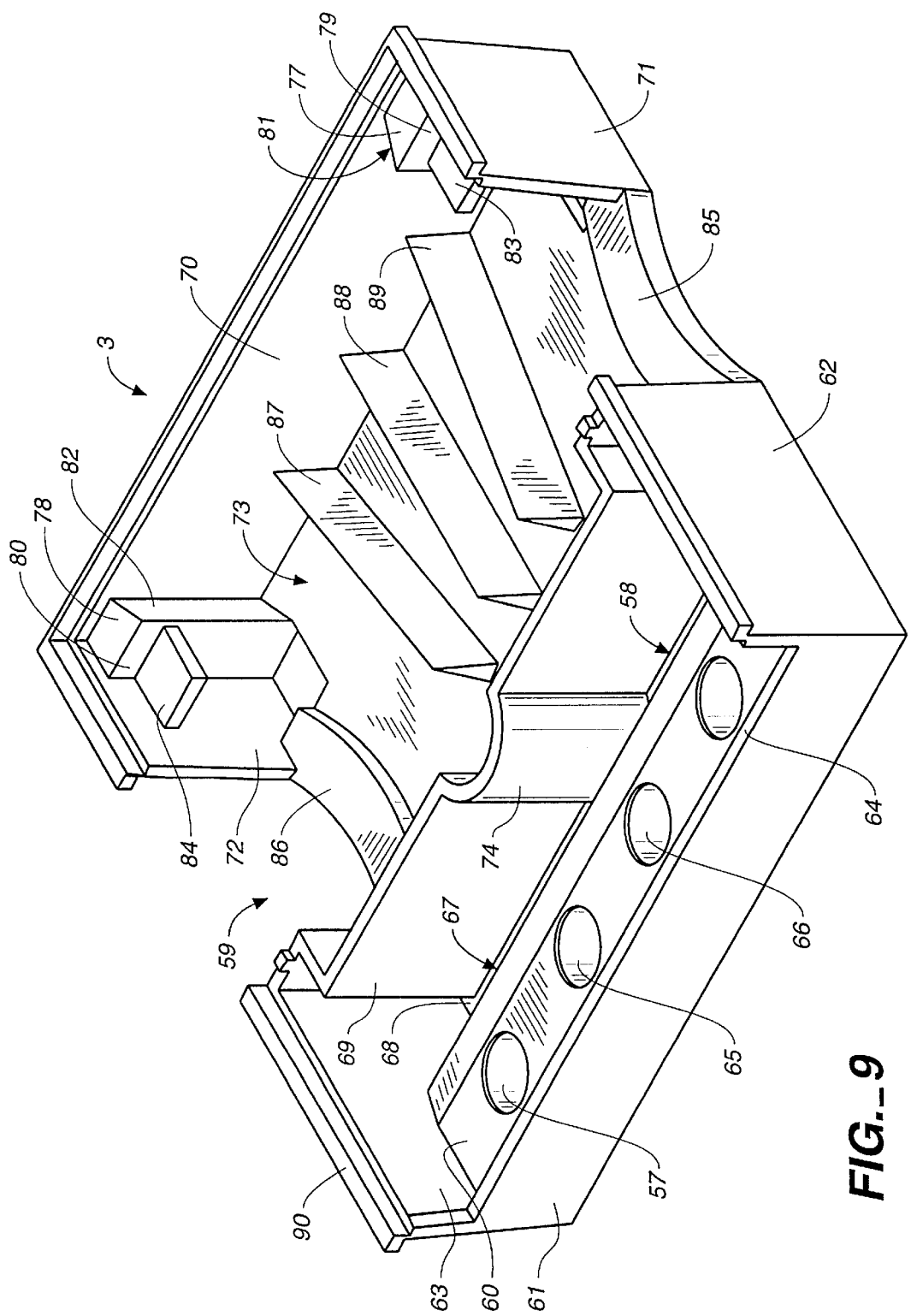
FIG._9

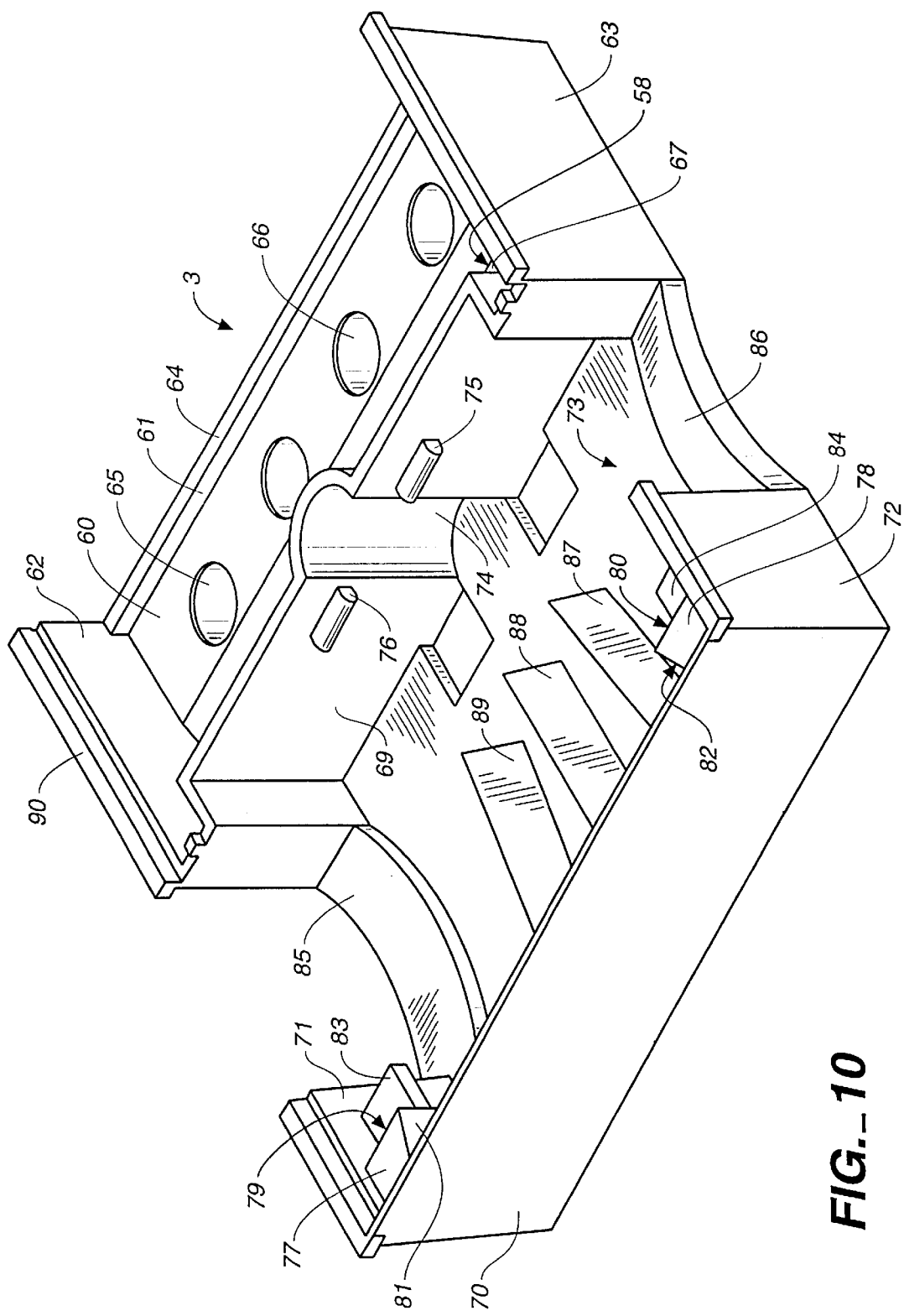
FIG._10

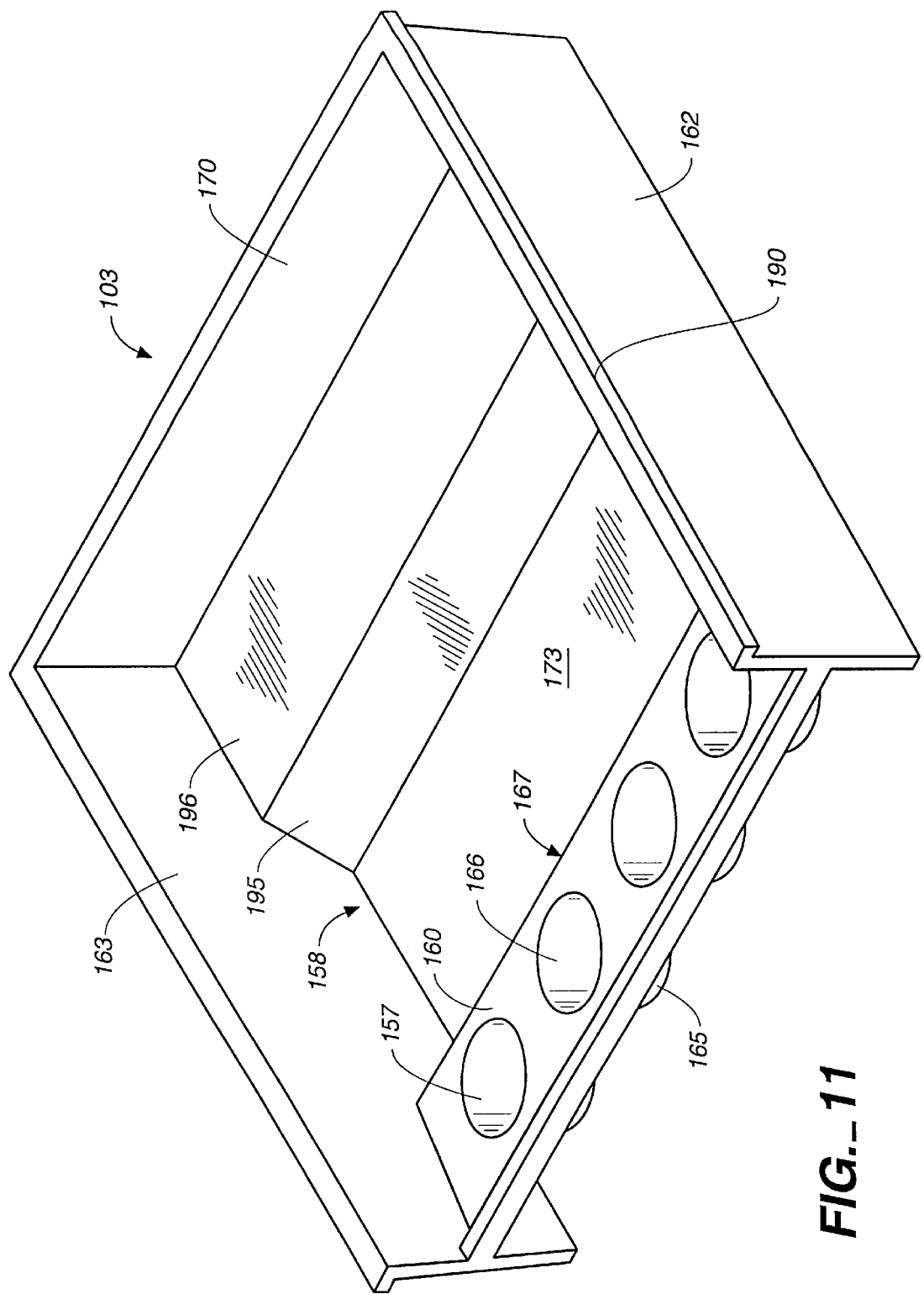
FIG._11

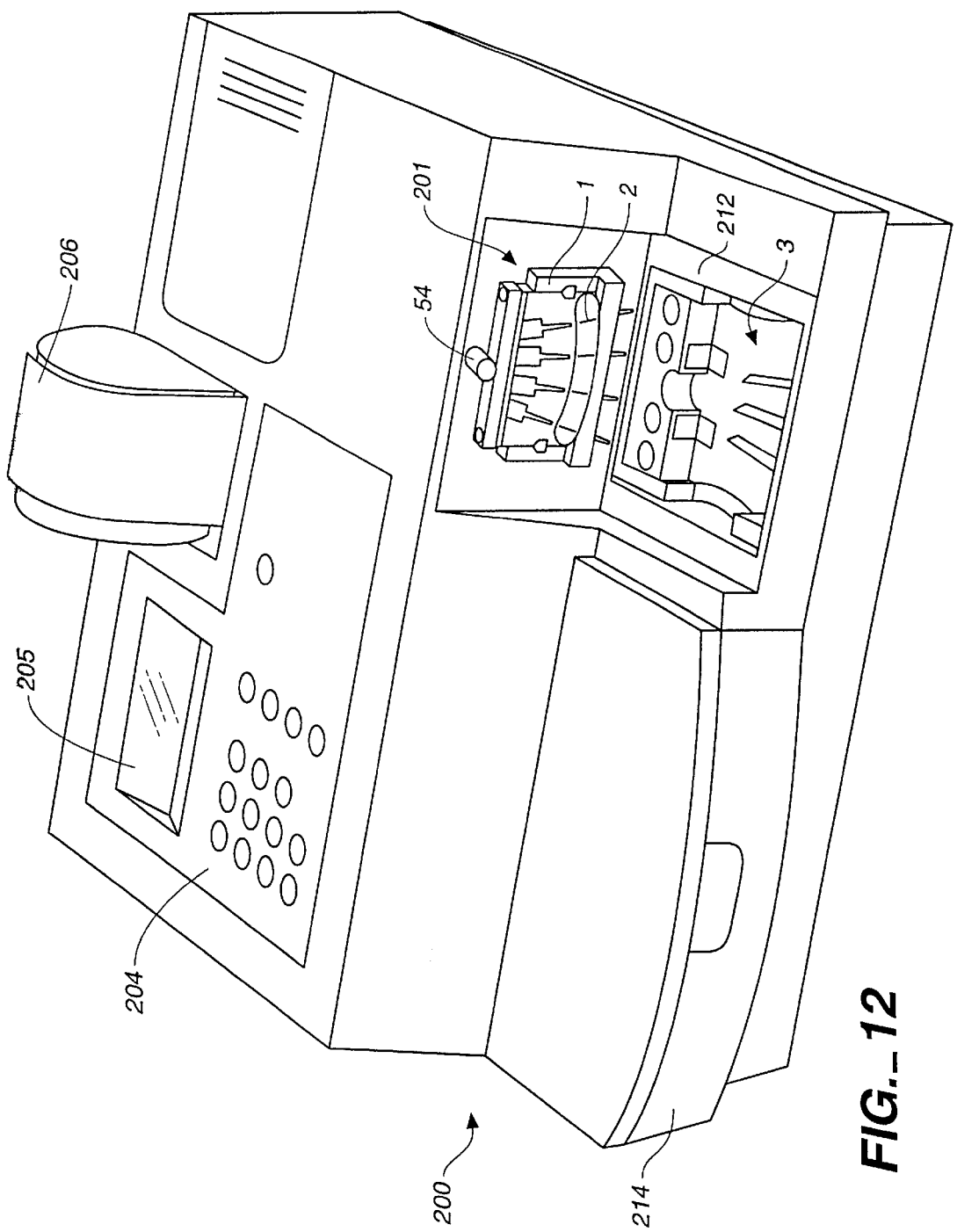
FIG._12

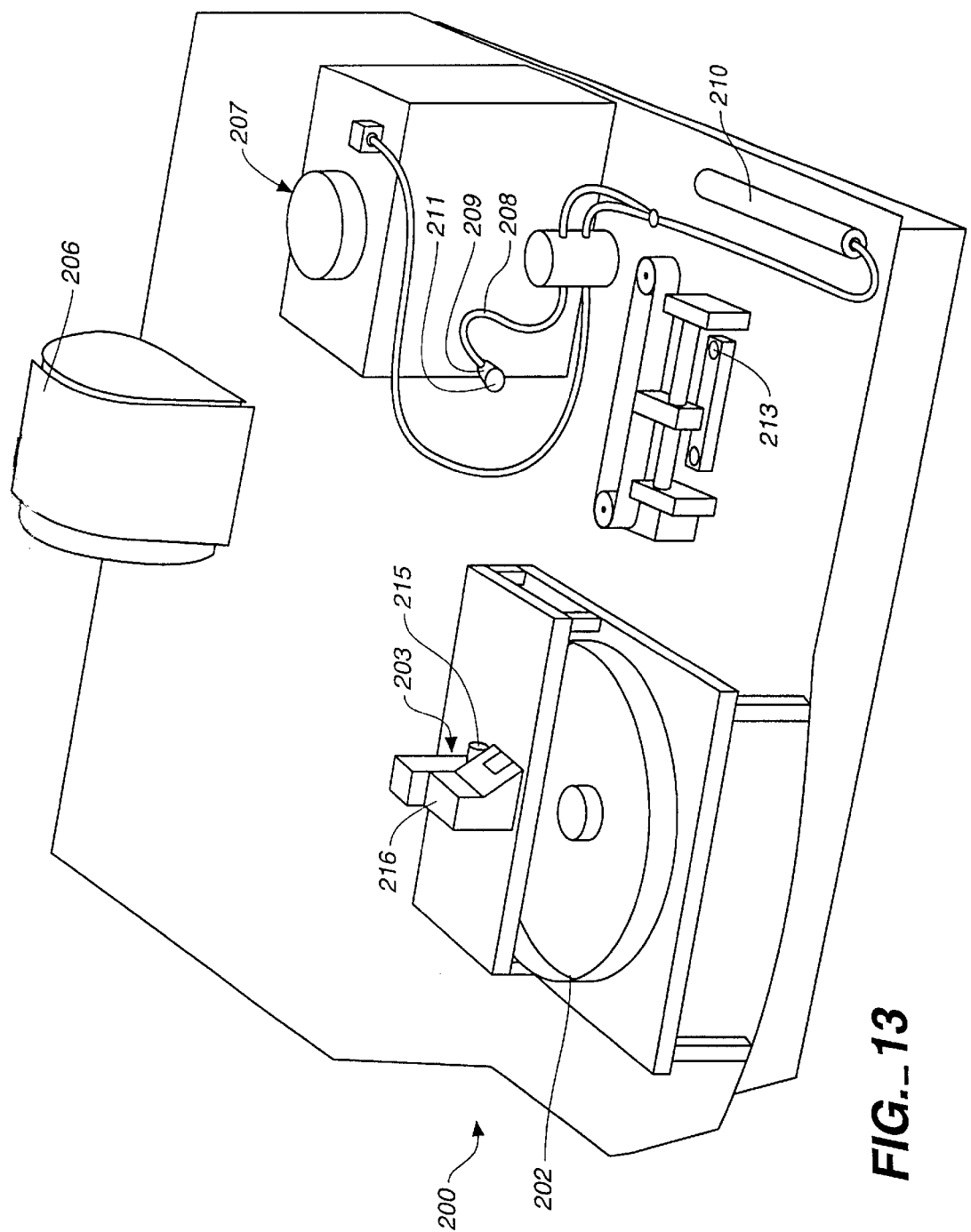
FIG._13

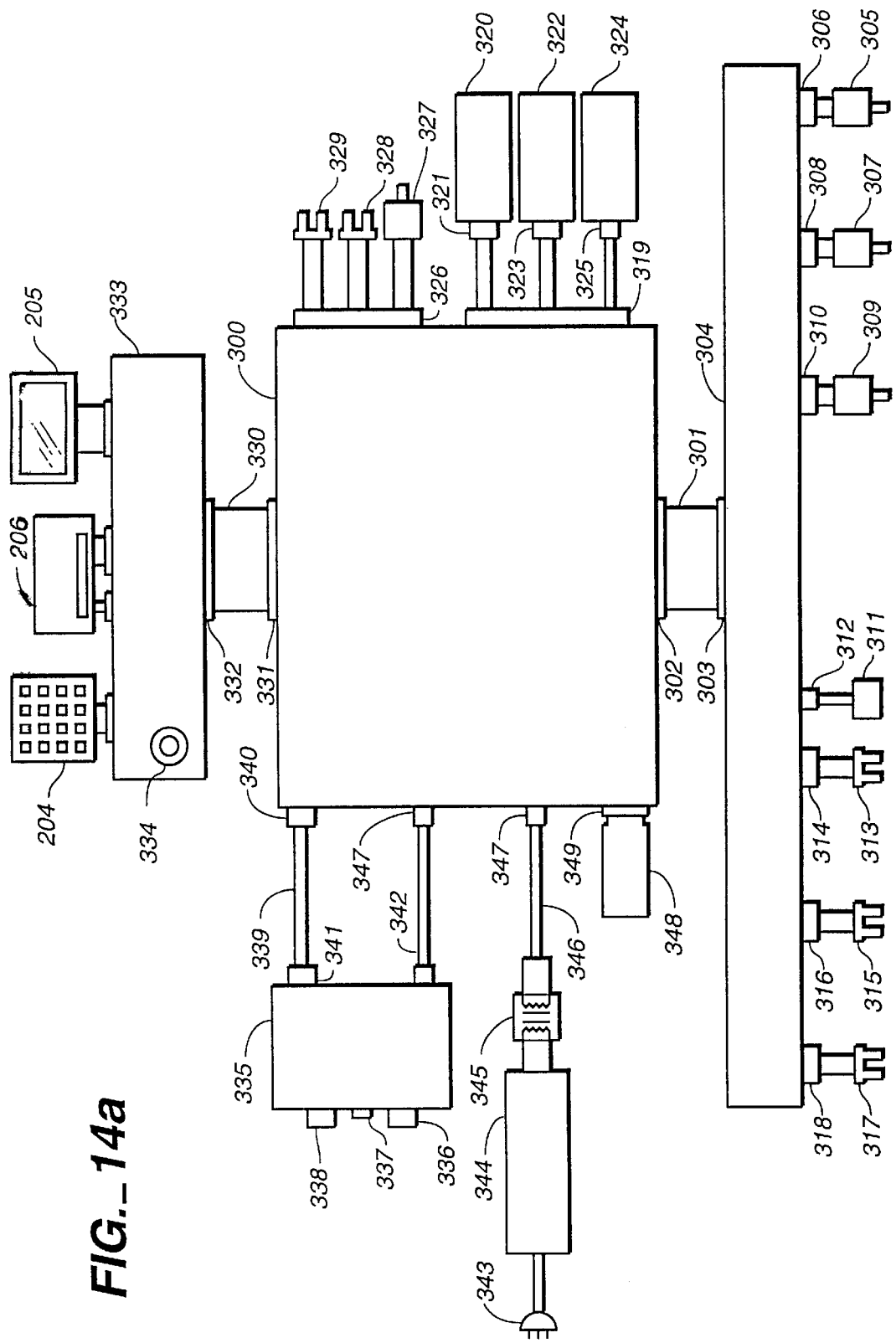
FIG._14a

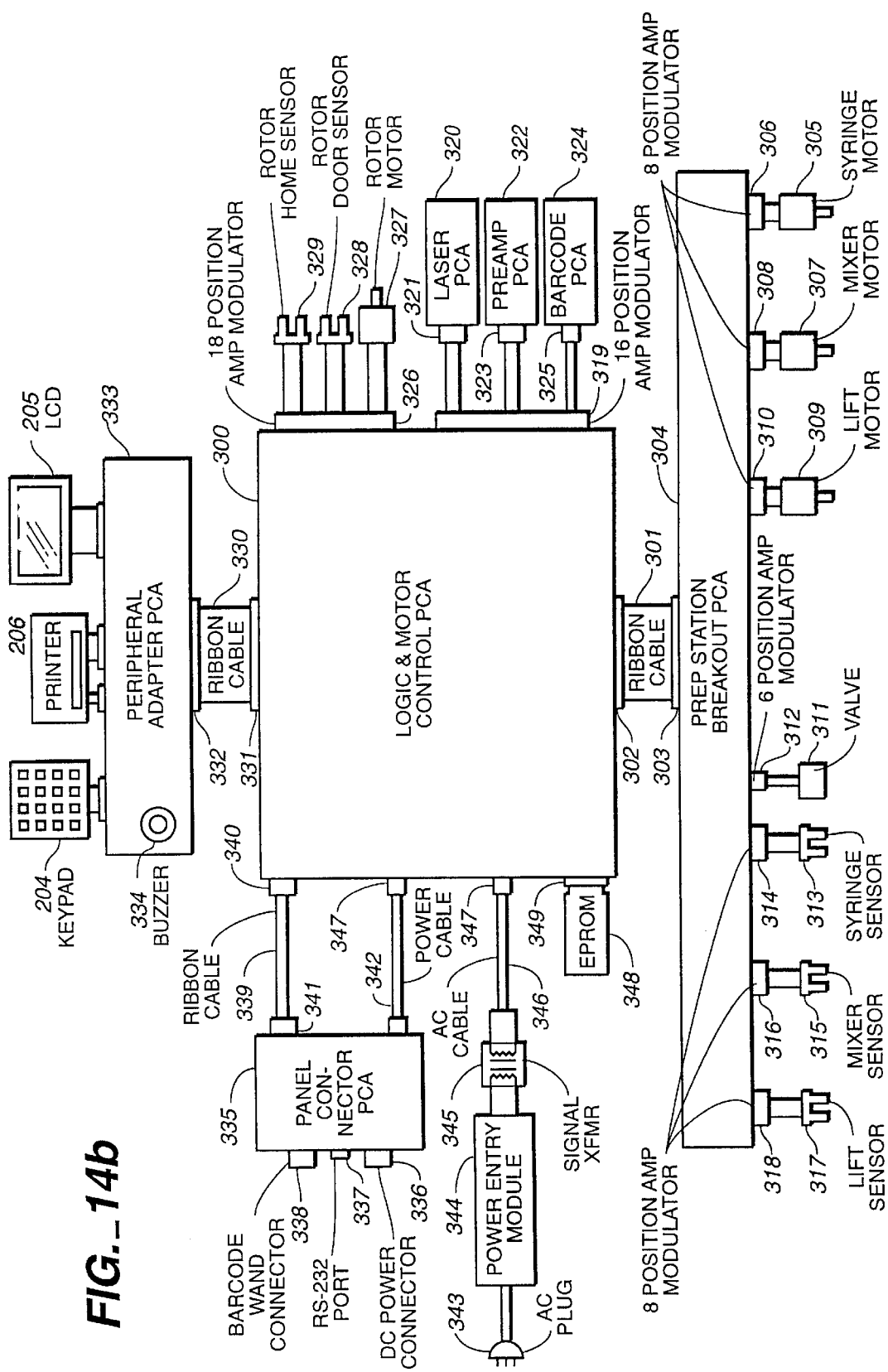
FIG._14b

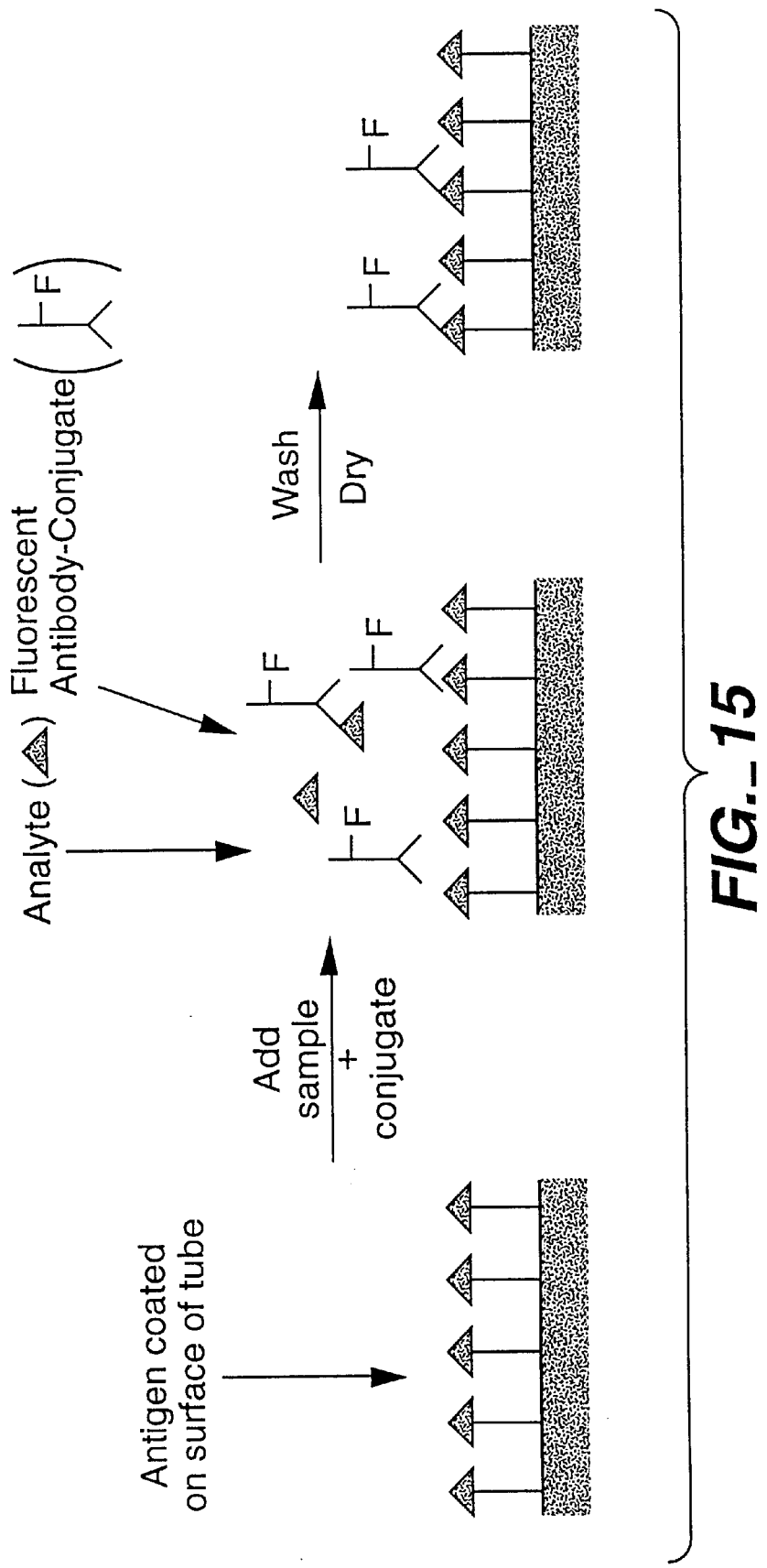
FIG._15

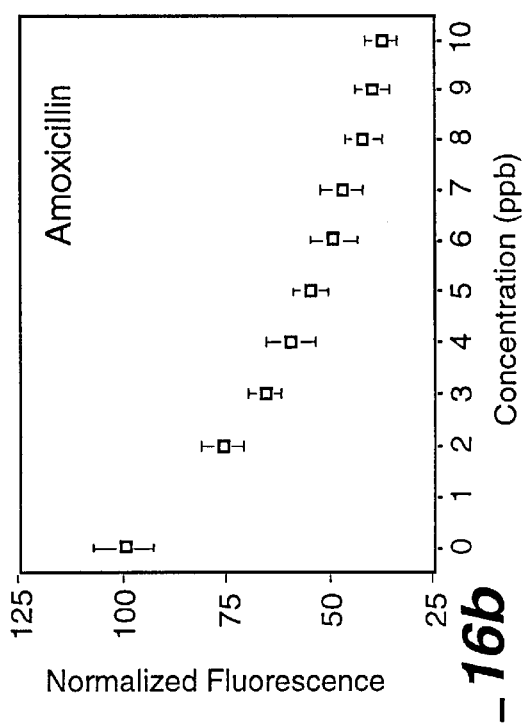
FIG._16b
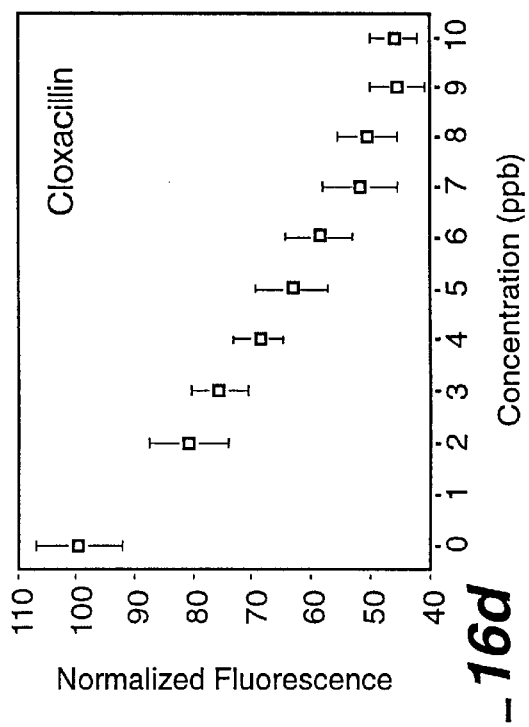
FIG._16d
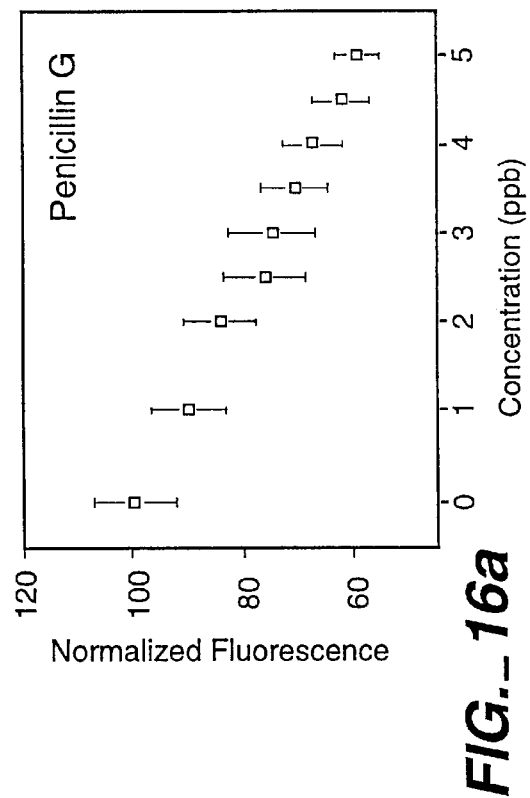
FIG._16a
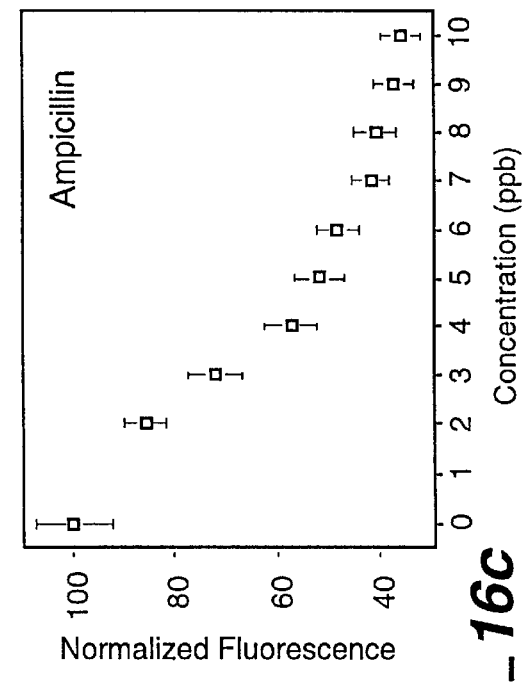
FIG._16c

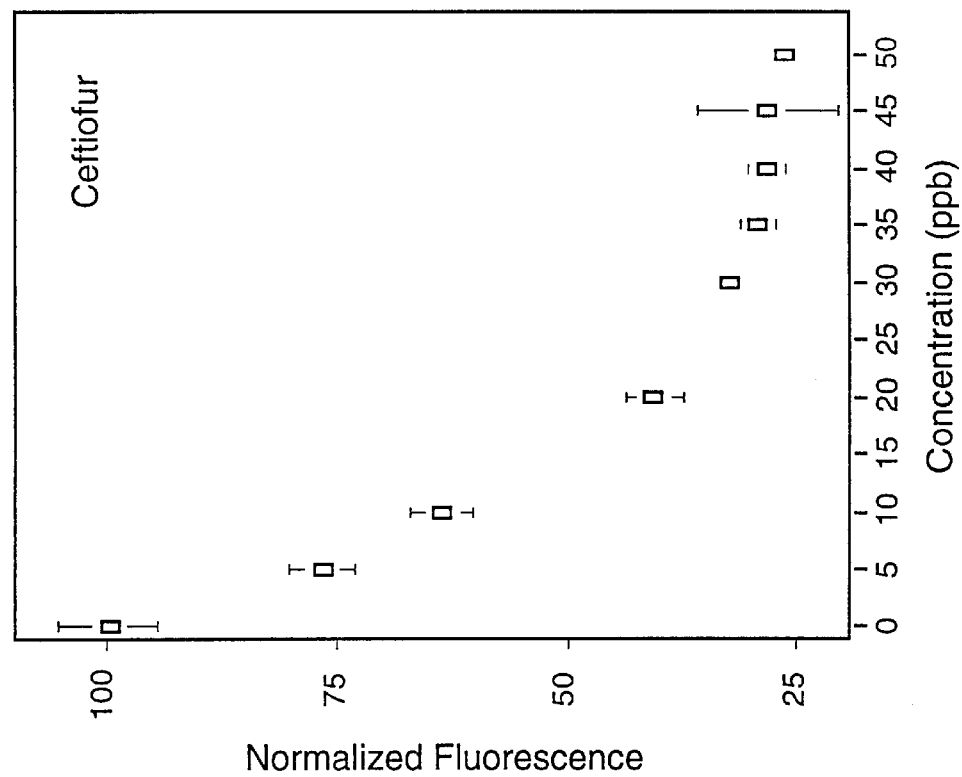
FIG._17b
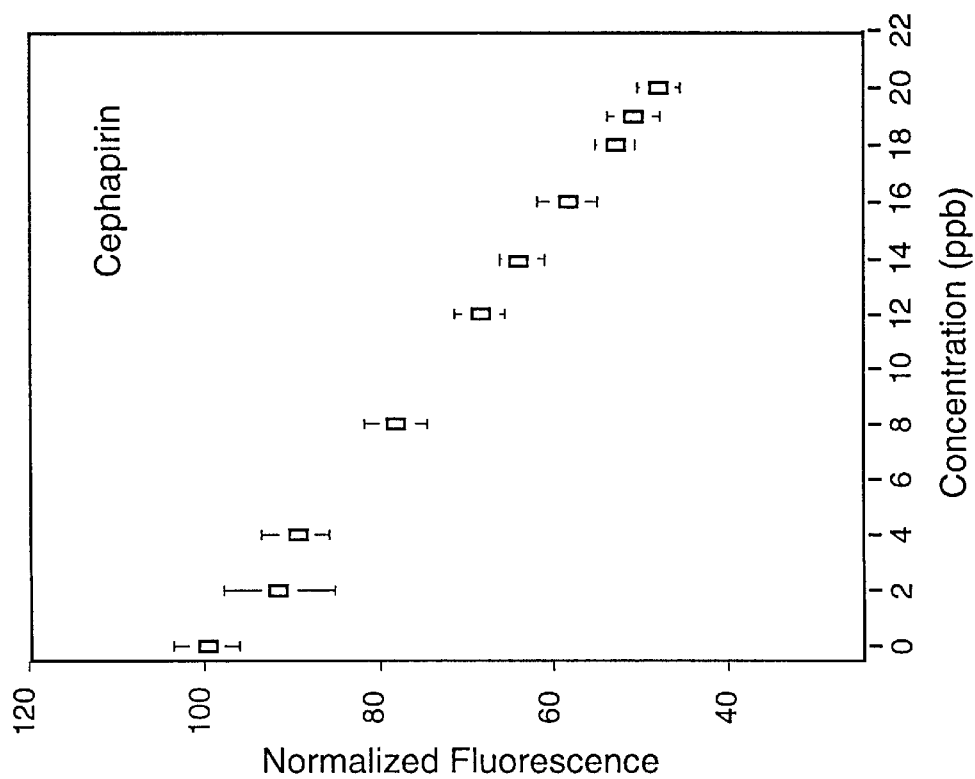
FIG._17a

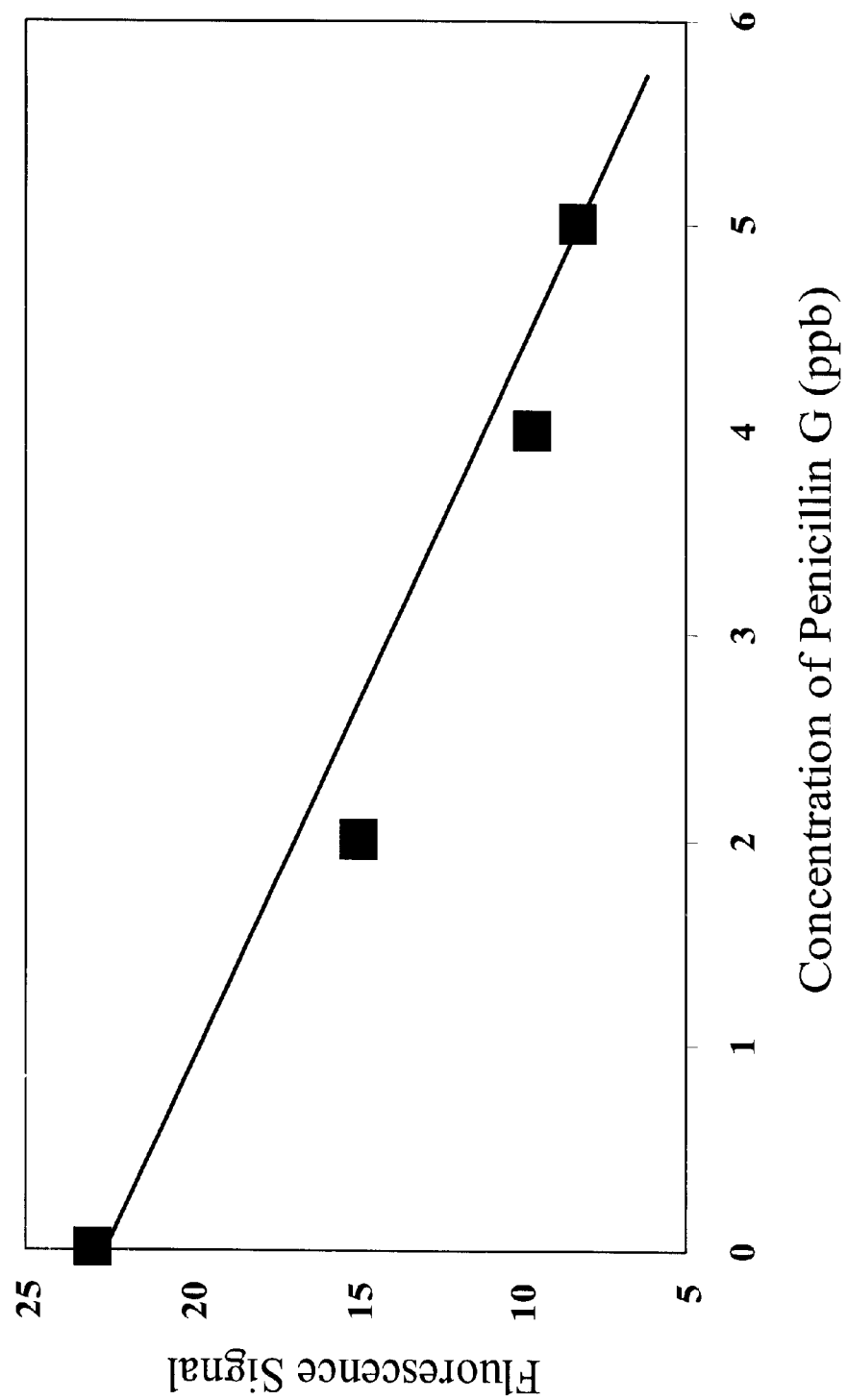
FIG._18

IMMUNOASSAYS IN CAPILLARY TUBES

CROSS-REFERENCE

"This is a divisional of co-pending U.S. Patent Application Ser. No. 08/688,043, filed Jul. 29, 1996, now U.S. Pat No. 5,976,896, which is a continuation-in-part of U.S. Patent Application Ser. No. 08/254,032, filed Jun. 6, 1994, now U.S. Pat. No. 5,624,850, which application is incorporated herein by reference in its entirety."

BACKGROUND

1. Field of the Invention

This invention relates generally to immunoassays (particularly solid-phase fluorescent immunoassays—SPFIAs), to devices for detecting analytes by immunoassay using capillary tubes, to an apparatus for use with such devices, and to manual, semi-automated, and automated, methods for such testing.

2. Background of the Invention

Many situations exist where qualitative, semi-quantitative, or quantitative detection of the presence of an analyte in a sample is desired. Situations where analyte detection is desirable arise in diverse industries, including: 1) the health care industry, e.g., in clinical and diagnostic medicine (e.g., in vitro analysis); 2) the food processing and chemical industries, e.g. in quality control for food production; and 3) the environmental control industry, e.g. monitoring for the presence of various pollutants in air, ground water, or soil.

Many assays using unique devices and protocols to detect the presence of analytes through chemical and physical means have been developed. Immunoassays make up one broad field of assays which find use in the detection of analytes. In immunoassays, the occurrence of binding events between specific binding pair members is used as an indication of the presence of analyte in the sample. Benefits of using immunoassays, as compared to non-immunoassays, in analyte detection include high sensitivity, high specificity, reliability, and relatively short assay times.

The binding events that are utilized in immunoassays often occur at the surface of a solid support with one binding member held at the surface of the solid support and the other binding member in the sample. The time required for a particular immunoassay to be completed will depend on the ability of the binding member in the sample to reach and bind to the member on the support surface. The ability of the binding member in the sample to bind with its pair on the support surface is dependent on many factors; such factors include the concentration of the binding member on the support surface, and the surface to volume ratio of the sample/support combination. One method to decrease the time required for an immunoassay is to increase the concentration of a binding member on a support surface. Another approach is to increase the ratio of the surface area of the support relative to the volume of the sample to be assayed.

Common immunoassays include radio immunoassays (RIA), enzyme-linked immunosorbent assays (ELISA), and membrane based assays, such as common home pregnancy tests. These immunoassays have several disadvantages. A significant disadvantage of RIA is the requirement for the use of hazardous radioactive isotopes. A disadvantage of ELISA is the numerous steps of sample addition, incubation, washing, addition of color reagent, addition of stop reagent, and reading required to perform the assay; such manipulations can be especially troublesome and a source of significant error in the field. Also, enzyme reactions tend to be temperature sensitive, which require temperature control. Unlike RIA, in an which the label is directly detected, in an ELISA the enzyme label is not directly detected. Instead, one must allow for a detectable product to be produced. Further, ELISA protocols may not be suited for all assays on all types of liquids, such as where the liquid comprising the analyte of interest contains contaminants which interfere with one or more individual steps in the assay, e.g. enzyme activity, detectability of enzyme product, and the like. Additionally, the safety concerns with RIA and the complexity of ELISA typically require that they be performed by relatively highly trained personnel and further require constant monitoring by or interaction with the trained operator. A disadvantage with membrane based assays is that they often provide poor quantitation and sensitivity. Many of these assays also require long incubation times, typically in the tens of minutes to hours, making analysis of multiple-samples time consuming and expensive.

Nevertheless, ELISA is a commonly used format. In ELISA, binding events of interest are detected through the appearance of detectable product produced by an enzyme acting on a substrate. The formation of the detectable product can be amplified to the extent required by increasing the concentration of the substrate and/or increasing the reaction time. On this basis, there is an opportunity to greatly increase the signal when only a few enzymes becoming bound.

Conventionally, ELISA has been conducted in microtiter plates consisting of wells. In an effort to improve performance, ELISA has been demonstrated in capillary tubes. With ELISA immunoassays conducted in capillary tubes, rapid quantitative results are reported. At least one reported ELISA is described as sensitive and able to detect small amounts of analyte. See e.g. Chandler et. al., "A new enzyme immunoassay system suitable for field use and its application in a snake venom detection kit" Clinica Chimica Acta, 121:225–230 (1982). However, the aforementioned disadvantages inherent in ELISA still exist.

Additionally, while ELISA assays have been performed in capillary tubes in the laboratory, no successful products have been developed. A primary reason for this is the difficulty of bringing several solutions into and out of the capillary tubes and the ability to effectively read the result.

Therefore, there is a significant need for a fast, reliable, accurate immunoassay that requires minimal interaction with the operator. There is also a need for an immunoassay that can screen several similar or different samples sequentially or simultaneously for the same analyte or which can screen for different analytes in the same sample or in a plurality of aliquots of the same sample.

OBJECTS OF THE INVENTION

An object of this invention is to provide a simple, semi-automated method for detecting and quantifying an analyte in a sample.

It is a further object of this invention to provide a solid-phase fluorescence immunoassay (SPFIA) that has fewer manipulations than a comparable enzyme-linked immunosorbent assay (ELISA) for detecting an analyte in a sample.

A further object of this invention is to provide a rapid SPFIA that independently and semi-quantitatively or quantitatively assays for a plurality of analytes from a plurality of samples or aliquots from the same sample.

A further object of this invention is to provide a reliable SPFIA that requires minimal manipulation of equipment by an operator performing the immunoassay.

A still further object of this invention is to provide aSPFIA that independently and semi-quantitatively or quantitatively assays for a plurality of analytes from a plurality of samples in less than about 5 minutes.

A still further object of this invention is to provide a unique capillary tube suitable to be used to achieve the aforementioned objects of this invention.

A still further object of this invention is to provide a method for preparing a capillary tube to be used to achieve the aforementioned objects of this invention.

A still further object of this invention is to provide a uniquely-designed cartridge for carrying at least one capillary tube (and preferably more than one) that can be used to achieve the aforementioned objects of this invention.

A still further object of this invention is to provide a tray having a reservoir and a plurality of wells for holding a plurality of aliquots of a sample, which tray can be used in conjunction with the cartridge-held capillary tubes to assist in achieving the aforementioned objects.

A still further object of this invention is to provide an apparatus to be used in conjunction with the cartridge-held capillary tubes and sample tray to perform the SPFIA of this invention and to further assist in achieving the aforementioned objects of this invention.

Other objects will be apparent to one of ordinary skill in the art upon reading the follow specification and claims.

SUMMARY

The present invention provides devices for screening for one or more analytes in a sample comprising capillary tubes, a cartridge, and a sample tray which can combine to form a portable and disposable testing kit, and an apparatus and process for screening for one or more analytes, and a method for preparing capillary tubes for use with the method for screening for one or more analytes, that are directed to the disadvantages of the prior art and address heretofore unmet needs previously discussed.

One aspect of the present invention is a cartridge for securely holding a plurality of spaced-apart capillary tubes. The cartridge comprises a frame for holding the tubes in a spaced-apart manner, wherein the frame has a pathway in which each capillary tube can be aligned; and at least one region in the frame to expose at least a portion of each capillary tube so that an electromagnetic signal can contact a portion of each tube.

Another aspect of the present invention is a tray for holding multiple portions of a sample. The tray comprises a reservoir sufficient to hold a quantity of fluid and a shelf extending substantially perpendicularly outward from a sidewall of the reservoir, the shelf having a plurality of spaced-apart wells therein.

Another aspect of the present invention is a process for screening for an analyte in a sample. The process comprises importing a fluid mixture into a capillary tube coated on at least a portion of its interior surface with a substrate, wherein the fluid mixture comprises a sample suspected of containing the analyte and a reagent comprising a fluorescently-labeled conjugate that is (a) capable of binding to the analyte or to the analyte and the substrate and (b) capable of fluorescing when irradiated with an appropriate electromagnetic signal; maintaining the fluid mixture in the capillary tube for a time sufficient for binding to take place between the substrate and the fluorescently-labeled conjugate; removing excess fluid mixture from the capillary tube; externally irradiating the coated portion of the capillary tube with an electromagnetic signal sufficient to cause fluorescence of bound fluorescently labeled conjugate; and detecting the resulting fluorescence to screen for the analyte.

Still another aspect of the present invention is an apparatus for screening for at least one analyte in a sample. The apparatus comprises a reservoir for a fluid; a conduit to transport the fluid to a port; the port being positioned to draw the sample thereto and to pump fluid therethrough; a means to draw at least a portion of the sample to the port; a means to pump the fluid through the port; a first section having connecting means for a cartridge holding at least one capillary tube so that one end of the capillary tube is in fluid communication with the port; a second section having means to hold a tray having at least one well to communicate with the other end of the capillary tube, the second section also having a means to create a changing magnetic field so that a magnetizable metallic object held within the well of the tray is moved sufficiently to agitate a sample when placed in the well; a means to hold the cartridge and capillary tube to permit the capillary tube to be exposed to a signal generation means; the signal generation means; and a signal detection means positioned to detect a signal emitted from the capillary tube as a result of exposure to the signal from the signal generation means.

Another aspect of the present invention is a combination of a cartridge holding at least one capillary tube. The combination comprises a capillary tube coated on at least a portion of its interior surface with a substrate that is capable of binding to a fluorescently-labeled conjugate and a frame comprising a means for positioning the capillary tube in an exposure region of the frame, wherein the exposure region permits exposure of at least a portion of the coated capillary tube to an external electromagnetic signal that is capable of causing bound fluorescently-labeled conjugate to fluoresce.

Another aspect of the present invention is a capillary tube comprising a substrate on at least a portion of its interior surface, which substrate is capable of being bound to a fluorescently-labeled conjugate.

Still another aspect of the present invention is a process for preparing a glass capillary tube for use in a fluorescent immunoassay. The process comprises coating at least a portion of the internal surface of the capillary tube with a substrate that is capable of binding to a fluorescently-labeled conjugate.

BRIEF DESCRIPTION OF THE DRAWINGS

FIG. 1 is a perspective view of a preferred embodiment of the invention showing cooperation between a cartridge containing capillary tubes and a sample tray and cartridge holder combination when in use.

FIG. 2 is a perspective view of a preferred embodiment of the invention showing cooperation between the sample tray and cartridge during storage.

FIG. 3a is a perspective view of the obverse side of the fully assembled cartridge of a preferred embodiment of the invention showing elements of the design and the capillary tubes held therein.

FIG. 3b is a perspective view of the reverse side of the fully assembled cartridge of a preferred embodiment of the invention showing elements of the design and the capillary tubes held therein.

FIG. 3c is a perspective view of the reverse side of the fully assembled cartridge of a preferred embodiment of the invention showing elements of the design and the capillary tubes held therein, and particularly showing the distal portions of passageways for holding the capillary tubes.

FIG. 3d is a top view of the obverse side of the fully assembled cartridge of a preferred embodiment of the invention showing elements of the design and the capillary tubes held therein.

FIG. 3e is a top view of the reverse side of the fully assembled cartridge of a preferred embodiment of the invention showing elements of the design and the capillary tubes held therein.

FIG. 3f is view of the top or proximal end of the fully assembled cartridge of a preferred embodiment of the invention showing elements of the design and particularly details of the design of the top of the cap that forms a component of the cartridge.

FIG. 3g is a view of the bottom or distal end of the fully assembled cartridge of a preferred embodiment of the invention showing elements of the design and the capillary tubes held therein.

FIG. 3h is a side view of the fully assembled cartridge of a preferred embodiment of the invention showing elements of the design and the capillary tubes held therein.

FIG. 4 is an exploded view of the various components of a preferred embodiment of the invention showing cooperation among elements.

FIG. 5 is a perspective view showing a distal orientation of the reverse side of a frame that forms a component of a preferred embodiment of the cartridge of the invention.

FIG. 6 is a perspective view showing a proximal orientation of the reverse side of the frame that forms a component of a preferred embodiment of the cartridge of the invention.

FIG. 7 is an exploded view of the top side of the holder that forms a component of a preferred embodiment of the cartridge of the invention showing cooperation between a receptacle and a cap.

FIG. 8 is an exploded view of the underside of the holder that forms a component of a preferred embodiment of the cartridge of the invention showing cooperation between the receptacle and the cap.

FIG. 9 is a perspective view of a preferred embodiment of the sample tray of the invention showing sample wells, a reservoir, and a cartridge storage compartment.

FIG. 10 is a perspective view of a preferred embodiment of the sample tray of the invention showing the various components of the cartridge storage compartment.

FIG. 11 is a perspective view of an alternative embodiment of the sample tray.

FIG. 12 is a perspective view of a preferred embodiment of an apparatus for use with preferred embodiments of the devices for determining the presence of an analyte, particularly showing the relative position of the sample tray and cartridge.

FIG. 13 is a transparent view of a preferred embodiment depicted in FIG. 12, showing critical internal components.

FIG. 14a is a block diagram of a preferred embodiment of the apparatus showing cooperation among the various electronic parts.

FIG. 14b is a block diagram, corresponding to FIG. 14a, of a preferred embodiment of the apparatus showing component designations known to those of ordinary skill in the art.

FIG. 15 is a simplified diagram of the solid-phase fluorescence immunoassay (SPFIA) principle of a preferred embodiment of the invention employing a coating of a capture binding member comprising an antigen in a competitive fluorescence immunoassay.

FIG. 16a is a representative plot of concentration in parts per billion to normalized fluorescence for calibration standards comprising known amounts of Penicillin G.

FIG. 16b is a representative plot of concentration in parts per billion to normalized fluorescence for calibration standards comprising known amounts of Amoxicillin.

FIG. 16c is a representative plot of concentration in parts per billion to normalized fluorescence for calibration standards comprising known amounts of Ampicillin.

FIG. 16d is a representative plot of concentration in parts per billion to normalized fluorescence for calibration standards comprising known amounts of Cloxacillin.

FIG. 17a is a representative plot of concentration in parts per billion to normalized fluorescence for calibration standards comprising known amounts of Cephapirin.

FIG. 17b is a representative plot of concentration in parts per billion to normalized fluorescence for calibration standards comprising known amounts of Ceftiofur.

FIG. 18 shows a Penicillin G immunoassay where raw fluorescence signals are plotted as a function of spiked concentration in raw milk to produce a multi-level standard curve.

DETAILED DESCRIPTION OF PRESENTLY PREFERRED EMBODIMENTS

Definitions

The following definitions are provided to help interpret the disclosure and claims of this application.

Amount: The term amount as used herein refers to the concentration or quantity of analyte in a sample either relatively or absolutely.

Antibody: The term antibody as used herein refers to a protein that recognizes a particular epitope on its homologous antigen. The antibody can be a capture binding member of a substrate comprising the surface of a capillary tube or it can be a moiety of a fluorescently-bound conjugate. An antibody can be a polyclonal antibody, a monoclonal antibody or a genetically engineered molecule capable of binding the corresponding member of a specific binding pair.

Antigen: The term antigen as used herein refers to any substance that binds specifically to an antibody, as defined herein. An antigen can be a capture binding member of a substrate comprising the surface of a capillary tube, or it can be a moiety of a fluorescently-bound conjugate, or it can comprise an analyte.

Analyte: The term analyte as used herein, refers to any substance or chemical constituent of a sample that is being analyzed. Analytes detectable by an immunoassay can be any analyte capable of being recognized and bound by a specific binding pair member. An analyte can be one of the binding members of a homologous antibody-antigen binding pair, that is, the analyte can comprise an antibody or an antigen in an immunoassay.

Capillary tube: A capillary tube as used herein comprises a high surface to volume ratio. A capillary tube can have any suitable shape wherein the longitudinal cross section of the internal walls can be defined by a cylinder, oval, square, rectangle, or any suitable polygon and dimensions that are appropriate for use in this invention, as described hereinafter.

Conjugate: The term conjugate as used herein refers to a compound that comprises two substances, wherein one of the substances is coupled to the other. For example, a first conjugate can be coupled to a third substance to make a second conjugate comprising a first conjugate and a third substance, or a first conjugate can be coupled to a second conjugate to make a third conjugate comprising two conjugates. Coupling can be covalent or non-covalent.

Fluorescent label: The term fluorescent label as used herein refers to a substance which, when stimulated by an appropriate electromagnetic signal or radiation, will absorb the radiation and emit a signal that persists only so long as the stimulating radiation is continued, i.e. it fluoresces.

Fluorometer: The term fluorometer as used herein, refers to an instrument for measuring fluorescence. Generally it comprises a signal generation means (i.e., a source of electromagnetic radiation of a suitable wavelength to cause a fluorescent label to fluoresce), a signal detection means comprising a fluorescence detector, and an appropriate filter or filters.

Immunoassay: The term immunoassay as used herein, refers to a technique that makes use of the specific binding between an antigen and its homologous antibody, either polyclonal or monoclonal, in order to analyze for an analyte in a sample. If the immunoassay comprises use of a fluorescent label that can be detected when excited by an appropriate electromagnetic signal, the immunoassay is a fluorescent immunoassay or FIA.

Reagent: The term reagent as used herein refers to a substance that participates in a chemical reaction or physical interaction. A reagent can comprise an active component, that is, a component that directly participates in a chemical reaction (e.g. covalent binding) or physical interaction (e.g. non-covalent binding), such as a fluorescently-labeled conjugate, and other materials or compounds directly or indirectly involved in the chemical reaction or physical interaction. It can include a component inert to the chemical reaction or physical interaction, such as catalysts, stabilizers, buffers, and the like.

Specific binding: As used herein specific binding refers to the chemical recognition between two substances that results in the coupling of those substances. Such coupling can include, but is not limited to, covalent or non-covalent interaction. For example, the specific binding between an antigen and its corresponding antibody is of greater affinity than the non-specific binding of either specific binding pair member and a non-corresponding substance.

Specific binding pair: As used herein specific binding pair refers to two substances that specifically bind to each other.

Specific binding pair member: Specific binding pair member, as used herein, refers to one member of a specific binding pair. For example, a conjugate, a hapten, an antigen or an antibody can be a specific binding pair member.

Substrate: The term substrate as used herein refers to a material to which another material binds or can be attached. Such a material is generally a surface of a material (e.g., the interior surface of a capillary tube), a solid material on a surface, or a first solid material on a second solid material. Generally a substrate can comprise a capture binding member of a binding member pair that can bind to a second member of the binding pair. For example, a substrate can be an antibody conjugated with a substance that binds to the interior surface of a capillary wall, wherein the antibody would be considered a capture binding member of a binding pair. The corresponding antigen conjugated with a fluorescent label would be the second binding member.

Introduction

In one broad aspect, this invention can be considered to be an immunoassay that employs the interior surface of a capillary tube as a solid phase substrate that can bind a fluorescently-labeled conjugate and detect an analyte in a sample. Another aspect of this invention includes a capillary tube coated on at least a portion of its interior surface with a substrate that is capable of binding with a fluorescently-labeled conjugate. This unique capillary tube provides, at least in part, the basis for other aspects of the invention, such as a combination of the capillary tube with a cartridge and a process for screening for an analyte in a sample using the capillary tube. Another aspect of the invention is a process for preparing the capillary tube of the invention. Still other aspects of the invention include a uniquely designed sample tray for use with the cartridge-capillary tube combination and an apparatus for performing the screening process of this invention. These and other aspects of the invention will be discussed in greater detail hereinafter.

Types of Analytes to be Detected

The immunoassay of this invention is useful for screening for analytes in numerous industries including, but not limited to, health care, food processing, chemical, environmental control, and the like. Thus, the types of samples include various fluids suspected of containing a target analyte such as blood, plasma, urine, saliva, and the like; food products such as milk, wine, beer, and the like; chemical streams, waste streams from chemical plants, rivers, and the like. In some situations, the sample may need to be pre-treated prior to the immunoassay. Where the sample is initially complex, solid, or viscous, it may need to be extracted, dissolved or diluted in order to obtain a sample having the appropriate characteristics for use in the immunoassay. Further, the sample should be one in which binding complexes formed in the subject immunoassay are stable. Binding complexes of the subject immunoassay will generally be stable at pH values ranging from about 5 to about 9. The pH value of the sample may be adjusted, if necessary, to be about 7 by diluting with an appropriate buffer.

A wide range of analytes can be detected using the subject method. Detectable analytes can be any analyte capable of being recognized and bound by a specific binding pair member. The analyte can be an antigen, and antigen receptor (e.g. an antibody), or hapten. Analytes of interest include naturally occurring and synthetic small organic compounds, proteins, saccharides, nucleic acids and the like. Illustrative analytes include compounds used in the raising of domestic animals (e.g. antibiotics and food supplements), food additives, naturally occurring contaminants, dyes, microorganisms and their toxins, and the like. Other analytes include physiologically active compounds, pathogenic markers found in physiological fluids, toxins, surface membrane proteins, cytokines, antibodies, human lymphocyte antigen proteins, hormones, natural and synthetic drugs, proteins of bacteria, fungi and viruses, and the like. Other analytes include compounds found in the environment, such as pesticides, herbicides, organic components of waste discharges, and the like.

Examples of specific analytes detectable in the immunoassay of this invention include compounds from the sulfa family drugs such as sulfamethazine, sulfadimethozine, sulfathiazole, sulfaquinoline and others; tetracycline, gentamicin, chloramphenicol, aflatoxin, digoxin, and salmonella. Still other analytes include, hydrocarbons, such as benzene, toluene, ethyl-benzene, and xylenes.

The immunoassay is particularly valuable for detecting analytes, such as antibiotics in milk samples, and is presently preferred to be used for these compounds. Antibiotics are administered to cows for the prevention and treatment of infections, such as mastitis, and to enhance animal growth and milk production. Antibiotics are also abused through off-label, illegal administration in an attempt to quickly bring a sick animal back into the producing herd.

For the purpose of maintaining a safe and healthy food supply, it is important to identify, monitor and minimize the existence of antibiotic residues in milk and milk products. Since milk and milk products are widely consumed, antibiotic residues should be avoided for several reasons: (i) Some antibiotic residues can cause allergic reactions in sensitive consumers (approximately 5 to 10% of the population is hypersensitive to penicillin and other antibiotics), (ii) Small concentrations of antibiotic residues can aid in the selection of resistant strains of pathogens that are harmful to humans, and (iii) Antibiotic residues can interfere with starter cultures used in the production of processed milk products such as cheese and yogurt. Consequently, the United States Food and Drug Administration (US FDA) has established safe/tolerance levels for antibiotic residues in milk and milk products, shown in Table I.

The antibiotics that are most commonly administered to lactating cows, and consequently those antibiotics that are usually found as contaminants in milk and mil-products are from the β-lactam group (penicillin G, ampicillin, cloxacillin, cephapirin, ceftiofur, and amoxicillin). The structures for these compounds are available by consulting the "Merck Index"—Eleventh Edition.

TABLE I

U.S.F.D.A. Safe/tolerance levels for β-lactam drugs in milk

| Drug | Safe/Tolerance Level (ppb)[a] |
|---|---|
| Penicillin G | 5 |
| Amoxicillin | 10 |
| Ampicillin | 10 |
| Cloxacillin | 10 |
| Cephapirin | 20 |
| Ceftiofur | 50 |

[a]ppb = parts per billion, 1 ppb is equal to 1 ng/mL.

The Immunoassays

Depending on the type of analyte to be detected, different immunoassay formats can be employed. A particular immunoassay format can be modified depending on the nature of the analyte, the nature of the sample, and the like. In general, immunoassays useful in the subject method are based on the formation of complexes between specific binding pair members. Common to each immunoassay used in the subject method will be a substrate comprising a first binding pair member. The immunoassay also employs a second binding pair member comprising a fluorescently-labeled conjugate that can couple to an analyte or to both the first binding pair member and an analyte. Throughout this specification, the term "capture" is used with binding member or specific binding pair member. It refers to a specific binding pair member comprising a substrate on the interior surface of a capillary tube, although it is not limited to such use if indicated otherwise.

Both sandwich and competitive immunoassay formats can be employed in the subject method. The particular immunoassay format employed will depend on the particular analyte characteristics, the sample characteristics, the available reagents, and the like.

In a sandwich immunoassay, a fluorescently-labeled conjugate is employed that is a specific binding member, wherein the fluorescently-labeled conjugate binds to the analyte at a site other than the site to which the other binding member, which is on the interior surface of the capillary tube. The fluorescently-labeled conjugate is mixed with a sample and the resulting mixture is drawn up into the capillary tube. The analyte will bind to the fluorescently-labeled conjugate and to the other binding member moiety of the substrate, so that the amount of fluorescent label bound to the capillary tube wall will be directly proportional to the amount of analyte present.

In one type of a competitive immunoassay, a fluorescently-labeled conjugate binding member binds directly to an analyte or to the substrate, via an analog of the analyte present on the substrate. Thus, the analyte and the substrate "compete" to bind with the fluorescently-labeled conjugate binding member. In this format, both the substrate and the analyte have a binding region (also referred to as an epitopic region) that bind to the fluorescently-labeled conjugate binding member. The moiety of the substrate can be a ligand, an antibody, or binding fragment thereof, typically analogous to an epitopic region of the analyte. Here the amount of fluorescent label bound to the interior wall of the capillary tube is inversely proportional to the amount of analyte present.

In another type of a competitive immunoassay, a fluorescently-labeled conjugate competes with the analyte for binding sites to the capture binding member of the substrate. In this format, the capture binding member can comprise an antibody with both the analyte and the fluorescently-labeled conjugate comprising homologous antigen binding members. In the absence of analyte, the fluorescently-labeled conjugate will not have competition for binding sites on the capture binding member of the substrate. Thus, the amount of fluorescent label bound to the interior wall of the capillary tube is inversely proportional to the amount of analyte present.

With this in mind, it can be seen that an aspect of this invention is a process for screening for an analyte in a sample, which process comprises importing a fluid mixture into a capillary tube having a substrate comprising a capture binding member wherein the fluid mixture comprises a sample suspected of containing the analyte and a reagent comprising a fluorescently-labeled conjugate that is (a) capable of binding to the analyte or to the analyte when bound by the capture binding member and to the substrate; (b) capable of fluorescing when irradiated with an appropriate electromagnetic signal. The process further comprises maintaining the fluid mixture in the capillary tube for a time sufficient for binding to take place between the substrate and the fluorescently-labeled conjugate; removing excess fluid mixture from the capillary tube; externally irradiating the coated portion of the capillary tube with an electromagnetic signal sufficient to cause fluorescence of bound fluorescently-labeled conjugate; and detecting the resulting fluorescence to screen for the analyte.

In a competitive immunoassay, a particularly convenient protocol is where fluorescently-labeled conjugate is first mixed with a liquid sample suspected of containing the analyte to provide a substantially homogeneous mixture and then the sample is taken into the capillary tube. The fluorescently-labeled conjugate can be a solid, or preferably, a buffered solution, and as appropriate, can serve to dilute the sample and provide the appropriate pH.

Once the sample suspected of containing the analyte has been mixed with the appropriate fluorescently-labeled conjugate, the resulting mixture is introduced into the interior of a capillary tube that has been interiorly coated with an appropriate capture binding pair member moiety of a substrate appropriate for the analyte being assayed. Preferably, a sample is introduced by capillary force, although an external force such as suction or positive pressure can also be used. In the example referred to above, an antibiotic in milk, an antigen analogous to an antibiotic of interest, is coated on the interior surface of the capillary tube. The entire interior surface or a part thereof can be coated. However, enough of the surface must be coated so that a binding reaction can take place between the fluorescently-labeled conjugate and the capture binding member moiety of the substrate such that the capillary tube can be read by irradiating it and detecting the resulting fluorescence. Generally, sample volumes introduced into the capillary tube will range from about 2 to about 20 µl usually about 5 to about 15 µl, more usually about 5 to about 10 µl, After the sample portion has been introduced into the capillary tube, the sample is incubated for a sufficient time period for binding to occur, that is to form complexes between members of specific binding pairs, e.g. a fluorescently-labeled conjugate binding member and the substrate comprising the bound antigen. The incubation step will typically occur at room temperature, although temperatures in the range of about 10° C. to about 50° C. can be employed. Incubation times will typically range from about 0.5 to about 5 minutes, usually about 0.5 to about 3 minutes, and more usually about 2 minutes. Frequently, the time necessary for introducing a wash solution into the capillary tube will suffice for the incubation.

For the most part, the subject methods will depend solely on the capillary tube and the fluorescently-labeled conjugate for carrying out the immunoassay. However, in some situations more complex protocols can be employed. For example, instead of having the conjugate binding member labeled directly, one can indirectly label the binding member. Where the binding member is an antibody, one can use a fluorescently-labeled anti-antibody, so as to have a universal fluorescent reagent.

One can have a situation where one adds both a fluorescently-labeled conjugate and its reciprocal binding member, where the conjugate competes with the analyte for the reciprocal binding member. The capillary tube can comprise a capture binding member that captures the reciprocal binding member. For example, the reciprocal binding member can be an antibody and the capillary tube can be coated with Protein A or G, so as to capture all antibodies.

After an incubation step, any fluorescently-labeled conjugate free in the medium is preferably removed from the capillary tube. Removal of unbound fluorescently-labeled conjugate is conveniently accomplished through introduction of a washing fluid that displaces unbound fluorescently-labeled conjugate from the capillary tube. A variety of wash fluids can find use for the washing step. The pH of the wash fluid will be a pH in which the binding pair complexes are stable.

Typically, the pH will range from 5 to 9, usually 6 to 8, and more usually about is 7. Depending on the nature of the fluorescent label of the conjugate, wash solutions which enhance the fluorescence of the conjugate label can be employed. For example, the fluorescence of a particular fluorescent label can be enhanced in slightly alkaline or basic solution. In such a case, a buffer having a pH above 7, but usually less than 9, can be employed. Exemplary wash fluids comprise water, buffers, such as phosphate, phosphate buffered saline (PBS), saline solutions, carbonate buffers, and the like. The wash fluid can be introduced into the capillary tube using any convenient means. Usually the wash fluid will be introduced into the capillary tube using the same means as the means used for introduction of the sample. The wash solution can be taken up a number of times, usually not more than about 6, more usually not more than about 2, or the wash solution can be forced through the capillary tube using a syringe, pump or other device.

After the washing step where the unbound labeled conjugate is washed from the capillary tube, the presence of fluorescently-labeled conjugate remaining bound to the capture binding member on the substrate on the capillary tube surface is detected in a detection step. The detection step can be conducted immediately after the wash step, or can be delayed for a period of time, if necessary. While the detection step can be conducted with wash fluid in the capillary tube, preferably the capillary tube can be dried prior to the detection step to minimize the possibility of interference in the ensuing detection step. The drying may be done by any appropriate means such as centrifuging, air drying, vacuum drying and the like. Preferred techniques are discussed hereinafter. If the detection step is to be delayed, the capillary tube can be stored for a reasonable period of time under ambient or reduced temperature conditions.

Many different fluorescent labels can be employed in the subject immunoassays. Suitable fluorescent labels should be capable of conjugation with antigens, haptens or antibodies in order to be used in the fluorescently-labeled conjugate. Selection of the fluorescent label is based Qn synthetic convenience, emission maximum, quantum efficiency, stability under the assay conditions, and the like, but the fluorescent label is not critical to the invention, so long as there is a minimum quantum yield to provide the desired sensitivity. A large number of commercially available fluorescent labels can be employed. Illustrative fluorescent labels include fluorescein isothiocyanate (FITC), rhodamine, Texas Red, phycoerythrin, Cy-5® and allophycoerythrin, and particularly, fluorescent labels that fluoresce above about 550 nm, more particularly, fluorescent labels that fluoresce above 600 nm, and efficiently absorb light having absorption above 500 nm; more particularly, 650 nm, such as Cy-5®. The fluorescent labels can be conjugated to form the fluorescently-labeled conjugate using any convenient method. See e.g. Harlow & Lane, Antibodies (1988) pp 353–358.

When fluorescently-labeled conjugates are used, detection is accomplished by first irradiating a region of the capillary tube comprising the detection region, followed by measuring the resultant emitted fluorescent signal. Any convenient irradiation means can be employed for providing the appropriate wavelength. Exemplary irradiation means include lasers, light emitting diodes, tungsten lamps and the like. The wavelength of light used in the stimulation means will depend on the particular fluorescent label. Generally, the irradiation light wavelengths will range from 300 to 900 nm, usually from about 350 to 800 nm, and more usually from about 450 to 800 nm. For example, where Cy-5® is the fluorescent label, the wavelength of the irradiation light will range from 630 to 650 nm. The fluorescence from the fluorescently-labeled conjugates present in the capillary tube will be measured. Measuring the emitted signal is accomplished by detecting the photons emitted in the detection region. Means for measuring fluorescence are commercially available and any convenient fluorescence detector can be used. Various photodiodes, photomultipliers, and the like, can be employed, and in some instances a visual detection will suffice, if a fluorescently-labeled conjugate is used that fluoresces in the visible spectrum.

Depending upon whether a competitive or sandwich immunoassay is employed, and the reagents employed, the fluorescence intensity will be directly or inversely proportional to the amount of analyte in the sample. Where one is interested in a qualitative result or a semi-quantitative result, such as determining whether the amount of analyte is above a predetermined threshold, versus determining the concentration of analyte, the amount of fluorescently-labeled conjugate is selected to provide a clear signal as compared to the absence of analyte or analyte below the predetermined value. Thus, one can use an amount of conjugate which will be substantially absent in the detection region in the absence of analyte and provide an intense signal at the lowest concentration that one would anticipate to be encountered of analyte in the sample or vice versa.

For quantitation, the resultant electrical signal can be accurately measured using appropriate hardware and software. The area from which the fluorescence is measured is controlled to provide for consistent values. Controls can be employed, where the signal to concentration of the analyte is determined, so that the signal can be directly related to the concentration of analyte in the immunoassay sample. In this manner, both the presence and the amount of analyte in the sample can be determined.

As discussed hereinafter, generally only a small amount of the sample (less than about 1 ml) is mixed with the conjugate. As discussed in greater detail hereinafter, this is done preferably in a small well of a sample tray using a means of agitation. It may be important that the mixing and incubation step and the subsequent incubation step in the method of this invention be carried out for the same defined period of time to minimize variations from test to test in a series. Thus, it may be preferred to automate the steps of the method to eliminate operator error to the greatest extent possible. This will be discussed in greater detail in the following discussion of preferred devices and apparatus depicted in the figures.

Thus, from the preceding discussion, it can be seen that solid-phase fluorescence immunoassay (SPFIA) takes advantage of the specificity of a binding pair affinity, e.g., antibody-antigen recognition, and incorporates a suitable fluorescent label for detection. FIG. 15 diagrams the principle of the SPFIA. A sample (e.g., milk) is mixed with a known amount of a fluorescently-labeled antibody which is specific to an analyte (e.g., a β-lactam antibiotic). An essentially instantaneous binding reaction will occur between the antibody and the analyte in the sample. A solid support, e.g., the inside wall of a glass capillary tube as a substrate comprising an antigen analogous to the analyte attached thereto will then be exposed to the sample. When the sample is removed from the capillary tube and the capillary tube is examined with a fluorometer, and any fluorescence is detected. In the milk example shown in FIG. 15, a substrate incubated with milk samples with high concentrations of an antibiotic will have fewer free fluorescently-labeled antibody molecules to react with the antigen substrate, thus yielding lower fluorescence signals. Conversely, milk samples with low concentrations of antibiotic will have more free antibody molecules, thus more fluorescent conjugates will bind to the substrate and will provide higher fluorescence signals. Mathematically, the measured fluorescence signal is inversely proportional to the concentration of analyte in the sample for these competitive assays. Thus, in FIG. 15 the analyte is the antibiotic and the capture binding member moiety of the substrate on the interior capillary tube surface is an antigen (e.g., an analog of the analyte) that is bound by the fluorescently-labeled antibody conjugate.

The Capillary Tube And Its Preparation

An important aspect of this invention is the unique capillary tube coated on at least a portion of its interior surface with a substrate that is capable of binding with a fluorescently-labeled conjugate. A wide variety of capillary tubes designed for diverse uses are known in the art and are suitable for use in the subject invention.

Generally, capillary tubes used in the subject method are made of a substance that allows irradiation light and fluorescence emissions to be transmitted across the capillary tube wall. Thus, when an electromagnetic signal from an external source contacts the capillary tube wall, the signal must go through the wall. The resulting fluorescence must then be transmitted out through the wall. Materials from which suitable capillary tubes can be formed include glasses, such as soft glass, silicate glass and fused silica. Other materials include plastics, such as polystyrene, polyethylene, polypropylene, polyvinyl chloride (PVC), and the like. Other materials may be apparent to one of skill in the art upon reading this disclosure. A presently preferred embodiment is a borosilicate glass capillary tube, such as the one available from Drummond Scientific, Broomall, Pa.

Capillary tubes suitable for use in the subject invention can have a wide variety of dimensions, as long as liquid media are effectively drawn up by suction or capillary force. The capillary tubes can have cross-sections which are circular, square, rectangular, oval, and the like. Typically, the capillary tubes will have circular cross-sections. The inner diameters of suitable capillary tubes can range from about 0.1 micrometers ($\mu$m) to about 1 millimeter (mm), usually about 0.3 $\mu$m to about 1.0 mm and more usually about 0.50 $\mu$m to about 1 mm, preferably about 0.65 mm for a milk immunoassay. The outer diameter of a suitable capillary tube can be about 1.0 mm to about 1.5 mm. The length of suitable capillary tubes will typically be about 10 mm to about 150 mm. Usually the length will be at least about 15 mm, more usually at least about 25 mm, up to about 250 mm for ease of handling. While the capillary tubes of this invention may be interconnected by a planar sheet, generally they are free standing, individual capillary tubes.

For glass capillary tubes, to enhance binding of a substrate to the glass, the surface can be coated with a material to enhance a binding capability on the interior surface. At least one region of the interior surface of the capillary tube, a detection region, will be coated with a suitable substrate that will include a member of a binding pair. The member of a binding pair coated on the surface, at the detection region, binds directly or indirectly through an intermediate binding agent to a fluorescently-labeled conjugate. Depending on the particular method used to coat the capillary tube, the region can encompass the entire interior surface of the capillary tube or can be limited to a portion of the interior surface of the capillary tube. The region of the interior surface comprising a capture binding member coated thereon will typically range from about 10 to 100% of the interior surface, and will usually range from about 30 to about 100% of the interior surface. Preferably more than about 80% of the interior surface is coated. Conveniently, the entire capillary tube, or one end thereof, can be immersed in the coating media to be coated. When immersed at one end, the coating medium can be brought up into the capillary tube by any suitable means, e.g. by capillary force, conveniently to a predetermined height, which can be indicated by a scoring or other designation on the capillary tube. Alternatively, the liquid can be pumped or sucked into a portion of or the whole length of the capillary tube. This means that all or a portion of the external surface can be coated with the capture binding member as well.

Depending on the particular immunoassay format used in the subject method, a variety of agents can serve as the binding members. In general, a binding member of a pair should complex or bind to its complementary binding pair member in the subject immunoassays with sufficient affinity to withstand wash procedures used in the subject method. Typically, the affinity between the binding member and its complementary binding pair will be at least about $10^6$L/mol, frequently at least about $10^8$L/mol or higher. One member of a binding pair will bind or complex directly or indirectly to a fluorescently-labeled conjugate. For example, in a competitive immunoassay format, the capture binding member (e.g., the analyte analog on the interior surface of the capillary) binds directly to a fluorescently-labeled conjugate. In a sandwich immunoassay format, the capture binding member will complex to the fluorescently-labeled conjugate indirectly through the analyte. Illustrative binding members include receptors, such as antibodies and binding fragments thereof, e.g. F(ab) and F(ab)$_2$ fragments), lectin, ligands, such as antigens, haptens or other reciprocal binding members; and conjugates comprising ligands and receptors, bonded to the fluorescent label.

Instead of coating a region of the interior with a capillary tube with a substrate containing a single capture binding member, the interior surface of the capillary tube can be coated with two or more capture binding members at the same or different sites. In this embodiment, each different capture binding member will be involved in the detection of a different analyte in the sample. When the binding members are at the same site, the fluorescent label associated with each analyte can be independently determined, e.g. different emission maximum wavelength, at least about 10 nm different, and/or different delay time for emission. Thus, one can assay for a multiplicity of analytes simultaneously.

To coat the internal wall of capillary tubes for use in the subject method, capillary tubes are contacted with a solution comprising the capture binding member. For coating the internal capillary tube surface with the substrate solution, a variety of techniques can be employed, depending in part on the nature of the substrate and the nature of the internal wall. With most proteins, particularly antibodies, albumins and globulins, the proteins stick to the surface without covalent bonding, and are stable under the conditions of the immunoassay.

In preparing the subject capillary tubes, as indicated for proteins above, it can be sufficient to contact capillary tubes with untreated surfaces to a solution comprising the binding reagent. The binding solution is usually a buffered solution having from about $10^{-7}$ to $10^{-3}$ g protein/ml. Typically, the protein binding member will be an antibody or fragment thereof for direct assays. For indirect assays, the protein will typically be an analog of the analyte. For the most part, the protein binding member will be an antibody or fragment thereof. Methods of stably coating glass and plastic surfaces are well known. See e.g. Harlow & Lane, Antibodies: A laboratory manual, Cold Spring Harbor Laboratory, Cold Spring Harbor, N.Y. (1988). In many instances, where the binding member is not a protein, it can be conjugated to a protein, leaving the binding sites available for binding to the complementary binding member. For example, haptens can be conjugated to a protein that will not interfere with the immunoassay. In this way, an otherwise non-binding analyte or a mimetic or analog thereof can be directly bound to the internal surface of the capillary tube without having to functionalize the surface so as to provide covalent binding of the otherwise non-binding substance.

In the case of a preferred capillary tube, i.e., glass, it is preferred to first coat the interior surface with an agent which enhances the binding of the protein to the surface. Thus, where the binding member does not provide for stable binding to the interior surface of the capillary tube, the surface is activated or functionalized to provide covalent or non-covalent binding of the binding member to the capillary tube surface. The particular technique used in treating the capillary tube surface will depend on the composition of the capillary tube and the binding member, e.g. the functional groups available on the binding member for reaction. With surfaces such as plastics, e.g. polystyrene and polyethylene, the surface can be functionalized to provide for reactive amino, carboxy, thio, sulfonyl, hydroxy or other functional groups, by acylation, nitration and reduction, oxidation with ozone, chlorosulfonation, and the like. The specific functional group provided on the capillary tube surface will depend on the binding member. If the binding member does not naturally comprise a useful available functional group, the binding member can be modified, so as to provide for a functional group that will react with the activated surface, e.g. amino with carboxy, thiol with activated olefin, hydroxy with an activated halogen, and the like. For non-covalent binding of the binding member to the surface, a hydrophobic surface may be provided, that is, a surface that has a long chain alkyl or alkenyl group attached, e.g., through a silicon attaching group.

For treating the surfaces of glass capillary tubes, the surface can be "functionalized" by using a silicon-based compound having as one part of the compound a silicon moiety that reacts with the glass surface of the capillary tube and the other part of the compound being carbon-based that provides a suitable functional group, e.g. alkyl, alkenyl, amino, carboxy, sulfonyl, thiol, activated olefin, such as maleimido, and the like, that will bind with the binding member either covalently or non-covalently (e.g., by van der Waals' forces).

Generally, the coating is done using a silicon-based material that. provides a basis for covalently or non-covalently forming a suitable substrate on the interior surface. Suitable silicon-based materials include silanes or siloxanes that bind through the silicon to the interior glass surface and provide a surface extended into the cylinder of the capillary tube to which an appropriate substrate is bound. This is seen in FIG. 15. Examples of suitable siloxane materials include aminoalkylsiloxanes and alkyl or alkenyltrialkoxysilanes. Conveniently, aminoalkylsiloxanes known in the art can be used, where the aminoalkyl group is of from about 2 to 6 carbon atoms and the alkoxy groups are of from about 1 to 6 carbon atoms. Preferably the silane based material is represented by the formula R—Si(OR$_1$)$_3$, wherein R is an alkyl or alkenyl of about 12 to about 20 carbon atoms and R$_1$ is an alkyl of one to four carbon atoms. A particularly preferred silane-based material is a compound represented by the formula R—Si(OR$_1$)$_3$, wherein R is a straight chain alkyl of 18 carbon atoms and R$_1$ is ethyl. Preferably octadecyltriethoxy silane is chosen as the silane coating material, this is available through Pierce Chemical Company as AquaSil®.

After the binding member has been bound to the surface of the capillary tube, non-specific active sites or "hot spots" can remain on the capillary tube surface.

These active sites must be occupied or blocked prior to use of the capillary tube in the subject method. Otherwise, non-specific adsorption of the various assay reagents can occur. Non-specific adsorption should be avoided because it can result in non-specific binding of the label to the surface. Blocking of active sites can be achieved by contacting the internal capillary tube surface with a wide variety of blocking solutions. Coating the capillary tube surface with the blocking solution can be achieved using the methods described above for coating the surface with the binding member. The blocking solution of choice will depend on the particular immunoassay being conducted. See e.g., Harlow and Lane, Antibodies (1988) 497, supra. Illustrative blocking solutions include Blotto, Blotto/Tween, Tween, BSA and Horse Serum.

Generally, silane-based coating is carried out by incubating an appropriate capillary tube in a solution containing the silane based material dissolved in an appropriate solvent, such as water, for a period of time and at a temperature sufficient to allow binding of the silane material to the internal surface of the glass capillary tube. An appropriate temperature range is about 10° C. to about 50° C., with ambient temperature being preferable. The binding will take place within about 10 minutes, but the capillary tubes can be incubated for an hour or more. The capillary tube is then dried via a suitable means such as by purging with nitrogen or other suitable gas or by centrifugation. Any residual moisture can be removed by incubating the capillary tube in an oven at a suitable temperature, such as about 110° C. to about 140° C., for about an hour and/or under a vacuum. After incubation, the capillary tube will be allowed to cool to room temperature before treating it with the next coating. Once the glass is alkylated by the silane material it is susceptible to non-covalent binding with sticky proteins. A substrate comprising a capture binding member, i.e. a protein conjugated to a capture binding member of an antigen-antibody binding pair, can be coupled to the silanization substrate layer. Alternatively, a protein conjugated to another protein substance that permits binding to a third substrate comprising the capture binding member can be applied. When coating a protein or conjugated protein to the silanization layer, a longer incubation time will usually be required, typically between about 1 to about 24 hours for a similar period of time. After coating with appropriate substrate layers, a final coating with an innocuous protein blocking solution is applied to cover "hot spots" previously discussed comprising exposed alkyl groups. Alternatively, the blocking step can occur after the attachment of the second layer, but before attachment of a third layer in cases where a third layer is used. The coated and blocked capillary tubes are typically incubated in the blocking solution for at least 1 hour and as long as 24 hours. The capillary tube is then substantially dried. A wash solution, such as deionized water, is then passed through the capillary tube to remove any substrate material not bound to the surface of the capillary tube or to another substrate. The capillary tube is then substantially dried by any appropriate means. It is advantageous to aid removal of residual water by incubating the capillary tube in a vacuum oven at the highest temperature possible that would not denature any bound protein, e.g. about 37° C. for at least one hour. Once the capillary tubes have been prepared, they can be used immediately or conveniently stored for use at a later time. Capillary tubes can be stored for use at a later time at ambient or reduced temperature conditions. Example 9, Example 10, and Example 11, describe in detail, preparation of capillary tubes for use with a preferred embodiment of the invention.

Another aspect of this invention comprises a process for preparing a glass capillary tube for use in a fluorescent immunoassay, which process comprises coating at least a portion of the internal surface of the capillary tube with a substrate that is capable of binding to a fluorescently-labeled conjugate. In a preferred aspect, the process comprises coating at least a portion of the interior surface of the capillary tube with a silane-based material and binding a protein conjugate to the silane-based material, which conjugate is capable of binding to a fluorescently-labeled conjugate. Protein conjugates that are particularly useful include bovine serum albumin (BSA) and human serum albumin (HSA), the former being preferred.

A Cartridge For Use With Capillary Tubes

Capillary tubes prepared by the methods described above can be used individually or in combination for an immunoassay in accordance with the method discussed above. The assay can be performed manually or automatically, as discussed hereinafter. One end of a single capillary tube can be introduced into a sample and sample drawn up by any convenient means, e.g. capillary action or active pumping, to provide an appropriately sized sample in the capillary tube. Alternatively, a plurality of capillary tubes coated with appropriate binding members can be used to permit a plurality of immunoassays on one sample or a single immunoassay on multiple samples to screen for one or multiple analytes. The capillary tubes can be held in a cartridge that permits sequential or simultaneous use and/or that permits interaction with other devices and/or apparatus to effectuate an immunoassay of this invention.

Thus another aspect of this invention is a combination of a cartridge holding at least one capillary tube, which cartridge comprises a capillary tube coated on at least a portion of its interior surface with a substrate that is capable of binding to a fluorescently-labeled conjugate and a frame comprising a means to position the capillary tube in a region of the frame that permits exposure of at least a portion of the coated capillary tube to an external electromagnetic signal that is capable of causing any bound fluorescently-labeled conjugate to fluoresce. The fluorescence is then detected with an appropriate signal detection means.

Another related aspect of this invention is a cartridge for securely holding a plurality of spaced-apart capillary tubes, wherein the cartridge has a plurality of passageways for aligning the capillary tubes therein and at least a portion of the cartridge permits exposure of the capillary tubes to an external electromagnetic signal that is capable of causing a fluorescently-labeled conjugate on the internal surface to fluoresce. The cartridge preferably has a holder with a passageway therethrough and a port for permitting fluid to be passed through each capillary tube. The cartridge can be manufactured by methods known to those of ordinary skill in the art, and is preferably injection molded. The cartridge is particularly suitable for cooperating with a unique sample tray and with a semi-automated apparatus for fluorescence immunoassays, as will be discussed in more detail hereinafter.

A detailed description of a preferred embodiment of the cartridge is provided with the description of the drawings and alternative embodiments are provided thereafter.

A Sample Tray For Use In Immunoassays

Capillary tubes as prepared above can be used with commercially available containers suitable for independently housing the reagents and waste of immunoassays, such as microtiter wells or plates. Alternatively, the capillary tubes can be used with a sample tray designed to contain a reagent and means to mix fluid held within the wells.

Another aspect of this invention, therefore, is a tray for holding multiple portions of a sample, which tray comprises a reservoir sufficient to hold a quantity of fluid, and a plurality of spaced apart wells therein. Preferably, the sample tray also independently houses a metallic washer for mixing any fluid held within the wells, and has a means to prevent the metallic washer from falling out of the well, preferably a retaining ridge with a diameter smaller than the external diameter of the metallic washer. The sample tray may be manufactured by any number of methods known to those of ordinary skill in the art and is preferably injection molded.

A preferred aspect of this invention is the combination of the sample tray and cartridge to form a disposable immunoassay testing kit. In this aspect, the sample tray has a section for securely holding the cartridge therein for storage and transportation. Details of the sample tray and cartridge and sample tray combination are provided in the description of the figures.

An Apparatus For Performing the Process for Screening for Analytes

The methods of the present invention for screening for analytes can be conducted manually. The steps of washing and drying can also be conducted manually. The capillary tube can also be used in accordance with the invention with a commercially available fluorometer.

However, it is preferred that the methods be conducted by an automated or semi-automated apparatus. Since, incubation times are relatively short for the SPFIA in capillary tubes, a greater probability exists that operator timing will be off and thus reproducibility compromised. Therefore, an immunoassay apparatus for use with the immunoassays discussed above should have the ability to manipulate one or more capillary tubes and a sample tray, to control the flow of and house fluids, to carry out a substantial portion of the steps of the immunoassay, including the step of detecting the and analyzing the florescent signal. The ability to conduct a plurality of immunoassays on a plurality of samples also increases efficiency. Furthermore, quantitative analysis is possible with an integrated, semi-automated, immunoassay.

Another aspect of the present invention, therefore, is an apparatus for determining the presence of at least one analyte in a sample, which apparatus comprises a reservoir, a means to control the flow of fluid contained within the reservoir or in a sample tray, a first section to attach the cartridge of the present invention and similarly the sample tray of the present invention, a means to dry the capillary tubes, a fluorometer to measure the level of fluorescence, and a means to analyze the resulting signal and report a qualitative or semi-quantitative result and optionally a quantitative result.

The apparatus can cooperate with the cartridge and sample tray combination of the present invention and certain variations thereof. In a typical immunoassay using the cartridge and sample tray combination in cooperation with the apparatus of the present invention, a sample is added to one or more wells in the sample tray. The sample tray is placed on the apparatus and a magnetic mixer located therein agitates the metal washers of the sample tray to mix the contents of the well comprising a fluorescently-labeled conjugate reagent and the sample so as to permit the analyte in the sample to bind to the fluorescently-labeled conjugate. After the sample and reagent are properly mixed, the apparatus positions the sample tray under the cartridge located thereon and draws the mixture into one or more capillary tubes, e.g., via suction. The mixture is incubated in the capillary tubes for a sufficient time for a suitable amount of fluorescently-labeled conjugate to bind to the capture binding member of the substrate, on the surface of the capillary tube. After incubation, the apparatus passes a wash solution through the capillary tube to remove any unbound material. The resulting waste fluid is emptied into the reservoir of the sample tray by the apparatus. The apparatus then notifies the operator to position the cartridge on the centrifuge to spin dry the capillary tubes.

The apparatus then positions the cartridge proximate to a fluorometer. The capillary tubes are exposed to an electromagnetic signal through an exposure opening located on the cartridge and the emitted fluorescence is subsequently detected by a fluorescence detector. The detected signal can be processed for qualitative, semi-quantitative, or quantitative analysis depending on the controls used, and on the analysis software employed.

The level of quantitation possible using the apparatus with the devices of the present invention depends on the affinity of the capture binding member as previously discussed, detector sensitivity, mathematics used to analyze the signal, and whether standards and/or controls are used and if so on what kinds of standards and/or controls. Generally, affinity of about $10^6$L/mol can provide sensitivity in the parts per million range and affinity of about $10^9$L/mol can provide sensitivity in the parts per billion range.

The most basic form of quantitation is the determination of the presence of an analyte. For this to occur, the concentration of analyte in the sample must be above some lower limit of quantitation for the immunoassay. Generally, a semi-quantitative result is reported. A bar code that accompanies the cartridge and sample tray kit contains information regarding the level of fluorescence that corresponds to the boundary between a pass an a fail as indicated by acceptance levels such as the safe/tolerance levels shown in Table I. Typically, each lot of reagent will have a different associated critical level of fluorescence due to, among other things, variations in the binding affinity of the capture binding member substrate. The apparatus will measure the level of fluorescence and compare it to the pass/fail level for the specific immunoassay corresponding to the concentration of interest.

More quantitative analysis is possible with the present invention. FIGS. 16a–d to FIGS. 17a–b show plots of normalized fluorescence versus concentration of analyte in parts per billion (ppb) for the β-lactam antibiotics used with the present invention. Normalized fluorescence corresponds to the level of fluorescence emitted by a fluorescent label bound to the surface of a capillary tube containing analyte as a percentage of the level of fluorescence emitted by a fluorescent label bound to the surface of a capillary tube with no analyte, i.e. a blank. Since concentration is inversely proportional to the level of fluorescence for a comparative assay, the curves formed by the plurality of concentration points have a negative slope. If a sample is run on the apparatus, the resulting fluorescence signal can be compared against the fluorescence signal generated by a blank run in parallel with the sample. The resulting percentage can be plotted on the appropriate graph and a relative concentration of analyte in sample can be determined.

Generally, the apparatus will calculate a semi-quantitative result by using a pass/no-pass level of fluorescence or a quantitative result by plotting a normalized level of fluorescence versus concentration, and calculating a least-squares best fit of a line corresponding to the curves. Thus a multilevel calibration curve can be used, wherein quantitative determination of the amount of analyte in a sample is possible when such concentration is interpolated within the linear range of the best fit polynomial. Even greater quantitative results are possible when standards are prepared to run in parallel with a sample immunoassay, wherein the same lot of fluorescent label is used for both the sample conjugate and blank conjugate.

Since milk production is regulated by the FDA, immunoassays for β-lactam antibiotics are similarly regulated. The FDA typically requires that positive immunoassay results be confirmed. Consequently positive and negative controls should be run with these immunoassays. One convenient method is the use of a control cartridge comprising passing, failing, and blank concentrations of analyte. This control cartridge can be run immediately following a positive test result with the immunoassay.

DETAILED DESCRIPTION OF THE FIGURES

With a detailed description of the various aspects of the present invention provided, a detailed description of preferred embodiments of the devices and apparatus for use with the method for screening for analytes as well as a detailed description of a preferred embodiment of the method as used with the devices and apparatus is now given. While a description of preferred embodiments is given in considerable detail, it should not be construed as limiting to those descriptions discussed hereinafter and variations thereof discussed hereafter. Other variations of the described embodiments can occur to one of ordinary skill in the art that fall within the scope of the present invention.

With reference to terminology, it will be noted in the detailed description of the various aspects of this invention that portions of the devices are referred to as "top", "bottom", "obverse", "reverse", "proximal" and "distal" portions. This is done wholly for convenience and to relate the description to the diagrammatic representations in the drawings. It will be appreciated that the devices can function in any position or orientation and it is within the scope of this invention to have them do so.

FIG. 1 is a front perspective view of the devices of a preferred embodiment of the invention showing cooperation between the components during use. The devices, which are preferably portable and disposable, comprise a cartridge 1, for sealingly holding four radially spaced apart antigen coated capillary tubes 2, where a reaction takes place; and a sample tray 3 for containing sample, a fluorescently-labeled conjugate reagent, and other fluid, such as liquid waste; and for providing storage of the cartridge 1. The sample tray 3, is positioned under the cartridge 1 by an apparatus discussed hereafter so as to permit the cartridge 1 to cooperatively draw fluid into each capillary tube 2 from the sample tray 3. The radial orientation of the capillary tubes 2 functions to ensure that in cooperation with an exposure opening 7 each capillary tube 2 is presented to a signal detection means, discussed hereafter, at the same angle and to permit each capillary tube 2 to be submitted to centrifugal force parallel to its longitudinal axis while secured within the cartridge.

FIG. 2 is a perspective view of the devices of a preferred embodiment of the invention showing cooperation between the components of the devices during storage when not in use. The cartridge 1 slides into a pair of retaining shelves 83, 84 discussed hereafter and snaps in place so as to be secured by the retaining shelves 83, 84 and a pair of fastening clips 75, 76 discussed hereafter (also see FIG. 10).

FIG. 3a to FIG. 3h show the fully assembled cartridge 1 from perspectives showing all sides of the cartridge 1 and particularly showing details of the various design features.

FIG. 4 is an exploded view of the devices of a preferred embodiment of the invention showing cooperation among the elements of the cartridge 1 and sample tray 3. The cartridge 1 comprises a frame 4 and a holder 5 for securing the capillary tubes 2 within the frame 4. The frame 4 comprises a rigid substantially flat rectangular body preferably made of polystyrene, four radially oriented passageways 6 for containing four glass capillary tubes. 2 preferably coated with antigen (so as to conduct a competitive assay), an exposure opening 7 for permitting a beam of light to contact the capillary tubes 2 when secured within the cartridge 1, and four protective tabs 8 for protection of the tips of the capillary tubes 2.

FIG. 5 and FIG. 6 show perspective views of what can be referred to as the reverse side of the frame 4. In a preferred embodiment shown, the frame forms a substantially flat and hollow rectangle about 4 centimeters to about 10 centimeters, preferably about 5.6 centimeters long along a side 9 and a wall 10; about 1 centimeter to about 8 centimeters wide, preferably about 2.7 centimeters wide along two side walls 11, 12; and about 2 millimeters to about 1.3 centimeters high, preferably about 8 millimeters high along the three walls 10, 11, 12. The four passageways 6 originate from a rectangular protruding segment 13 extending from the wall 10. The protruding segment 13 preferably extends about 2 millimeters from the long wall 10 along the horizontal plane of the frame 4 as shown in FIG. 5 and is the same width as the long wall 10, about 3.7 centimeters long. Located on each length wise edge of the protruding segment 13 are three clips 14 for securely attaching the holder 5 discussed hereafter to the protruding segment 13. Extending perpendicularly from the protruding segment 13 are two guide pins 15, 16, a first guide pin 15 and a segmented second guide pin 16, each for guiding a receptacle 35 and cap 36 discussed hereafter into place on the frame 4. The first guide pin 15 has an external diameter between 2 millimeters and 5 millimeters, preferably about 3 millimeters; and is about 1.5 millimeter to about 5 millimeters long or of a sufficient length so that the end of the first guide pin 15 is flush with the top of the cap 36, when the two are cooperatively engaged. The segmented second guide pin 16 has essentially the same length as the first guide pin 15 and an external diameter similar to that of the first guide pin 15 at the base of the segmented second guide pin 16 and up to a ledge 17 located around the perimeter of the segmented second guide pin 16 at about the halfway point along the longitudinal axis of the segmented second guide pin 16. From the ledge 17 to the end of the segmented second guide pin 16, the external diameter of the segmented second guide pin 16 is between about 1.5 millimeters to about 4.5 millimeters, preferably about 2.5 millimeters. In any case of this preferred embodiment, the segmented second guide pin 16 should have a ledge 17 that defines two distinct external diameters that are complementary to the internal diameter of a corresponding segmented guide shaft 50 discussed hereafter located on the cap 36. The function of the different designs of the two guide pins 15, 16, is to permit only one orientation of engagement with the cap 36.

As shown in FIG. 6, along the 8 millimeter wide side of the protruding segment 13 are four equally spaced openings 18, each about 5 millimeters in diameter, for receiving the capillary tubes 2 and receptacle 35 combination discussed hereafter. The openings 18 lead into each passageway 6 which comprises a receiving chamber 19 and a narrow shaft 20 shown in FIG. 5 and FIG. 6. For the purpose of description, the passageways can be divided into two pairs, an inner pair and an outer pair. The axis of the inner pair extend radially toward the long side 9 preferably at about a 5 degree angle from an imaginary line perpendicular to the center of the plane defined by the long wall 10. The axis of the outer pair extend radially toward the long side 9 preferably at about an 18 degree angle from an imaginary line perpendicular to the center of the plane defined by the long wall 10. The angles at which the capillary tubes 2 will extend from an imaginary line perpendicular to the center of the plane defined from the long wall 10 depend on the dimensions of the cartridge 1, but should be such that the capillary tubes 2 are radially orientated so as to ensure consistent exposure of each capillary tube 2 to a signal detection means, discussed hereafter, when the cartridge 1 is placed in a circular centrifuge, also discussed hereafter, and to provide uniform centrifugal force to each tube. That is, when an imaginary line is drawn along the longitudinal axis of each capillary tube 2 when positioned in the cartridge 1, one end of each of the lines should converge to a central point and the arc formed by the combination of the other ends of the lines should form part of a circle. The receiving chambers 19 of the inner pair follow the axis angle, are of the same diameter as the openings 18 or are slightly tapered, and are preferably about 4.5 millimeters deep. The receiving chambers 19 of the outer pair also follow the axis angle, are of the same diameter as the openings 18 or are slightly tapered, and are preferably about 6.5 millimeters deep. The function of the different depths of the receiving chambers 19 is to cooperatively engage the receptacle discussed hereafter. The inner receiving chamber 19 and shaft 20 combinations are about 1.5 centimeters to about 2 centimeters, preferably about 1.75 centimeters long, and the outer receiving chamber 19 and shaft 20 combinations are about 1.3 centimeters to about 1.8 centimeters, preferably about 1.6 centimeters long. The lengths of the combinations of the inner and outer receiving chambers 19 and narrow shafts 20 are determined by the radial orientation of the passageways 6 and a curve formed by an exposure opening 7, which curve functions to ensure that each radially oriented capillary tube 2 positioned within the frame 4 is equally exposed to a signal detection means discussed hereafter when the cartridge 1 is positioned in a centrifuge discussed hereafter. Each shaft 20 is of a thickness sufficient for slidingly fitting a capillary tube 2 therein. Each receiving chamber 19 and shaft 20 combination is cross-sectionally open along the top plane of the frame 4. This results in a cross-sectional parabolic shape for the shaft 20 that is about 5 millimeters deep. The cross-sectional cut is a byproduct of the design of a tool used to manufacture the frame 4. However, the cross-sectional cut of the shaft 20 also functions to expose any damage to a capillary tube 2 held therein. At the end of the shafts 20 are openings 21, as shown in FIG. 5, through which the capillary tubes 2 pass for presentation to the exposure opening 7. As discussed previously, the exposure opening 7 forms a curve that corresponds to the radial orientation of the capillary tubes 2 so as to ensure equal exposure of the capillary tubes 2 to a signal detection means discussed hereafter. The exposure opening 7 is of a width such that preferably about an 8 millimeter portion of each capillary tube 2 is exposed along the curve formed by the exposure opening 7 when secured within the frame 4 by the holder 5 discussed hereafter. The long side 9 comprises a lip preferably about 1.5 millimeters deep and preferably about 3.2 millimeters high wherein the 'L' formed by the lip faces towards the reverse side of the frame 4. The dimensions of the lip are such that the long side 9 is provided sufficient structural support to make it substantially rigid. In this preferred embodiment, the lip extends into the frame 4 on either end about 3.2 millimeters to a curved end of the two side walls 11, 12. At the top of the curved ends of each of the two side walls 11, 12, is a semicircular resting ridge 22, 23, which extends preferably about 1.6 millimeters from the edge of the two side walls 11, 12 along the same plane. The resting ridges 22, 23 function to ensure that the cartridge 1 does not rock when laid on a flat surface with the reverse side of the frame 4 facing toward the surface. The function of the resting ridges 22, 23 is necessary to consistently orient the capillary tubes 2 at a proper angle to a signal detection means when the cartridge 1 containing the capillary tubes 2 is inserted into a centrifuge, discussed hereafter, which permits exposure to the signal detection means discussed hereafter. Along the long side 9 are four openings 24 for receiving the distal ends of the capillary tubes 2 and extending from the long side 9 at each receiving opening 24 are the tabs 8 for protecting the tips of the capillary tubes 2. Each tab 8 extends preferably about 3.2 millimeters from the long side 9 at the same angle as the corresponding capillary tube 2, which extends through the receiving opening 24 on the long side 9 such that the tip of each tab 8 is substantially flush with the tip of each capillary tube 2. As depicted in FIG. 4, the front of the frame 4 has a bevel 25, 26 at either end of the exposure opening 7 positioned about 8 millimeters from the corners formed by the lip of the long side 9. Each bevel 25, 26 runs parallel to the long side 9, extends from each side wall 11, 12 to the exposure opening 7, and slopes at approximately a 45 degree angle for about 3 millimeters toward the obverse side of the frame 4 and toward the long wall 10. The bevels 25, 26 function to permit the long side 9 to support the distal ends of the capillary tubes via the receiving openings 24 such that they are parallel to the plane of the frame 4 while minimizing the use of plastic and additionally function to help ensure proper exposure of each capillary tube 2 to the signal generation and detection means discussed hereafter.

Turning again to FIG. 5 and FIG. 6, a pair of parabolically shaped female shafts 27, 28 can be seen. The female shafts 27, 28 comprise a parabolic element 29, 30, with the apex of the parabola pointing toward the long wall 10 and a bendable clip 31, 32 with a lip 33, 34. Each female shaft 27, 28, is preferably located about 6.4 millimeters from the long wall 10 and proximate to each side wall 11, 12 and extends away from the reverse side of the frame 4 for about 8 millimeters at a 90 degree angle. The bendable clips 31, 32 in combination with the lips 33, 34 function as a locking mechanism to attach the cartridge 1 via the female shafts 27, 28 to an apparatus discussed hereafter designed for use with the cartridge 1.

FIG. 4 shows the four capillary tubes 2 preferably coated with antigen. Each capillary tube 2 is preferably made of transparent silicon dioxide glass, more preferably borosilicate glass, and is about 10 millimeters to about 250 millimeters, preferably about 20 millimeters to about 150 millimeters, and more preferably about 35 millimeters long with an internal diameter of about 0.5 millimeters to about 1 millimeters, preferably about 0.65 millimeters. It should be noted that when the sample of a preferred embodiment is milk, an internal diameter of the capillary tube 2 smaller than a preferred value of 0.65 millimeters can be insufficient for the immunoassay, since aggregations of materials in the milk can clog the capillary tubes 2 and interfere with fluid flow. The capillary tubes 2 frictionally fit into the receptacle discussed hereafter at one end and slidingly fit into the passageways 6 of the frame 4 on the other end.

FIG. 7 is an exploded view of the top side of the holder 5, and FIG. 8 is an exploded view of the underside of the holder 5 for holding four capillary tubes 2 to be inserted into the frame 4. The holder 5 comprises a receptacle 35 and a cap 36. The receptacle 35 is preferably made of flexible Krayton® and comprises a flat rectangular support 37 preferably about 8 millimeters wide by about 3 centimeters long and about 1.6 millimeters thick, two guide openings 38, 39, and four collars 40 connected to the support 37. The collars 40 function to frictionally hold the capillary tubes 2 for insertion into the passageways 6 of the frame 4 with aid from the guide openings 38, 39 which slidingly engage the guide pins 15, 16 located on the protruding segment 13 of the frame 4. The diameter of the guide openings 38, 39 is about the same as the external diameter of the first guide pin 15 located on the protruding segment 13 of the frame 4, preferably about 3.4 millimeters. Each collar 40 has a narrow passageway 41 therein with an internal diameter sufficient to permit a capillary tube 2 to be inserted and held by friction therein, a cone 42 that functions as a guide for inserting the capillary tubes 2, and an opening 43 to permit insertion of the capillary tubes 2. The combination receptacle 35 and capillary tubes 2 slide into the frame 4 via the four openings 18 on the protruding segment 13. The collars 40 are of dimensions such that they can slidingly fit into the corresponding receiving chambers 19 of the frame 4 as referenced previously. For the purpose of description, the collars 40 can be divided into two pairs corresponding to the inner and outer pairs of the passageways 6 within the frame 4. The inner pair of collars 40 are preferably about 4.8 millimeters long and extend radially away from the center of the support 37 at the same angle as the corresponding inner pair of passageways 6 of the frame 4. The outer pair of collars 40 are preferably about 6.4 millimeters long and extend radially away from the center of the support 37 at the same angle as the corresponding outer pair of passageways 6 of the frame 4. The varying lengths of the collars function to extend the outer pair of radially oriented capillary tubes 2 such that the distal ends of all the capillary tubes 2 form a line parallel to the long side 9 of the frame 4 so that each capillary tube 2 penetrates each sample well discussed hereafter at an equivalent depth. Each collar 40 is preferably about 3.2 millimeters in diameter and flares out at the cone 42 about 3 millimeters from the end to the opening 43 which has an external diameter of about 4.8 millimeters and an internal diameter of about 3.2 millimeters.

FIG. 7 and FIG. 8 show the rectangular cap 36, preferably made of rigid polystyrene, for securing the receptacle 35 and capillary tubes 2 combination in the frame 4. The cap 36 can be of any dimension suitable to cooperatively engage the receptacle 35 and protruding segment 13 of the frame 4, but preferably comprises two long walls 44, 45, about 3.8 centimeters long by about 5 millimeters high; two short walls 46, 47 about 4.8 millimeters high by about 9.5 millimeters wide at the top sloping down to about 8 millimeters wide at the bottom; and a top 48 about 3.8 centimeters long by about a 9.5 millimeters wide. Located proximate to the short walls 46, 47 are two asymmetrical guide shafts 49, 50, a first guide shaft 49 and a segmented second guide shaft 50, each for slidingly engaging the guide pins 15, 16, respectively, on the protruding segment 13 of the frame 4 in combination with the guide openings 38, 39 of the receptacle 35. The first guide shaft 49 extends above the top 48 to form a ridge about 0.5 millimeters to about 3 millimeters, preferably about 1.5 millimeters high; has an internal diameter of between about 2.1 millimeters to about 5.1 millimeters, preferably about 3.1 millimeters or an internal diameter such that it slidingly engages the first guide pin 15 located on the protruding segment 13 of the frame 4; and is preferably between about 1.5 millimeters to about 5 millimeters deep or of a sufficient depth such that the top of the first guide pin 15 is flush with the top of the first guide shaft 49 when the two are cooperatively engaged as referenced previously. The segmented second guide shaft 50 extends above the top 48 to form a ridge about 0.5 millimeters to about 3 millimeters, preferably about 1.5 millimeters high; has an internal diameter of between about 2.1 millimeters to about 5.1 millimeters, preferably about 3.1 millimeters or of a sufficient diameter to slidingly engage the base of the segmented second guide pin 16 located on the protruding segment 13 of the frame 4, and extending from the end facing the space formed by the four walls 44, 45, 46, 47 to a ledge 51 located at about a half way point of the segmented second guide shaft 50. From the ledge 51 to the top end of the segmented second guide shaft 50, the segmented second guide shaft 50 has an internal diameter between about 1.7 millimeters to about 4.7 millimeters, preferably about 2.7 millimeters or a sufficient internal diameter to slidingly engage the upper portion of the segmented second guide pin 16 located on the protruding segment 13 of the frame 4. The segmented second guide shaft 50 is preferably between about 1.5 millimeters to about 5 millimeters deep or of a sufficient depth such that the top of the segmented second guide pin 16 located on the protruding segment 13 of the frame 4 is flush with the top of the segmented second guide shaft 50 when the two are cooperatively engaged as referenced previously. In any case, the segmented second guide shaft 50 should have a ledge 51 that defines two distinct internal diameters such that the segmented second guide shaft 50 is complementary to the corresponding segmented second guide pin 16 located on the protruding segment 13 of the frame 4 and can slidingly engage therein. The position of the asymmetrical guide shafts 49, 50 is such that they properly align with the guide pins 15, 16 and guide openings 38, 39. The difference of the dimensions of the two asymmetrical guide shafts 49, 50, functions to permit only one orientation for engaging the holder 5 comprising the cap 36 and receptacle 35 with the frame 4 as previously discussed. That is, the segmented second guide shaft 50 can only engage the segmented second guide pin 16 located on the protruding segment 13 of the frame 4 and cannot engage the first guide pin 15 similarly located. This ensures that the opening of a single port 54, discussed hereafter, located on the cap 36 faces away from the obverse side of the frame 4 when the holder 5 and the frame 4 are fully assembled to form the cartridge 5. Attached to the top 48 of the cap 36 is a trough 52 preferably about 2.2 centimeters long by about 1.6 millimeters wide and preferably about 1.6 millimeters deep and opens into the space created by the four walls 44, 45, 46, 47. The trough 52 is designed such that when it contacts the support 37 of the receptacle 35, it forms a sealed chamber so that the capillary tubes 2 are in fluid communication with each other. The seal is provided by an narrow oval ridge 53, shown in FIG. 8, that encircles the trough 52 about 2 millimeters from the edges of the trough 52 in this preferred embodiment, but can be any appropriate distance around the trough 52; and about 3 millimeters from the ends of the trough 52 and presses against the support 37 of the receptacle 35. Attached to the trough 52 at its center is a single port 54, shown in FIG. 7, with an internal diameter preferably about 3.2 millimeters which can be connected to a luer fitting discussed hereafter for pumping fluid through the chamber formed by the trough 52 and receptacle support 37. The single port 54 is about 8 millimeters long and is oriented such that its passage runs parallel to the horizontal plane of the top 48 while leading away from the trough 52 at a perpendicular angle as shown in FIG. 7. An opening 55 connecting the single port 54 to the trough 52 is located at the center of the trough 52 as shown in FIG. 7. Each longitudinal wall 44, 45 of the cap 36 contains three equally spaced rectangular openings 56 which fit over the three equally spaced clips 14 located on each of the lengthwise edges of the protruding segment 13 located on the frame 4 as discussed previously. The cooperation between the openings 56 and the clips 14 functions to secure the cap 36, receptacle 35, and capillary tubes 2 combination over the protruding segment 13 of the frame 4; with the aid of the guide pins 15, 16, the guide openings 38, 39, and guide shafts 49, 50; and with additional aid of the angle of the long cap walls 44, 45 formed by the short cap walls 46, 47. The combination frame 4, capillary tubes 2, receptacle 35, and cap 36 therefore comprise the cartridge 1 in this preferred embodiment.

FIG. 9 and FIG. 10 are perspective views of a preferred embodiment of the sample tray 3 which is preferably made of polypropylene. The sample tray 3 comprises four equally spaced wells 57 for holding aliquots of a fluorescently-labeled conjugate reagent and/or a sample, a reservoir 58 for holding fluid, such as liquid waste; and a molded cartridge storage compartment 59. The sample tray 3 forms a square preferably about 6 centimeters on all sides. The wells 57 are supported by a shelf 60. The shelf 60 extends from a wall 61 running the full width of the tray 3, and attached to two side walls 62, 63. The wall 61 from which the shelf 61 extends is about 6 centimeters long and preferably about 9.5 millimeters high. The two side walls 62, 63 are each preferably about 2.5 centimeters long and preferably about 1.4 centimeters high. The shelf 60 originates from the long wall 61 preferably about 1.6 millimeters below the top edge of the wall 61 such that a lip 64 is formed to aid in retention of any escaped liquid. The shelf 60 extends from the wall 61 at a slight downward angle that functions to guide escaped liquid to the reservoir 58 discussed hereafter and extends for about 9.5 millimeters and attaches to a wall 67 perpendicular to it which drops from it to the floor 68 of the reservoir 58 discussed hereafter. Each well 57 located on the shelf 60 has a parabolic shape with an internal diameter preferably about 8 millimeters and a depth preferably about 4.7 millimeters. Held within at least one well 57 is a metallic object comprising a stainless steel washer 65 for mixing. By passing a varying magnetic field under the washer 65, a dried fluorescently-labeled conjugate reagent resting on the bottom of the well 57 and optionally adhered to the bottom of the well 57, is reconstituted when a solution (optionally containing a sample) is added to the well 57. About a 4.8 millimeter diameter retaining ridge 66 is located along the opening to each well 57 and functions to prevent the washer 65 from falling out of the well 57.

The reservoir 58 is defined by a wall 67 which drops about 5 centimeters from the edge of the shelf 60, as discussed previously, to a floor 68; the portions of the side walls 62, 63 extending from the shelf 60, and a molded center wall 69 which rises preferably about 1.3 centimeters from the floor 68 such that it is about flush with the tops of the side walls 62, 63 and also forms part of the cartridge storage compartment 59 discussed hereafter. The reservoir 58 functions to contain fluid, discussed previously, passed through the capillary tubes 2 via the single port 54 on the cap 36 of the cartridge 1. The volume of the reservoir 58 is defined by the length and height of the wall 67 and distance from the wall 67 to the molded center wall 69 and should be of sufficient dimensions to contain an appropriate multiple of the combined volume of fluid capable of being contained by all the capillary tubes 2 contained within the cartridge 1.

FIG. 9 and FIG. 10 also show the molded cartridge storage compartment 59 which forms part of the sample tray 3. The compartment 59 is designed to form a molded contour around the cartridge 1 and securely retain the cartridge 1 within the sample tray 3 for storage and transportation as shown in FIG. 2. The compartment 59 is defined on its periphery by the molded center wall 69, a rear wall 70 opposite the center wall, two partial walls 71, 72, and a floor 73. The center wall 69 is molded to conform to the dimensions defined by the portion of the cartridge 1 comprising the long wall 10 of the frame 4, and the cap 36 secured on the protruding segment 13 of the frame 4 as shown in FIG. 2. At the center of the center wall 69 is a curved section 74 forming a half circle which curves toward the shelf 60 and is of such dimensions that it can slidingly receive the portion of the cartridge 1 defined by the single port 54 wherein the arc defined by the curve of the curved section 74 is substantially similar to the arc of the curve defined by the single port 54 such that the curved section 74 substantially forms a uniform contact with the periphery of the single port 54. The center wall 69 extends linearly on either side of the curved section 74, bends perpendicularly on either side towards the rear wall 70 to form a mold that encases the cap 36 of the cartridge 1, and bends again perpendicularly on either side towards and attaches to the two side walls 62 and 63. In this manner the center wall 69 forms a mold that substantially forms a uniform contact with the surfaces of the cartridge formed by the side of the cartridge 1 containing the holder 5. Located near to either edge of the curved section 74 and facing towards the rear wall 70 are a pair of fastening clips 75, 76 for securely holding the cartridge 1 within the storage compartment 59 in cooperation with the pair of retaining shelves 83, 84 discussed hereafter. The fastening clips 75, 76 are positioned at a height above the floor 73 such that they will engage the edge of the cap 36 comprising the corner formed by the front wall 44 and top 48 of the cap 36 of the cartridge 1 when the cartridge is positioned within the compartment 59 of the sample tray 3 with the reverse side facing the floor 73 as shown in FIG. 2. The two partial walls 71, 72 extend from the rear wall 70 for about 1 centimeter and are of the same height as the rear wall 70. At each corner formed by the partial walls 71, 72 and the rear wall 70 is a column 77, 78 extending from the floor 73 to the edge of the walls 70, 71, 72. Each column 77, 78 is adjacent to each corner at two sides, forms a side 79, 80 extending perpendicularly away from each of the partial walls 71, 72 and towards each other for a distance about the same as the distance from each of the corners formed by side 9 on the frame 4 of the cartridge 1 to the base of the outer pair of protective tabs 8, and angles towards the rear wall 70 at an angle corresponding to the angle of the outer pair of protective tabs 8 to form an angled side 81, 82. The columns 77, 78 function to hold the side of the cartridge 1 comprising the long side 9 of the frame 4 and protective tabs 8 extending from the long side 9, whereby the tips of the protective tabs 8 rest against the rear wall 70 and the corners of the long side 9 of the cartridge 1 rest against the column sides 79, 80 and the partial sides 71, 72 as shown in FIG. 2. Extending from each of the corners formed by the partial walls 71, 72 and the column sides 79, 80 is a narrow retaining shelf 83, 84 that forms a square with sides of equal width to the adjacent column side 79, 80 and positioned at a height above the floor 73 such that the obverse planer portion adjacent to the corners nearest the protective tabs 8 of the cartridge 1 rest against the underside of each of the retaining shelves 83, 84 so as to secure the cartridge 1 within the storage compartment 59 of the sample tray 3 as discussed previously and as shown in FIG. 2. Connecting the base of each of the corners formed by central wall 69 and short walls 62, 63 to the ends of the partial walls 71, 72 is a curved ledge 85, 86 that functions to aid removal of the cartridge 1 from the storage compartment 59. The curved ledges 85, 86 curve inward to form an arc complementary to the shape of human finger and rises above the floor 73 to a height sufficient for portions of the edges of the side walls 11, 12 of the frame 4 of the cartridge 1 to rest against the curved shelves 85, 86 when secured within the storage compartment 59 of the sample tray 3 as shown in FIG. 2. Extending inward from the rear wall 70 and along converging axis are three braces 87, 88, 89 for providing support for the cartridge 1 while positioned in the storage compartment 59 of the sample tray 3 by bracing against the obverse junctions of the receiving chambers 19 of the frame 4 and the edge of the lip formed by the long side 9 of the frame 4. The braces 87, 88, 89 are of dimensions that permit distal contact of the receiving chamber 19 junctions while providing a path for the narrow shafts 20. In a preferred embodiment shown, the three braces 87, 88, 89 comprise three narrow walls, but can also comprise three stubs along the rear wall 70 and three stubs to contact the junctions previously described. Along the outer edges of each of the external walls 62, 63, 70, 71, 72 is a lip 90 about 3 millimeters wide that aids the physical support of the sample tray 3.

FIG. 11 is a perspective view of another embodiment of a sample tray 103. The sample tray 103 comprises four equally spaced wells 157 supported on a shelf 160 for holding aliquots of a fluorescently-labeled conjugate reagent and/or a sample as in a preferred embodiment discussed above, and a reservoir 158, for holding fluid, such as liquid waste; defined by the shelf 160, three walls 162, 163, 170, and a floor 173. The sample tray 103 forms a square preferably of the same dimensions as a preferred embodiment of the tray 3 discussed previously. The two walls 162, 163 that run perpendicular to the shelf 160 are preferably about 1.4 centimeters high and the wall 170 opposite the shelf 160 is preferably about 9.5 millimeters high. Extending along the top edge of walls 162, 163, 170 is about a 3 millimeter lip 190 which aids physical support of the sample tray 103. The four wells 157 are located along the shelf 160 in an equally spaced manner, are preferably of the same dimensions as the wells 57 of a preferred embodiment previously discussed. The wells 157 preferably contain a stainless steel washer or disc 165 for mixing a dried reagent resting on the bottom of the well 157, optionally, the reagent can be coated on the washer. The reagent is reconstituted when a solution optionally containing a sample is added to the well 157. Wells contain a retaining ridge 166 similar to the retaining ridge 66 of a preferred embodiment previously discussed. The shelf 160 is preferably of the same dimensions as the shelf 60 of a preferred embodiment discussed above with a wall 167 extending to the floor 173 preferably similar to the corresponding wall 67 of a preferred embodiment discussed above.

In this alternative embodiment depicted in FIG. 11, the reservoir 159 is defined by the three walls 162, 163, 170, the shelf 167, and the floor 173 and, as stated above, similarly functions to contain fluid, such as liquid waste, as does the reservoir 59 of a preferred embodiment discussed above. Located preferably about 3.2 centimeters from the edge of the shelf 160 is a bevel 195 extending across the reservoir 159 from one side to the other 162, 163. The bevel 195 is preferably about 4.7 millimeters wide and slopes at about a 45 degree angle to form a second shelf 196 about 3.2 millimeters above the floor 173 and about 1 centimeter deep. The bevel 195 functions to prevent fluid, typically liquid, from being splashed against the rear wall 170 when the sample tray 103 is tipped. The cartridge 1 can also be stored in this embodiment of the sample tray 103 by laying it flat on the bottom 173 such that the protective tabs 8 face the rear wall 170. The cartridge 1 can be secured within the sample tray 103 by a plastic cover or by similar means.

FIG. 12 is a perspective view of a preferred embodiment of the apparatus 200 for use with the cartridge 1 and sample tray 3 combination of the present invention. FIG. 13 is a transparent view of a preferred embodiment of the apparatus 200 showing the critical internal components. Referring to FIGS. 12 and 13, the apparatus 200 comprises a prep station 201, a centrifuge 202 for drying the capillary tubes 2, a signal generation and detection station 203 for measuring a signal, an alphanumeric keypad controller 204 for permitting interaction between an operator and the apparatus 200, a liquid crystal display (LCD) 205 for displaying input and output messages and analytical results produced by a computing device discussed hereafter, and a printer 206 for printing a result.

Referring again to FIG. 12 and FIG. 13 the prep station 201 comprises a reservoir 207 for containing a fluid, a conduit 208 for transporting the fluid to a port 209, a syringe 210 for drawing sample to the port 209 and for pumping fluid from the reservoir 207 through the port 209; a first section comprising a previously referenced luer fitting 211 for attaching the single port 54 of the cartridge 1 to and for permitting fluid communication with the port 209 of the apparatus 200; a second section comprising a tray holder 212 for holding the sample tray 3, and a magnetic mixer 213 for mixing fluid in the wells 57. Magnetic mixer 213 is positioned under the tray holder 212 in such a manner as to align with the wells 57 of the sample tray 3 when the sample tray 3 is positioned in the tray holder 212. The centrifuge 202 is housed in a protective compartment 214 and comprises a disc capable of securely engaging the cartridge 1. The electromagnetic signal generation and detection station 203 comprises a signal generation means 215, such as laser or tungsten lamp suitable to emit an electromagnetic signal at an appropriate wavelength to cause a fluorescing compound in the sample-reagent mixture to become excited and fluoresce, and a signal detection means 216, such as a photon detector for detecting fluorescence, which photon detector can comprise a photomultiplier, phototube, photocell, or silicon diode, and preferably comprises a silicon diode.

FIG. 14a is a block diagram of the apparatus of a preferred embodiment of the invention showing cooperation among the electronic parts and FIG. 14b is a similar block diagram of the apparatus showing designations known to those of ordinary skill in the art of the various components. A logic and motor control printed circuit assembly (PCA) 300, hereafter referred to as a control PCA, functions to control and interface with the various components of the apparatus 200. A 40 wire ribbon cable 301 connected to two 40 position ribbon headers 302, 303 functions to connect the control PCA 300 to a prep station breakout PCA 304 for controlling the various components of the prep station 201.

The electrical components connected to the prep station PCA 304 comprise the following:

a syringe motor 305 for actuating and accurately controlling movement of the syringe 210, which syringe motor 305 is connected to the prep station PCA 304 via a first 8 position amplitude modulator 306;

a mixer motor 307 for actuating the magnetic mixer 213, which mixer motor 307 is connected to the prep station PCA 304 via a second 8 position amplitude modulator 308;

a lift motor 309 for moving the tray holder 212 to properly position the sample tray 3 under the cartridge 1, which lift motor 309 is connected to the prep station PCA 304 via a third 8 position amplitude modulator 310;

a valve 311 for controlling the direction of flow of the fluid contained in the reservoir 207, which valve 311 is connected to the prep station PCA 304 by 6 position amplitude modulator 312;

a syringe sensor 313 for monitoring the position of the syringe 210, which S syringe sensor 313 is connected to the prep station PCA 304 via a fourth 8 position amplitude modulator 314; a mixer sensor 315 for monitoring the position of the magnetic mixer 213, which mixer sensor 315 is connected to the prep station PCA 304 via a fifth 8 position amplitude modulator 316; and a lift sensor 317 for monitoring the position of the lift motor 309, which lift sensor 317 is connected to the prep station PCA 304 via a sixth 8 position amplitude modulator 318.

A 16 position amplitude modulator 319 connects the control PCA 300 to three additional PCA cards, a laser PCA 320 for controlling the operation of the signal generation means, which laser PCA 320 is connected to the control PCA 300 via a 6 position molex pocket header 321; a preamplifier PCA 322 for amplifying a photogenerated signal before processing by the control PCA 300, which preamplifier PCA 322 is connected to the control PCA 300 via a 5 position molex pocket header 323; and an barcode PCA 324 for interfacing with a commercially available barcode wand discussed hereafter, which barcode PCA 324 is connected to the control PCA 300 via a 4 position molex pocket header 325. An 18 position amplitude modulator 326 connects the various electrical components of the centrifuge 202 to the control PCA 300. The electrical components of the centrifuge 202 comprise a rotor motor 327 for rotating the centrifuge 202, a rotor door sensor 328 for detecting the opening of the door of the protective compartment 214, and a rotor home sensor 329 for aiding with determination of the position of the cartridge 1 while in the centrifuge 202 so as to permit proper presentation of the cartridge 1 to the signal generation and detection station 203. A 50 wire ribbon cable 330, connected to two 50 position ribbon headers 331, 332, connects a peripheral adapter PCA 333 that functions to interface with the alphanumeric keypad 204, the printer 206, the liquid crystal display 205, and an audio buzzer 334 for providing audible feedback to the operator about the functional status of the apparatus 200. A panel connector PCA 335 located at the rear of the apparatus 200 interfaces with an external DC power input connector 336, an RS-232 port 337, and a barcode wand input connector 338. The panel connector PCA 335 is connected to the control PCA 300 via a 10 wire ribbon cable 339 connected at each end to a 10 position ribbon header 340, 341; and via a power cable 342. Main power to the apparatus 200 is supplied via serial cooperation among a 110 vac input plug 343, a power entry module 344, a signal transformer 345, and an AC input cable 346 as shown in FIG. 14a and 14b. Two 2 position mini-fit molex connectors 347 connect the AC power cord 346 and the DC power cord 342 to the control PCA 300. The automated non-operator dependent portion of the apparatus 200 system software is provided by an erasable programmable read only memory (EPROM) module 348 connected to the control PCA 300 via a 30 position edge connector 349.

A Typical Immunoassay Using Preferred Embodiments of the Present Invention

FIG. 15 is a simplified representation of the solid-phase fluorescence immunoassay (SPFIA) of a preferred embodiment of the present invention. In a typical immunoassay using a preferred embodiment of the present invention, the cartridge 1 and sample tray 3 are placed on the prep station 201 by the operator as shown in FIG. 12, then 100 microliters of a sample possibly containing an analyte of interest, such as milk suspected of containing β-lactam antibiotics, is added to one or more wells 57 located in the sample tray 3 which contain a dried stabilized reagent comprising an antibody to the analyte of interest, which antibody is conjugated with a highly fluorescent label, such as a cyanine dye (Cy-5®), fluorescein isothiocyanate (FITC), rhodamine, Texas Red, phycoerythrin, and allophycoerythrin or any other compound with a sufficient quantum yield or efficiency to produce appropriate fluorescence and that will not interfere with any reactions of the immunoassay; or with a bio-luminescent compound. A barcode, provided with the cartridge 1 and sample tray 3 combination kit, is then scanned using a standard commercially available barcode wand associated with the barcode wand input connector 338 to provide calibration information to the apparatus 200. For example, the barcode can contain the pass/fail threshold level of fluorescence for a particular immunoassay. The operator then inputs additional information via the alphanumeric keypad controller 204 and subsequently starts the apparatus 200. The sample and fluorescently-labeled conjugate reagent are then mixed while in the well 57 by the application of a magnetic field provided by the magnetic mixer 213 located under the tray holder 212 of the apparatus 200, such that the metallic washer 65 flips, rotates or agitates to appropriately mix the sample and conjugate reagent combination for a sufficient time for the fluorescently-labeled conjugate and the analyte to bind. The cartridge 1 is connected via the single port 54 on the cap 36 of the cartridge 1 to the luer fitting 211 of the prep station 201 of the apparatus 200 and positioned above the sample tray 3 with the obverse side of the cartridge 1 facing the reservoir 58. Within the cartridge 1 each capillary tube 2 has at least a portion of the internal surface coated with antigen analogous to or mimetic of the analyte of interest. The sample tray holder 212, and thereby the sample tray 3, is lifted by the lift motor 309 so that the tips of the capillary tubes 2 contact each sample and fluorescently-labeled conjugate reagent mixture in the wells 57. The sample tray 1 is oriented in a manner which permits the cartridge 1 to be positioned such that the capillary tubes can penetrate the sample and fluorescently-labeled conjugate reagent mixture at a sufficient depth and at a sufficient angle to draw a sufficient amount of the sample and fluorescently-labeled conjugate reagent mixture into each capillary tube 2. The sample and fluorescently-labeled conjugate reagent mixture is then drawn into the capillary tube via capillary action and suction applied by the syringe 210 to the single port 54 on the cap 36 of the cartridge 1, and is then allowed to incubate for a period of time in one or more capillary tubes 2 during which a percentage of fluorescently-labeled conjugate not bound to the analyte, will bind to the antigen comprised by the substrate comprising the capillary tube 2 walls. If there is a relatively large amount of analyte in the sample, very little fluorescently-labeled conjugate will bind to the substrate of the capillary tube 2 walls and if there is a relatively small amount of analyte in the sample a large amount of fluorescently-labeled conjugate will bind to the substrate of capillary tube 2 walls.

After the incubation period, a liquid residing in the reservoir 207 of the apparatus 200 is pumped by the syringe 210 through each capillary tube 2 via the luer fitting 211 and the single port 54 located on the cap 36. The liquid then enters the chamber created by the trough 52 and receptacle support 37 and subsequently enters each capillary tube 2. The liquid stops the reaction and washes excess fluid out of each capillary tube 2. Prior to or simultaneous with the pumping of the liquid into each capillary tube 2, the lift motor 309 orients the sample tray holder 212, and thereby the sample tray 3, such that the capillary tubes 2 are positioned over the reservoir 58 within the sample tray 3, so that the fluid pumped out of each capillary tube 2 is expelled into the waste reservoir 58 of the sample tray 3. The sample tray 3 is then discarded and the cartridge 1 is inserted into and dried by the centrifuge 202 located on the apparatus 200 for use with the cartridge 1 and sample tray 3 combination. After drying and while in the centrifuge 202, the cartridge 1 is positioned in front of the signal generation means 215, such that the exposure opening 7 of the frame 4 permits the signal generation means 215 to emit a signal that substantially penetrates the capillary tube 2. The signal detection means 216 positioned adjacent to the signal generation means 215 then detects any fluorescence emitted by the bound conjugate containing the fluorescent label. This signal is then processed by the computing portion of the apparatus 200 and the presence of analyte, alternatively the amount of analyte present is determined where analyte concentration is inversely proportional to the level of fluorescence for this preferred embodiment (a competitive assay). FIGS. 16a–d to FIGS. 17a–b show plots of normalized fluorescence versus concentration of six β-lactam antibiotics in parts per billion at different levels of concentration. A least squares polynomial fit of the curves generated by the multiple points can be used by the apparatus 200 to provide a quantitative result, wherein the computing portion of the apparatus 200 interpolates the amount of analyte in the sample by plotting the observed level of fluorescence on the appropriate calibration line for the particular analyte and identifying the corresponding concentration for that level of fluorescence.

It should be noted that in a presently preferred embodiment of the present invention, the operator only carries out the steps of placing the sample tray 3 in the sample tray holder 212, adding sample to the sample tray 3, optionally scanning the barcode, starting the apparatus 200, moving the cartridge 1 to the centrifuge 202, and discarding the cartridge 1 and sample tray 3. The apparatus 200, performs all the other steps of the immunoassay discussed above.

Alternative Embodiments and Variations of Preferred Embodiments

Although the present invention has been described in considerable detail with reference to a preferred embodiments thereof, other embodiments are possible. For example variations of either one or all of the immunoassay chemistry used, the cartridge and sample tray design, and the design of the apparatus for use with the cartridge and tray combination are possible within the scope of the present invention.

A preferred variation for the immunoassay chemistry is simply to reverse the label and binding member in the competitive fluorescence immunoassay of a preferred embodiment of the invention. That is, the fluorescently-labeled conjugate reagent can contain an antigen analogous to or mimetic of the analyte, wherein the antigen is conjugated with the fluorescent label; and the antibody to the analyte is coated onto the surface of the capillary tubes. In this case, the fluorescently-labeled antigen conjugate competes with the analyte antigen for binding sites on the antibody coated on the surface of the capillary tubes. As in the competitive fluorescence immunoassay of a preferred embodiment of the present invention, the level of fluorescence will be inversely proportional to the amount of analyte in the sample.

In addition to the competitive fluorescence immunoassay of preferred embodiments described above, a non-competitive sandwich fluorescence immunoassay can also be used. In this case, the sample is mixed with a fluorescently-labeled conjugate reagent and drawn into the capillary tube. The analyte binds to the conjugate and to a capture binding member on the substrate which comprises a surface of the capillary tube. The capillary tube is washed, optionally dried, and exposed to a signal generation means and signal detection means to measure the level of fluorescence. In a sandwich immunoassay such as this, the amount of fluorescence is directly proportional to the amount of analyte in the sample.

While an immunoassay described above as a preferred embodiment is a competitive inhibition immunoassay employing a fluorescent label, other immunoassay methods can also be employed. These include ELISA sandwich immunoassays wherein an analyte sample is mixed with free antibody to the antigen and subsequently washed and further mixed with an enzyme linked antibody specific to a different epitope on the analyte. Any free antibody is then washed away and an enzyme substrate is added to complex with the enzyme mixture. Detection of the analyte can then be effectuated colorimetrically or via other means whereby the level of the signal is positively correlated to the concentration of analyte detected.

As noted above, variations on the immunoassay can include different labels, such as enzymes for use in a non-competitive immunoassay. Similarly, an enzyme label can be used in a competitive immunoassay whereby detection of a signal generated by a UV lamp occurs via a UV absorbance detector and the absorbance reading is negatively correlated with the concentration of analyte in the sample. Alternatively RIA immunoassays known to those of ordinary skill in the art can be used with an appropriate embodiment of the present invention.

The dimensions of the cartridge and sample tray can vary from that already described depending on the particular application and use. All that is required are dimensions appropriate for use with an apparatus comprising any analytical instrument sufficient to effectuate the chosen immunoassay. For example, these dimensions include a length of capillary tube sufficient to contain an amount of a substrate and sample mixture, a cartridge comprising a region suitable to expose at least a portion of each tube to an emitted signal, and a sample tray with wells therein sufficient to contain sample and reagent solution. Furthermore, a reservoir can optionally be included with a waste disposal means comprising a vacuum system connected to the cartridge for instance, wherein the evacuation product of the capillary tube contents are contained in a separate container or chamber.

In many cases, the apparatus, the cartridge or tube design will depend on the type of immunoassay employed, instrumentation with which the subject interacts, and conditions under which the subject is used. Immunoassays that can be adapted for use with the present invention or variations thereof include ELISA, RIA, and FIA as discussed previously, but can also include other bioassays, including but not limited to various other immunoassays utilizing different labels, such as enzymes, isotopes, fluorescent and bio-luminescent compounds, physical constructs, reactants; and other bioassays appropriate for use in capillary tubes. Instrumentation can include custom or commercially available analytical instruments including, but not limited, to spectrophotometers, chromatographs for collection fractions from the immunoassay, counters, densitometers, diagnostic instruments, and forensic instruments; and other instruments necessary for use with a particular embodiment of the present invention. Conditions for use include, but are not limited to, clinical laboratories, use in the field, such as outdoors and/or in agricultural, dairy, and industrial settings; and in research or crime laboratories. Alternative embodiments of the present invention can thus be used to adapt to the above uses, conditions for use, and cooperation with other devices.

The cartridge can comprise substantially one piece with the coated capillary tubes frictionally sealed within the cartridge. Alternatively, the capillary tubes can be sealed within the cartridge by a means other than by friction, such as an adhesive sealant. The capillary tubes can be spaced apart linearly rather than radially. In this case, drying preferably occurs via a means other than by centrifugation, such as by air drying, by purging with a gas, such as nitrogen; or by vacuum. The cartridge can have a plurality of chambers each independently connected to each capillary tube. In this case an even greater diversity of immunoassays can be carried out in each capillary tube, including the use of different detectable events and detection means. Protection of the capillary tubes can also be accomplished by various means, such as use of a hinged cover that can be optionally positioned over the tips of the capillary tubes and moved away from the capillary tubes when fluid is drawn or added to the capillary tubes, or the capillary tubes can be retractable into and out of the cartridge. The region of the cartridge for exposing each capillary tube to a signal detection means can also be designed so that only one side of the cartridge is open since, in the case of fluorescence imrnmunoassays, the signal generation means and signal detection means can be adjacent to each other. Additionally, a clear plastic cover can be located over the exposure opening 7 to protect the capillary tubes from damage.

One embodiment of a one piece design is a cartridge wherein the capillary tubes are linearly spaced apart within the cartridge with a central opening for exposing them to a signal detection means. On one side of the capillary tubes can be a receiving chamber for receiving a sample, such as milk. A syringe on the other side of the capillary tubes can be used to draw sample into the capillary tubes. To conduct the immunoassay sample in the receiving chamber is placed in contact with the capillary tubes by passageways that connect to individual reagent chambers in fluid communication with each capillary tube. The reagent chambers can contain reagent such that backward engagement of the syringe can draw sample into these chambers and stop to permit mixture of sample and reagent in each chamber by magnetic or other means discussed herein or known to those of ordinary skill in the art. Backward engagement of the syringe can then continue and be used to draw the reagent sample mixture from the mixing/reagent chamber and into the capillary tubes for incubation and an immunoassay reaction to occur. The same syringe can be used to push a fluid into the capillary tubes via a passage connected to the distal end of each capillary tube, wherein a third chamber containing wash fluid for instance, can be opened via a valve or puncture means such that forward engagement of the syringe forces the fluid into the passageway and through each capillary tube. In this embodiment a drying step would not be required.

The cartridge can also be of an entirely different shape. For example, the cartridge can comprise a disc wherein the capillary tubes are spaced radially throughout the disc and a sample can be added to chambers at the periphery of the disc in such a manner that sample can be drawn into each capillary tube and expelled into the first chamber by pumped fluid added to the tubes via a port at the center of the disc; or other variations of a circular cartridge.

Similarly, a circular disc can be used wherein the sample is added to a first chamber near the center of the disc. Upon application of centrifugal force, the sample, which can also react with a reagent in the first chamber, can be drawn into capillary tubes or passageways radially spaced apart within the disc wherein one or more second chambers at the periphery of the disc and fluidly attached to the capillary tubes can collect excess fluid or provide for further reaction steps. Variations of this embodiment can include additional capillary passageways and/or chambers. Alternatively the cartridge can be shaped like a pie wedge such that a plurality of cartridges can fit together to form a circle for drying in a centrifuge or for permitting reactions to occur as previously described.

Another embodiment is a "Gatling gun" design wherein the capillary tubes are spaced apart along the outside of the longitudinal side of a cylinder or by a disc or plurality of discs containing openings to hold a plurality of spaced apart capillary tubes in a circular manner. In this case the cylinder can rotate to present a particular tube to a sample source or to a fluid source for washing, adding reagent, or other desired fluid to each tube. The cylinder can also rotate to present a capillary tube to a signal generation and detection means. Alternatively, the cylinder can cooperate with a multiwelled circular sample tray for serial or simultaneous sample removal and/or washing and expelling of fluid and even multiple signal generation and detection means. The circularly spaced apart capillary tubes can encircle a central syringe that is in fluid communication with the capillary tubes and draws fluid into the capillary tubes and/or advances fluid from the capillary tubes into any chambers and/or reaction sites on the surface of the capillary tubes.

The cartridge can also comprise a substantially rectangular shape where a plurality of capillary tubes are proportionately spaced apart and arranged in two rows; e.g. tubes are spaced in a cartridge that has an exposure opening on each side, which thereby permits simultaneous detection of analyte in two or more samples. In this embodiment, two pairs of signal generation and signal detection means can be simultaneously used, wherein the cartridge is designed such that each row of capillary tubes can be simultaneously or independently contacted by signal generation and signal detection means when mounted on an appropriately designed apparatus, such as an analytical instrument.

The cartridge can also be made of different types of plastic such as, polyvinyl chloride, polyethylenes, polyurethanes, polystyrenes, polypropylenes, and other plastic materials. The capillary tubes can also optionally be made of plastic such as polyvinyl chloride, polyurethanes, polystyrenes, polypropylenes, polyethylenes and other plastic materials commonly used to form capillary tubes or tubing. Preferably, the chosen material not interfere with either the chemistry of the immunoassay or any analytes or products thereof, or the signal generation and detection means. Preferably the chosen material provides for an inexpensive and therefore disposable cartridge design.

The sample tray can also vary from preferred and an alternative embodiment described above. It can have more than 4 sample wells, larger or smaller sample wells, and even multiple waste reservoirs or other chambers. Alternatively the waste reservoir can comprise a sponge or similar absorbent material. It can also comprise a vacuum system fluidly attached to a waste reservoir as previously discussed, and of various materials, with preference to inexpensive materials as discussed previously for the cartridge.

Variations of preferred embodiments of the apparatus for use with a preferred cartridge and sample tray combination as disclosed herein are also possible within the scope of the present invention. An important aspect of an alternative embodiment of the apparatus for use with a preferred embodiment of the cartridge and sample tray is that embodiments of the apparatus are able to communicate with the cartridge and sample tray, that the apparatus is equipped with appropriate electronics and/or optics for a given immunoassay, and that the apparatus is capable of performing or interfaced with an instrument capable of performing an automated immunoassay and of computing qualitative, semi-quantitative, and/or quantitative results. Another aspect of the apparatus for use with a preferred embodiment of the cartridge and sample tray combination is that the apparatus house or control a suitably substantial portion of the means to move fluid in and out of the wells, capillary tubes, and chambers.

Aspects of an alternative embodiment of the apparatus for use with alternative embodiments of the cartridge and sample tray will vary depending on the design of alternative embodiments of the cartridge and sample tray, but preferably effectuate an immunoassay in capillary tubes, and is preferably relatively simple, rapid, reliable, and requires minimal operator interaction.

Several variations of a preferred embodiment of the apparatus of the present invention can be employed for use with a fluorescence immunoassay or other immunoassays. A vacuum system can be employed in place of a syringe within or in cooperation with the apparatus to remove fluid from the capillary tubes and/or the sample tray. Similarly, the means to mix the sample and reagent can be other than by magnetic field such as agitation by vibration or by physical mixing.

Various types of spectroscopic hardware can also be employed. Such variations are dictated by the immunoassay, analyte of interest, and other criteria and would be obvious to one of ordinary skill in the art. These variations include, but are not limited to, use of different signal generation means, including, but not limited to, argon lamps, xenon lamps, hydrogen lamps, deuterium lamps, tungsten lamps, nernst glower, nichrome wire, globar, and hollow cathode lamps or other appropriate signal generation means capable of providing emitted signals covering appropriate wavelengths in one or more regions of ultraviolet, visible, near infrared, infrared, and far infrared light; various wavelength selectors including, but not limited to, filters, including interference filters and glass absorption filters, and monochromators, including prism monochromators, such as fluorite prism, fused silica or quartz prism, glass prism, sodium chloride prism, and potassium bromide prism; and gratings; and various signal detection means including, but not limited to, photomultipliers, phototubes, photocells, silicon diodes, and semiconductors.

Variations to the signal processing means can also be employed to provide quantitative results, such as constant automatic calibration of the signal generation and detection means, use of a more sophisticated analog to digital converter, use of multi-level calibration curves, e.g. a least squares fit of curves such as those shown in FIGS. 16a–d to FIGS. 17a–b, and data reduction and analysis that includes statistical analysis. The apparatus can also include a computer disc drive for loading a computer disc for storing a result provided by the signal processing or computing means in a computer storable file. The result can be transmitted via the RS-232 port on the apparatus to an external computing or storage device for more sophisticated data reduction and analysis. It should be noted that use of an erasable programmable read-only memory (EPROM) module, as in a preferred embodiment of the apparatus of the present invention, makes it relatively simple to modify the software of the apparatus to adapt it to various immunoassay formats, levels of data reduction and analysis, and interaction with external and/or internal devices and/or components.

Alternative embodiments of. the apparatus of the present invention can also include various levels of automation. One embodiment of the apparatus of the present invention can be designed such that only instrument control is possible with the stand alone apparatus and all data reduction and analysis is performed by a computer connected or networked to the apparatus via a port, such as RS-232, IEEE-488 (HP-IB), contact closure, and the like. Similarly, control of the apparatus can be automated by a connection to a computer as previously described where all control inputs are directed by the computer and initiated by an operator or alternatively by a computer program.

Additionally, a preferred embodiment of the apparatus of the present invention or variations of it can be interfaced with laboratory robots, such as cylindrical, cartesian, and articulated robots and the like; to enable complete automation of the immunoassay. The robotics device can be programmed to remove sample from a central container and add it to each well and alternatively to perform any pre-assay sample processing and preparation necessary, such as filtration, extraction, dilution, removal of certain components, and other manipulations depending on the sample. The robotics device can also place the sample tray and cartridge on the apparatus and subsequently move the cartridge to the centrifuge or other device and dispose of the sample tray. The robotics device can be integrated into an alternative embodiment of the apparatus of the present invention or it can be a commercially available robot for use in the laboratory and known to those of ordinary skill in the art of the present invention.

EXAMPLES

Example 1—Capillary-Tube Surface Preparation

The surface of borosilicate, glass capillary tubes (Drummond Scientific, Broomall, Pa.) was treated with a silanizing reagent in accordance with the process for Aquasil® silanization coating in accordance with Example 9, coating with a protein substrate conjugated to a reactive protein, blocking the capillary tubes, and drying and incubating. The lengths of individual capillary tubes were 3.5 centimeters (cm) with an inner diameter of 0.65 millimeters (mm) and an outer diameter of 1 mm. By using these capillary tubes, one achieves a high surface area to volume ratio and minimizes the use of reagents. Other capillary tube dimensions can be used.

The high surface area to volume ratio allowed for a short two-minute incubation. Tubes having other inner diameter dimensions were also examined, however, the 0.65 mm inner diameter tubing was found to be most useful with fresh, raw milk samples, which often contain fat globules that can be as large as several hundred micrometers ($\mu$m). Such fat particles can potentially clog the capillary tube channels if tubes of smaller inner diameter were used. Additionally, the transport of reactants to the interior surface of the tube, where the measurable binding reaction occurs, is strictly through diffusion. Therefore, potential problems due to irreproducible agitation are eliminated.

Example 2—Synthesis of Antigen Conjugates for Coating Capillary tubes.

The antigen conjugates, for coating onto the surface of the capillary tubes, were prepared by binding the appropriate β-lactam drug, such as Penicillin G, Ampicillin, Cloxacillin, Cephapirin, Ceftiofur, Amoxicillin and the like; to a carrier protein either bovine serum albumin (BSA) or a polypeptide copolymer consisting of lysine and alanine subunits (Sigma Chemical Co., St. Louis, Mo.). The covalent linking of antigen to carrier protein was accomplished through the use of conventional homobifunctional or heterobifunctional linkers, such as Succinimidyl 4-(N-maleimidomethyl) cyclohexane-1-carboxylate (SMCC), Bis (sulfosuccinimidyl) suberate, and 1-Ethyl-3-(3-Dimethylaminopropyl)-carbodiimideHydrochloride(Pierce Chemical Co., Rockford, Ill.) in accordance with the process provided by the manufacturer.

Example 3—General Procedure for Coating Antigen-Conjugate on the Surface of Capillary Tubes.

After the silanizing surface treatment, the capillary tubes were incubated for from about 30 minutes to 24 hours in a buffered solution of the antigen-conjugate (20–40 µg/ml). The incubation temperature was usually 4–7° C., although occasionally room temperature incubation was used. The capillary tubes were removed, washed with distilled water, dried in a stream of compressed air, and then incubated in a solution of bovine-serum albumin (0.1% BSA in PBS-phosphate buffered saline-pH=7.2, 0.05% Proclin 300 (Supelco) a biocide) for 1 hour at room temperature. The purpose of this incubation with BSA was to block any solution regions of the surface that were not coated by the antigen-conjugate. The tubes were again removed, washed with distilled water and dried in a stream of compressed air (20–30 psi). They were stored in the dark, at room temperature in a sealed, foil pouch with an indicating desiccant package. Maintaining dry and dark conditions were important to maintain the stability of the coated capillary tubes.

Example 4—Preparation of Fluorescent-labeled Antibody Conjugates a. Antibody Production.

Antibodies to the antibiotics in the penicillin family were produced by immunizing goats with a conjugate of keyhole limpet hemocyanin (KLH) (Sigma Chemical) and ampicillin (Sigma). Ampicillin was used because it has an amino-group available for conjugation. The resulting bleeds were screened for cross-reactivity with penicillin G, ampicillin, cloxacillin and amoxicillin (Sigma). The cross-reactivity of this antibody with penicillin G and ampicillin was comparable, while the cross-reactivity for cloxacillin and amoxicillin was approximately 50% less. This antibody also exhibited less than 1% cross-reactivity with ceftiofur (UpJohn Inc.) and cephapirin (Sigma). Antibodies to ceftiofur were developed by immunizing goats with KLH-ceftiofur. A monoclonal to cephapirin was developed using conventional techniques with KLH-cephapirin as the conjugate. Enzyme immunoassay studies indicated that the cross-reactivity of the ceftiofur antibody to the other five β-lactam drugs of interest was less than 1%. The cross-reactivity of the cephapirin antibody to the other five β-lactam antibiotics was less than 0.1%.

b. Fluorescently-Labeled Antibody Conjugate Production.

Monoclonal and polyclonal antibodies were prepared using conventional purification techniques as taught by C. Schmidt, 1989, "The Purification of Large Amounts of Monoclonal Antibodies," Journal of Biotechnology, Volume 11, pp 235–252. Using the fluorescent label Cy-50®, Cy-5®-antibody conjugates were prepared using the protocols previously published and provided by the manufacturer (Biological Detection Systems, Pittsburgh, Pa.). The Cy-5® fluorescent label, available with an NHS ester functionality, was linked to amino groups of the antibody. Purification and isolation of the conjugated dye was performed through chromatography. Spectroscopic examination indicated that the number of Cy-5® dye molecules that were bound to each antibody molecule was usually between two and four. The ratio of antibody molecule to Cy-5® molecule is controlled by modifying reaction conditions such as time of conjugation and/or ratio of Cy-5® concentration to antibody concentration in the reaction mixture. Batch to batch studies indicated that there was no significant increase in fluorescence intensity with increase in the number of Cy-5® molecules per antibody molecule. In fact, the fluorescence intensity often decreased when the fluorophore/antibody ratio was greater than four. This phenomenon was especially apparent when using monoclonal antibodies. It is unclear at this time whether this decrease was due to increased quenching with high loading of the fluorophore or due to decreased antibody binding affinity resulting from inactivation of the antibodies' recognition sites.

Example 5—Process for Analysis for Analytes in Samples

Immunoassay Protocol (a) A measured amount of fluorescently-labeled conjugate, comprising antibody-Cy-5200 conjugate (preferably dried, e.g. lyophilized or air dried,) was combined with a sample of milk in a small container, such as the well of a microtiter-plate. The raw milk sample and antibody conjugate were mixed on a vibratory shaker for 10 seconds.

(b) The solution from (a) was then sipped into the appropriate capillary tube through the use of a manifold device, such as a modified pipettor or an embodiment of the cartridge of the present invention.

(c) The solution was then incubated, while in the capillary tube, for a time sufficient to react with the antigen attached to an interior surface of the tube, e.g. for 2 minutes.

(d) All reagents were then washed out of the capillary tubes with flowing distilled water from the end opposite from which the solution was brought in. The reagents were then dried with a stream of compressed air (20–30 psi).

(e) The fluorescence intensity of the tubes was then measured using a fluorometer equipped with a 3 mW semiconductor-diode laser (λmax=635nm, TOLD 9521 (s), Toshiba, Japan) signal generation means, appropriate optics to filter the signal, and a current response of a silicon p-i-n junction diode to generate an analog photocurrent. The resulting photocurrent was amplified, converted from an analog to a digital signal, and processed on a computer to determine the presence of analyte and semi-quantitatively measure an amount of analyte in a sample.

Processing via a computer involved comparing the fluorescence level of the detected signal with dose response curves as shown in FIG. 16a–16d and FIG. 17a–17b. A normalized fluorescence signal is located on the y-axis and the relative concentration in parts per billion was located on the x-axis. Table I shows U.S.F.D.A. safe/tolerance levels for the six β-lactam drugs in milk.

Example 6—Preparation of a Capillary tube for Use in a Competitive Immunoassay to Detect Cephapirin in Milk A borosilicate glass capillary tube having a length of 65 mm and an inner diameter of 0.6 mm (Drummond Scientific) was washed with distilled water and then dried under a stream of air until substantially all of the distilled water had evaporated from the surfaces of the capillary tube. The capillary tube was then incubated in a 2.5% aminopropyl triethoxysilate ethanol solution for 20 minutes at 80° C.

The incubated capillary tube was then washed with distilled water and dried in a stream of air. The dried capillary tube was then incubated for 2 hours at 120° C. After incubation, the capillary tube was cooled to room temperature.

The capillary tube was then incubated in the presence of a buffer solution comprising a conjugate of Cephapirin-Bovine Serum Albumin (BSA) conjugate. The cephapirin-BSA conjugate was prepared by combining 65 mg Cephapirin, 46 mg EDC (1-ethyl-3-(3-dimethylaminopropyl)-carbodiimide) and 26 mg of N-HS (N-hydroxysuccinimide) (Pierce Chemical) in a 16×100 mm glass tube. 1 ml DMF (N,N dimethylformamide) (Fisher Scientific) was added to the tube and the contents of the tube were stirred at room temperature for 30 minutes. 100 mg BSA was dissolved in 3 ml 20mM potassium phosphate buffer, pH 7.2, in a separate 16×100 glass tube. The Cephapirin solution was combined with the BSA solution and stirred at room temperature for 1 hour. The Cephapirin-BSA conjugate was purified with a gel filtration column (Sephadex G-25) using 20 mM potassium phosphate buffer, pH 7.2, as the equilibration and elution buffer. The capillary tubes were incubated in the resultant Cephapirin-BSA conjugate for 3 hours, during which time the Cephapirin-BSA conjugate became bound to the capillary tube surface. After incubation, the capillary was washed with distilled water and dried under a stream of air.

The capillary tube was then incubated at 25° C. for 2 hrs in a blocking solution of 10% sucrose, 0.1% bovine serum albumin and 0.05% proclin 300 in order to block any free binding sites of the capillary tube surface not occupied by the antigen. After incubating the capillary tube in the blocking solution, the capillary tube was washed with distilled water and dried under a stream of air.

Example 7—Preparation of Anti-Cephapirin-Cy-5® Conjugate 1 milligram of activated Cy-5® dye (Biological Detector Systems) dissolved in 0.2 ml of 20 mM potassium phosphate buffer, pH 7.2 was combined with 2 ml of a Cephapirin antibody solution (4 mg/ml Cephapirin antibody in 20 mM potassium phosphate buffer at pH 7.2). Cy-5® dye/Cephapirin solution was then stirred at room temperature for 1 hour. The resultant Cy-5®-Cephapirin conjugate was purified on a gel filtration column (Sephadex G-25), where 20 mM potassium phosphate buffer, pH 7.2, was used as both the equilibration and elution buffer.

Example 8—Manual Immunoassay of Milk Suspected of Comprising Cephapirin

About 4 to 5 µl of antibody conjugate solution, as prepared in Example 7, was added to 0.5 ml of milk suspected of comprising Cephapirin, resulting in an overall conjugate concentration in the milk of 10 µl/ml. The milk conjugate mixture was then incubated for a few seconds.

One end of the prepared capillary tube from Example 6 was dipped into the incubated milk. A 10 µl plug of milk was taken up into the capillary tube under capillary force. Milk also coated the exterior of the capillary tube up to about 20 mm.

The capillary tube was then turned upside down so that the 10 µl plug of liquid moved down the capillary tube into a region in which the outer surface of the capillary tube had not contacted the milk. The sample plug was incubated in the capillary tube for 1 minute to allow the reaction to proceed to provide a detectable fluorescent signal for a positive sample.

The plug was then washed from the capillary tube with 100 µl of distilled water. After washing the capillary tube, the capillary tube was dried with a stream of air from an air gun.

The capillary tube was then irradiated with a laser, where the wavelength of light form the laser was 632.8 nm. Upon irradiation, a highly intense emitted signal having a wavelength of 667 nm was detected. The intensity of the emitted signal indicated that no cephapirin was present in the assayed milk.

Example 9-Method for Coating 4-Amino-Penicillinic Acid on a Capillary Tube

AquaSil® Silanization Coating

One or more glass capillary tubes was immersed in a 0.2% AquaSil®-octodecyltriethoxy silane (Pierce Chemical #42797) deionized water solution in a manner that ensured a complete coating on the desired portions of the capillary tubes and then incubated in the solution for 40±30 minutes at room temperature. The capillary tube was then placed in the centrifuge and centrifuged at 1000 rpm for 10±5 minutes to spin dry the capillary tube. Alternatively, the capillary tube may be air dried, dried with a gas, or an suitable means to sufficiently dry the capillary tube.

The AquaSil® coated capillary tube was then placed into a 125±10° C. oven for 60±10 minutes. Next, the capillary tube was allowed to cool to room temperature and subsequently stored in a desiccated, foil ziplock bag at room temperature until further coating was required. The capillary tube is stable for long periods in this storage condition.

BSA-Biotin Capillary Tube Coating

The AquaSil® coated capillary tube was immersed into a BSA-biotin (bovine serum albumin) solution consisting of a stock BSA-biotin solution (Sigma #A-3294) at 200 µg/mL diluted 1:200 with 20 mM phosphate buffered saline (PBS)-pH 7.2. 100 mL of the 20mM PBS-pH 7.2 solution can be prepared by mixing 268 g potassium phosphate-dibasic ($K_2HPO_4$) (Fisher #P284-3), 60.2 mg potassium phosphate-monobasic ($KH_2PO4H_2O$), and 875 mg sodium chloride (Fisher #P285-3) where the pH was 7.2±0.1.

After it was ensured that all desired areas were contacted with solution, the BSA-biotin coated capillary tube was then incubated in solution for 1–24 hours at room temperature. After incubation, the BSA-biotin coated capillary tube was centrifuged at 1000 rpm for 10±5 minutes to spin dry the capillary tube. The BSA-biotin coated capillary tube was then stored in a desiccated, foil ziplock bag at 4° C. until further coating was required. The capillary tube was stable for long periods in this storage condition.

Bovine Serum Albumin Blocking of Capillary Tubes

The BSA-biotin coated capillary tube was immersed in a 0.1% BSA/10% sucrose blocking solution. The 100 ml of the 0.1% BSA/10% sucrose blocking solution can be prepared by mixing 10 g sucrose (Fisher #S-53) with 80 mL deionized water, mixing the solution to dissolve the sucrose, adding 100 mg BSA (Sigma #A-3294) to the sucrose solution, slowly mixing the sucrose-BSA solution, adding 0.05 ML f ProClin 300 (Supelco #4-8127), and adding additional deionized water to bring the volume to 100 mL.

After it was ensured that all desired areas were contacted the BSA-Sucrose blocked capillary tube was then incubated for 1–24 hours at room temperature. After incubation the capillary tube was centrifuged at 1000 rpm for 10±5 minutes to spin dry the capillary tube.

The BSA-biotin and BSA-Sucrose coated capillary tube was then stored in a desiccated, foil ziplock bag at 4° C. until further coating was required. The capillary tube is stable for long periods at this condition.

NeutrAvidin-4-Amino-Penicillinic Acid Capillary Coating

The BSA-biotin/BSA-Sucrose coated capillary tube was immersed in a solution of 40 µg/mL neutravidin-amino-penicillinic acid (NAV-APA) conjugate, which NAV-APA conjugate solution was prepared by diluting stock NAV-APA conjugate solution diluted to 40 μg/mL with 20 mM PBS-pH 7.2.

After it was ensured that all the desired portions of the capillary tubes were contacted with solution the NAV-APA coated capillary tube was then incubated for 1–24 hours at room temperature. After incubation, the NAV-APA coated capillary tube was centrifuged at 1000 rpm for 10±5 minutes to spin dry the capillary tube.

The NAV-APA coated capillary tube was then immersed in a container containing deionized water such that all surfaces of the capillary tube were contacted by the water. The NAV-APA coated capillary tube was then centrifuged at 1000 rpm for 10±5 minutes to spin dry the capillary tube.

The NAV-APA coated capillary tube was then placed in a vacuum oven heated to 37° C. The oven was evacuated to 24 in. Hg. The coated capillary tube was heated under vacuum for 60 minutes. The oven was then turned off, the vacuum line closed, and vacuum pump turned off. The NAV-APA coated capillary tube was then kept in the evacuated oven over night.

The AquaSil®/BSA-biotin/NAV-APA coated capillary tube can be kept with the baffled insert in a desiccated, foil ziplock bag or the capillary tube can be decanted into a sealable, desiccated container and placed in a foil ziplock bag and stored at 4° C. until ready for use in a manual version of the immunoassay or for assembly of the cartridges of the present invention.

Example 10-Method for Coating a Ceftiofur Capillary Tube

One or more capillary tubes was prepared with the Aquasil® capillary coating procedure, the BSA-Biotin capillary coating procedure, and the BSA blocking procedure as described in Example 9.

The BSA-biotin and BSA-Sucrose coated capillary tube was immersed in a 20 μg/mL neutravidin-ceftiofur conjugate solution such that all desired portions of the capillary tube were contacted by the conjugate solution, which conjugate solution was prepared by diluting stock NAV-Ceftiofur conjugate solution to 20 μg/mL in 20 mM PBS-pH 7.2.

The NAV-Ceftiofur coated capillary tube was then incubated for 1–24 hours at room temperature. After incubation, the NAV-Ceftiofur coated capillary tube was centrifuged at 1000 rpm for 10±5 minutes to spin dry the capillary tube.

The NAV-Ceftiofur coated capillary tube was then immersed in a container containing deionized water such that all desired portions of the capillary tube were contacted with the deionized water.

The NAV-Ceftiofur coated capillary tube was then centrifuged at 1000 rpm for 10±5 minutes to spin dry the capillary tube.

The NAV-Ceftiofur coated capillary tube was then placed in a vacuum oven heated to 37° C. The oven was evacuated to 25 in. Hg. The coated capillary tube was heated under vacuum for 60 minutes. The oven was then turned off, the vacuum line closed, and vacuum pump turned off. The NAV-Ceftiofur coated capillary tube was then kept in the evacuated oven over night.

The AquaSil/BSA-biotin/NAV-Ceftiofur coated capillary tube can be kept with the baffled insert in a desiccated, foil ziplock bag or the capillary tube can be decanted into a sealable, desiccated container and placed in a foil ziplock bag and stored at 4° C. until ready for use in a manual version of the immunoassay or for assembly of the cartridges of the present invention.

Example 11-Method for Coating Cephapirin Capillary Tubes

One or more glass capillary tubes was prepared with the AquaSil coating procedure of Example 9. The AquaSil coated capillary tube was then immersed in a 25 μg/mL BSA-Cephapirin coating solution such that all desired portions of the capillary tube were contacted with the coating solution, which BSA-Cephapirin coating solution was prepared by diluting stock BSA-Cephapirin conjugate solution to 25 μg/mL with 20 mM PBS-pH 7.2.

The BSA-Cephapirin coated capillary tube was then incubated for 1–24 hours at room temperature. After incubation the capillary tube was centrifuged at 1000 rpm for 10±5 minutes to spin dry the capillary tube.

The BSA-Cephapirin coated capillary tube was then stored in a desiccated, foil ziplock bag at 4° C. until further coating was required. The capillary tube is stable for long periods at this condition.

The BSA-Cephapirin coated capillary tube was then coated with the BSA blocking solution described in Example 9. The BSA-Cephapirin coated and BSA-sucrose blocked capillary tube was then immersed in a container containing deionized water such that all desired portions of the capillary tube were contacted with the water.

The BSA-Cephapirin coated and BSA-sucrose blocked coated capillary tube was then centrifuged at 1000 rpm for 10±5 minutes to spin dry the capillary tube.

The BSA-Cephapirin coated and BSA-sucrose blocked capillary tube was then placed in a vacuum oven heated to 37° C. The oven was evacuated to 25 in. Hg. The coated capillary tube was heated under vacuum for 60 minutes. The oven was then turned off, the vacuum line closed, and vacuum pump turned off. The NAV-Ceftiofur coated capillary tube was then kept in the evacuated oven over night.

The AquaSil®/BSA-Cephapirin/BSA-sucrose coated capillary tube can be kept with the baffled insert in a desiccated, foil ziplock bag or the capillary tube can be decanted into a sealable, desiccated container and placed in a foil ziplock bag and stored at 4° C. until ready for use in a manual version of the immunoassay or for assembly of the cartridges of the present invention.

Example 12-Method of the Immunoassay Used With the Devices and Apparatus of the Present Invention The immunoassay was begun by placing preferred embodiments of the cartridge and sample tray on a preferred embodiment of the apparatus of the present invention (also called the Parallux Processor Idetek, Sunnyvale, Calif.) and adding 100 microliters of raw, unpasteurized milk into each well of the sample tray. A barcode with calibration information for the particular kit was scanned. Appropriate identification information was entered via the keypad, and the apparatus began running the immunoassay. Movement of magnets by the magnetic mixer under the tray agitated the metal washers in the sample tray-wells for 20 seconds so the dry reagent comprising a fluorescent label in each well was homogeneously dissolved in the sample milk. After mixing, the sample tray was raised by the lift motor so that the tips of the capillary tubes in the cartridge were immersed in the milk. A syringe pump was actuated to draw milk into the capillary tubes, where it remained for an incubation period of two minutes. Upon completion of incubation, the syringe pump was used to wash out all contents of the tubes into the tray. The wash solution came from a reservoir in the apparatus. The sample tray was discarded, and the cartridge was placed on the centrifuge (called a read station). The centrifuge spun at 3000 rpm for 20 seconds to eject any remaining wash solution from the tubes. This step was followed by exposure to a diode laser beam for measurement of fluorescence. The fluorescence signals from each tube were collected, amplified, converted to a digital signal and processed.

The cartridge used in this Example contained reagents for three separate immunoassays. The fourth tube and corresponding well were blank. The first immunoassay was for cephapirin, the second for ceftiofur, and the third for the penicillin family of drugs (penicillin G, ampicillin, cloxacillin, and amoxicillin). Therefore, a single cartridge was able to screen for six analytes.

For semi-quantitative immunoassays, the fluorescence signals were compared to a value that had been input by the barcode. Any measured fluorescence value above the barcoded value resulted in a pass, and any measured value equal to or below the barcoded value resulted in a fail.

For quantitative immunoassays, the raw fluorescence signals were plotted as a function of spiked concentration in raw milk to produce a multi-level standard curve as shown in FIG. 18, e.g., for the Penicillin G immununoassay.

Although the foregoing invention has been described in some detail by way of illustration and example for purposes of clarity of understanding, it will be obvious that certain changes and modifications can be practiced within the scope of the appended claims. Therefore, the spirit and scope of the appended claims should not be limited to the description of preferred versions contained herein

What is claimed is:

1. An apparatus for screening for at least one analyte in a sample, which apparatus comprises:
   a reservoir for a fluid;
   a conduit to transport the fluid to a port;
   the port being positioned to draw the sample thereto and to pump fluid therethrough;
   a means to draw at least a portion of the sample to the port;
   a means to pump the fluid through the port;
   a first section having connecting means for a cartridge holding at least one capillary tube so that one end of the capillary tube is in fluid communication with the port;
   a second section having means to hold a tray having at least one well to communicate with the other end of the capillary tube, the second section also having a means to create a changing magnetic field so that a magnetizable metallic object held within the well of the tray is moved sufficiently to agitate a sample when placed in the well;
   a means to hold the cartridge and capillary tube to permit the capillary tube to be exposed to a signal generation means;
   the signal generation means; and
   a signal detection means positioned to detect a signal emitted from the capillary tube as a result of exposure to the signal from the signal generation means.

2. The apparatus of claim 1, further comprising means to dry the capillary tube while in the cartridge, which drying occurs prior to detection of the emitted signal.

3. The apparatus of claim 2, wherein the means to dry the capillary tube comprises a centrifuge with a means to secure and spin the cartridge for a sufficient time and at a sufficient speed to dry the capillary tube, wherein the means to secure and spin the cartridge is arranged such that each capillary tube can be positioned in the path of the signal generation means so that the signal detection means can collect the emitted signal.

4. The apparatus of claim 2, wherein the means to dry the capillary tube comprises means for aspirating the capillary tube with a stream of gas.

5. The apparatus of claim 1, wherein the cartridge comprises:
   a frame for holding a plurality of capillary tubes in a spaced-apart manner;
   at least one region in said frame to expose at least a portion of each capillary tube to enable a signal from the signal generating means to contact a portion of each tube; and a holder located in the frame for sealingly holding one end of each of the capillary tubes and designed so that fluid can pass therethrough.

6. The apparatus of claim 5, wherein the holder is defined by a cap and a receptacle such that the cap in conjunction with the receptacle defines a chamber that connects each of the capillary tubes in fluid communication and leads to a chamber port that is associated with the first port.

7. The apparatus of claim 1, wherein the tray comprises,
   a reservoir sufficient to hold a quantity of fluid,
   a shelf for holding multiple portions of a sample, the shelf having a plurality of spaced-apart wells therein, at least one of the wells having a reagent therein so that a portion of a sample to be tested for an analyte can be placed in each well.

8. The apparatus of claim 7, wherein at least one well in the tray has a metallic object held therein for mixing the contents of the well by creating an oscillating magnetic field under the well.

9. The apparatus of claim 1, wherein the signal generation means is selected from the group consisting of a laser and a tungsten lamp.

10. The apparatus of claim 9, wherein the signal detection means comprises a fluorescence detector.

11. The apparatus of claim 1, wherein the amount of the analyte is determined from the signal emitted from the capillary tube.

12. The apparatus of claim 1, further comprising means for performing data analysis of the signal emitted from the capillary tube.

13. The apparatus of claim 12, wherein the apparatus also includes a data presentation means connected to said means for performing data analysis that comprises a digital display, a printout, a computer storable file, an output to an external device, or any combination of the foregoing.

14. The apparatus of claim 11, further comprising means for performing data analysis of the signal emitted from the capillary tube.

15. An apparatus for screening for at least one analyte in a sample, which apparatus comprises:
   a port;
   a first section having connecting means for a cartridge holding at least one capillary tube so that one end of the capillary tube is in fluid communication with the port;
   a second section having means to hold a tray having at least one well adapted to contain sample therein to communicate with the other end of the capillary tube;
   means communicating with the port to draw at least a portion of the sample in the well of the tray to the port and into the capillary tube;
   means communicating with the port to evacuate the sample from the capillary tube;

signal generation means;

a means to hold the cartridge and capillary tube to permit the capillary tube to be exposed to the signal generation means; and a signal detection means positioned to detect a signal emitted from the capillary tube as a result of exposure to the signal from the signal generation means.

16. The apparatus of claim 15, further comprising means to dry the capillary tube while in the cartridge, which drying occurs prior to detection of the emitted signal.

17. The apparatus of claim 16, wherein the means to dry the capillary tube comprises a centrifuge with a means to secure and spin the cartridge for a sufficient time and at a sufficient speed to dry the capillary tube, wherein the means to secure and spin the cartridge is arranged such that each capillary tube can be positioned in the path of the signal generation means so that the signal detection means can collect the emitted signal.

18. The apparatus of claim 16, wherein the means to dry the capillary tube comprises means for aspirating the capillary tube with a stream of gas.

19. The apparatus of claim 15, wherein the cartridge comprises:

a frame for holding a plurality of capillary tubes in a spaced-apart manner;

at least one region in said frame to expose at least a portion of each capillary tube to enable a signal from the signal generating means to contact a portion of each tube; and a holder located in the frame for sealingly holding one end of each of the capillary tubes and designed so that fluid can pass therethrough.

20. The apparatus of claim 19, wherein the holder is defined by a cap and a receptacle such that the cap in conjunction with the receptacle defines a chamber that connects each of the capillary tubes in fluid communication and leads to a chamber port that is associated with the first port.

21. The apparatus of claim 15, wherein the tray comprises, a reservoir sufficient to hold a quantity of fluid, a shelf for holding multiple portions of a sample, the shelf having a plurality of spaced-apart wells therein, at least one of the wells having a reagent therein so that a portion of a sample to be tested for an analyte can be placed in each well.

22. The apparatus of claim 19, wherein at least one well in the tray has a metallic object held therein for mixing the contents of the well by creating an oscillating magnetic field under the well.

23. The apparatus of claim 15, wherein the signal generation means is selected from the group consisting of a laser and a tungsten lamp.

24. The apparatus of claim 23, wherein the signal detection means comprises a fluorescence detector.

25. The apparatus of claim 15, wherein the amount of the analyte is determined from the signal emitted from the capillary tube.

26. The apparatus of claim 15, further comprising means for performing data analysis of the signal emitted from the capillary tube.

27. The apparatus of claim 26, wherein the apparatus also includes a data presentation means connected to said means for performing data analysis that comprises a digital display, a printout, a computer storable file, an output to an external device, or any combination of the foregoing.

28. The apparatus of claim 25, further comprising means for performing data analysis of the signal emitted from the capillary tube.

29. An apparatus for screening for at least one analyte in a sample, which apparatus comprises:

a reservoir for a fluid;

a port in fluid communication with the reservoir;

a first section having connecting means for a cartridge holding at least one capillary tube so that one end of the capillary tube is in fluid communication with the port;

a second section having means to hold a tray having at least one well adapted to contain sample therein to communicate with the other end of the capillary tube;

means communicating with the port to draw at least a portion of the sample in the well of the tray to the port and into the capillary tube;

means communicating with the port to evacuate the sample from the capillary tube;

means communicating with the port to pass fluid through the port and into the capillary tube;

signal generation means;

a means to hold the cartridge and capillary tube to permit the capillary tube to be exposed to the signal generation means; and a signal detection means positioned to detect a signal emitted from the capillary tube as a result of exposure to the signal from the signal generation means.

30. The apparatus of claim 29, further comprising means to dry the capillary tube while in the cartridge, which drying occurs prior to detection of the emitted signal.

31. The apparatus of claim 30, wherein the means to dry the capillary tube comprises a centrifuge with a means to secure and spin the cartridge for a sufficient time and at a sufficient speed to dry the capillary tube, wherein the means to secure and spin the cartridge is arranged such that each capillary tube can be positioned in the path of the signal generation means so that the signal detection means can collect the emitted signal.

32. The apparatus of claim 30, wherein the means to dry the capillary tube comprises means for aspirating the capillary tube with a stream of gas.

33. The apparatus of claim 29, wherein the cartridge comprises a frame for holding a plurality of capillary tubes in a spaced-apart manner;

at least one region in said frame to expose at least a portion of each capillary tube to enable a signal from the signal generating means to contact a portion of each tube; and a holder located in the frame for sealingly holding one end of each of the capillary tubes and designed so that fluid can pass therethrough.

34. The apparatus of claim 33, wherein the holder is defined by a cap and a receptacle such that the cap in conjunction with the receptacle defines a chamber that connects each of the capillary tubes to each other in fluid communication and leads to a chamber port that can be associated with the first port.

35. The apparatus of claim 29, wherein the tray comprises, a reservoir sufficient to hold a quantity of fluid, a shelf for holding multiple portions of a sample, the shelf having a plurality of spaced-apart wells therein, at least one of the wells having a reagent therein so that a portion of a sample to be tested for an analyte can be placed in each well.

36. The apparatus of claim 35, wherein at least one well in the tray has a metallic object held therein for mixing the contents of the well by creating an oscillating magnetic field under the well.

37. The apparatus of claim 29, wherein the signal generation means is selected from the group consisting of a laser and a tungsten lamp.

38. The apparatus of claim 37, wherein the signal detection means comprises a fluorescence detector.

39. The apparatus of claim 29, wherein the amount of the analyte is determined from the signal emitted from the capillary tube.

40. The apparatus of claim 29, further comprising means for performing data analysis of the signal emitted from the capillary tube.

41. The apparatus of claim 40, wherein the apparatus also includes a data presentation means connected to said means for performing data analysis that comprises a digital display, a printout, a computer storable file, an output to an external device, or any combination of the foregoing.

42. The apparatus of claim 41, further comprising means for performing data analysis of the signal emitted from the capillary tube.

* * * * *